US008912385B2

(12) United States Patent
Meagher

(10) Patent No.: US 8,912,385 B2
(45) Date of Patent: Dec. 16, 2014

(54) RAPID PRODUCTION OF MONOCLONAL ANTIBODIES

(75) Inventor: Richard B. Meagher, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 12/620,209

(22) Filed: Nov. 17, 2009

(65) Prior Publication Data

US 2010/0287632 A1     Nov. 11, 2010

Related U.S. Application Data

(62) Division of application No. 11/600,595, filed on Nov. 16, 2006, now Pat. No. 7,629,171, which is a division of application No. 10/079,130, filed on Feb. 20, 2002, now Pat. No. 7,148,040.

(60) Provisional application No. 60/270,322, filed on Feb. 20, 2001.

(51) Int. Cl.
| | | |
|---|---|---|
| *A01K 67/00* | (2006.01) | |
| *A01K 67/033* | (2006.01) | |
| *C12N 5/00* | (2006.01) | |
| *C12N 5/02* | (2006.01) | |
| *G01N 33/574* | (2006.01) | |
| *C12N 5/16* | (2006.01) | |
| *C07K 16/40* | (2006.01) | |
| *G01N 33/50* | (2006.01) | |

(52) U.S. Cl.
CPC ............... *C12N 5/163* (2013.01); *C07K 16/40* (2013.01); *G01N 33/5052* (2013.01); *C12N 2510/02* (2013.01); *C12N 2517/02* (2013.01); *G01N 2800/52* (2013.01)
USPC ............... 800/13; 800/14; 435/325; 435/326; 435/328; 435/7.24

(58) Field of Classification Search
None
See application file for complete search history.

(56) References Cited

U.S. PATENT DOCUMENTS

| | | | | |
|---|---|---|---|---|
| 4,816,567 | A | 3/1989 | Cabilly | 530/387 |
| 4,978,625 | A | 12/1990 | Wagner | 436/518 |
| 5,212,072 | A | 5/1993 | Blalock | 435/69.1 |
| 5,264,341 | A | 11/1993 | Maciak | 435/7.21 |
| 5,464,758 | A | 11/1995 | Gossen | 435/69.1 |
| 5,503,995 | A | 4/1996 | Khudyakov | 435/91.1 |
| 5,627,052 | A | 5/1997 | Schrader | 435/69.6 |
| 5,877,397 | A * | 3/1999 | Lonberg et al. | 800/18 |
| 6,111,166 | A | 8/2000 | Van De Winkel | 800/13 |
| 6,331,415 | B1 | 12/2001 | Cabilly | 435/326 |
| 7,148,010 | B2 | 12/2006 | Nagel | 435/6 |
| 7,148,040 | B2 | 12/2006 | Meagher | 424/133.1 |
| 7,629,171 | B2 | 12/2009 | Meagher | 435/455 |

FOREIGN PATENT DOCUMENTS

| | | |
|---|---|---|
| AU | 2002253981 | 8/2003 |
| CA | 2438818 | 8/2003 |
| DE | 19900635 | 7/2000 |
| EP | 1362093 | 11/2010 |
| JP | 20044525627 | 8/2004 |
| WO | WO/02/066618 | 8/2002 |

OTHER PUBLICATIONS

Patil The AAPS Journal, 7(1): Article 9, E61-E77, 2005.*
Kistner PNAS, 1996, 93:10933-10938.*
U.S. Appl. No. 60/270,322, filed Feb. 20, 2001, Meagher.
Blattner FR, et al. The complete genome sequence of *Escherichia coli* K-12. Science. Sep. 5, 1997;277(5331): 1453-62.
Bunk. Immortalizing Human Cells. The Scientist 14: (2 pages) (2000).
Burcin MM, et al. A regulatory system for target gene expression. Front Biosci. Jan. 1, 1998;3: c1-7.
Cox ME, et al. Neurite extension and protein tyrosine phosphorylation elicited by inducible expression of the v-src oncogene in a PC12 cell line. Exp Cell Res. Aug. 1991; 195(2): 423-31.
Cunningham BC, et al. Receptor and antibody epitopes in human growth hormone identified by homolog-scanning mutagenesis. Science. Mar. 10, 1989;243(4896): 1330-6.
Diener E, et al. Specific immunosuppression by immunotoxins containing daunomycin. Science. Jan. 10, 1986;231(4734): 148-50.
Dunham I, et al. The DNA sequence of human chromosome 22. Nature. Dec. 2, 1999;402(6761): 489-95.
Ferretti L, et al. Total synthesis of a gene for bovine rhodopsin. Proc Natl Acad Sci U S A. Feb. 1986;83(3): 599-603.
Galibert F, et al. Complete nucleotide sequence of *Saccharomyces cerevisiae* chromosome X. EMBO J. May 1, 1996;15(9): 2031-49.
Gu H, et al. Deletion of a DNA polymerase beta gene segment in T cells using cell type-specific gene targeting. Science. Jul. 1, 1994;265(5168): 103-6.
Ho DY, et al. Inducible gene expression from defective herpes simplex virus vectors using the tetracycline-responsive promoter system. Brain Res Mol Brain Res. Sep. 5, 1996;41(1-2): 200-9.
Hofmann A, et al. Rapid retroviral delivery of tetracycline-inducible genes in a single autoregulatory cassette. Proc Natl Acad Sci U S A. May 28, 1996;93(11): 5185-90.
Jo D, et al. Epigenetic regulation of gene structure and function with a cell-permeable Cre recombinase. Nat Biotechnol. Oct. 2001;19(10): 929-33.
Kozbor D, et al. A human hybrid myeloma for production of human monoclonal antibodies. J Immunol. Dec. 1984;133(6): 3001-5.
Kühn R, et al. Inducible gene targeting in mice. Science. Sep. 8, 1995;269(5229): 1427-9.
Lakso M, et al. Targeted oncogene activation by site-specific recombination in transgenic mice. Proc Natl Acad Sci U S A. Jul. 15, 1992;89(14): 6232-6.
Maruyama M, et al. Memory B-cell persistence is independent of persisting immunizing antigen. Nature. Oct. 5, 2000;407(6804): 636-42.

(Continued)

*Primary Examiner* — Valarie Bertoglio
(74) *Attorney, Agent, or Firm* — Smith Gambrell & Russell LLP

(57) ABSTRACT

The present invention relates to genetically altered hybridomas, myelomas and B cells. The invention also relates to utilizing genetically altered hybridomas, myelomas and B cells in methods of making monoclonal antibodies. The present invention also provides populations of hybridomas and B cells that can be utilized to make a monoclonal antibody of interest.

16 Claims, 15 Drawing Sheets

(56) References Cited

OTHER PUBLICATIONS

Massie B, et al. Inducible overexpression of a toxic protein by an adenovirus vector with a tetracycline-regulatable expression cassette. J Virol. Mar. 1998;72(3): 2289-96.
McClelland M, et al. Comparison of sample sequences of the *Salmonella typhi* genome to the sequence of the complete *Escherichia coli* K-12 genome. Infect Immun. Sep. 1998;66(9): 4305-12.
Müllner S, et al. Proteomics—a new way for drug target discovery. Arzneimittelforschung. Jan. 1998;48(1): 93-5 (abstract in English).
Munson PJ, et al. Ligand: a versatile computerized approach for characterization of ligand-binding systems. Anal Biochem. Sep. 1, 1980;107(1): 220-39.
Orban PC, et al. Tissue- and site-specific DNA recombination in transgenic mice. Proc Natl Acad Sci U S A. Aug. 1, 1992;89(15): 6861-5.
Patil SD, et al. DNA-based therapeutics and DNA delivery systems: a comprehensive review. AAPS J. Apr. 8, 2005;7(1): E61-77.
Sambrook et al. Molecular Cloning, a Laboratory Manual. Cold Spring Harbor Laboratory Press (1989).
Sato S, et al. Structural analysis of *Arabidopsis thaliana* chromosome 5. X. Sequence features of the regions of 3,076,755 by covered by sixty P1 and TAC clones. DNA Res. Feb. 28, 2000;7(1): 31-63.
Van Brunt J. Companies load up on magic bullets, Signals Magazine, (7 pages) Oct. 1-9, 2000.
Smith M. In vitro mutagenesis. Annu Rev Genet. 1985;19: 423-62.
Yang XJ, et al. A p300/CBP-associated factor that competes with the adenoviral oncoprotein E1A. Nature. Jul. 25, 1996;382(6589):319-24.
Yoshida Y, et al. VSV-G-pseudotyped retroviral packaging through adenovirus-mediated inducible gene expression. Biochem Biophys Res Commun. Mar. 17, 1997;232(2): 379-82.
Zoller MJ. New molecular biology methods for protein engineering. Curr Opin Biotechnol. Aug. 1991;2(4): 526-31.
Attwood TK. Genomics. The Babel of bioinformatics. Science. Oct. 20, 2000; 290 (5491): 471-3.
Skolnick J, et al. From genes to protein structure and function: novel applications of computational approaches in the genomic era. Trends Biotechnol. Jan. 2000; 18 (1): 34-9.
Antczak D.F. "Monoclonal antibodies: technology and potential use" J Am Vet Med Assoc 181, 1005-10, 1982.
Condon et al. "Aberrant trafficking of the B cell receptor Ig-alpha beta subunit in a B lymphoma cell line" J Immunol 165, 1427-37, 2000.
Coursen et al. "Genomic instability and telomerase activity in human bronchial epithelial cells during immortalization by human papillomavirus-16 E6 and E7 genes" Exp Cell Res 235, 245-53, 1997.
DeFranco et al. "Structure and Function of the B-Cell Antigen Receptor" Chem Immunol. 59:156-172, 1994.
Dickson et al. "Human keratinocytes that express hTERT and also bypass a p16(INK4a)-enforced mechanism that limits life span become immortal yet retain normal growth and differentiation characteristics" Mol Cell Biol 20(4):1436-47, 2000.
Edwalds-Gilbert et al. "Alternative poly(A) site selection in complex transcription units: means to an end?" Nucleic Acids Res 25, 2547-2561, 1997.
Edwalds-Gilbert, G. and Milcarek, C. "Regulation of poly(A) site use during mouse B-cell development involves a change in the binding of a general polyadenylation factor in a B-cell stage-specific manner" Molecular and Cellular Biology 15, 6420-6429, 1995.
Edwards-Gilbert, G. and Milcarek, C. "The binding of a subunit of the general polyadenylation factor cleavage polyadenylation specificity factor CPSF) to polyadenylation sites changes during B cell development" Nucleic Acids Symposium Series 33, 229-233, 1995.
Flaspohler et al. "The 3'-untranslated region of membrane exon 2 from the gamma 2a immunoglobulin gene contributes to efficient transcription termination" Journal of Biological Chemistry 270, 11903-11, 1995.
Flaspohler, J. A. and Milcarek. C. "Myelomas and lymphomas expressing the Igγ2a H chain gene have similar transcription termination regions" Journal of Immunology 144, 2802-2810, 1990.

Flaswinkel and Reth, Dual role of the tyrosine activation motif of the Ig-α protein during signal transduction via the B cell antigen receptor. The EMBO Journal 13(1):83-89, 1994.
Flaswinkel and Reth, "Molecular cloning of the Ig- α subunit of the human B-cell antigen receptor complex." Immunogenetics 36:266-269, 1992.
Fraser, C.M. and Venter, J.C. "Monoclonal antibodies to beta-adrenergic receptors: use in purification and molecular characterization of beta receptors" Proc Natl Acad Sci 77, 7034-8, 1980.
Galli et al. "Relative position and strengths of poly(A) sites as well as transcription termination are critical to membrane vs secreted mu-chain expression during B-cell development" Genes & Dev 1, 471-481, 1987.
Genovese C. and Milcarek, C. "Increased half-life of mu immunoglobulin mRNA during mouse B cell development increases its abundancy" Mol Immunol 27, 733-43, 1990.
Genovese et al. "Differential mRNA stabilities affect mRNA levels in mutant mouse myeloma cells" Somat Cell Mol Genet 17, 69-81, 1991.
Glennie, M.J. and Johnson, P.W. "Clinical trials of antibody therapy" Immunol Today 21, 403-10, 2000.
Glennie, M.J. and van de Winkel, Jan G.J. "Renaissance of cancer therapeutic antibodies." DDT 8(11):503-510, 2003.
Gold and Matsuuchi, "Signal Transduction by the Antigen Receptors of B and T Lymphocytes" International Review of Cytology 157:181-276, 1995.
Graziano and Fanger "FcγRI and FcγRII on Monocytes and Granulocytes are Cytotoxic Trigger Molecules for Tumor Cells" J. of Immun. 139: 3536-3541, 1987.
Green, Larry L. "Antibody engineering via genetic engineering of the mouse: XenoMouse strains are a vehicle for the facile generation of therapeutic human monoclonal antibodies." J. Immuno. Methods 231:11-23, 1999.
Greenberg et al. "Telomerase reverse transcriptase gene is a direct target of c-Myc but is not functionally equivalent in cellular transformation" Oncogene 18, 1219-26, 1999.
Greene et al. "Monoclonal antibodies to human estrogen receptor" Proc Natl Acad Sci U S A 77, 5115-9, 1980.
Guise et al. "Alternative expression of secreted and membrane forms of immunoglobulin µ-chain is regulated by transcriptional termination in stable plasmacytoma transfectants" Journal of Immunology 140, 3988-3994, 1988.
Hall, B. L. and Milcarek, C. "Sequence and polyadenylation site determination of murine immunoglobulin gamma 2a membrane 3' untranslated region" Mol Immunol 26, 819-826, 1989.
Hashimoto et al. "Alternative splicing of CD79a (Ig-alpha/mb-1) and CD79b (Ig-beta/B29) RNA transcripts in human B cells" Mol Immunol 32, 651-9, 1995.
Hattori et al. "The DNA sequence of human chromosome 21. The chromosome 21 mapping and sequencing consortium" Nature 405, 311-9, 2000.
Hombach et al. "Identification of the genes encoding the IgM-alpha and Ig-beta components of the IgM antigen receptor complex by amino-terminal sequencing" Eur J Immunol 20, 2795-9, 1990.
Hombach et al. "Molecular components of the B-cell antigen receptor complex of the IgM class" Nature 343, 760-2, 1990.
Hurwitz et al. "$C_H$ gene rearrangements in IgM-bearing B cells and in the normal splenic DNA component of hybridomas making different isotypes of antibody" Cell 22, 349-59, 1980.
Kanavaros et al. "Discordant expression of immunoglobulin and its associated molecule mb-1/CD79a is frequently found in mediastinal large B cell lymphomas" Am J Pathol 146, 735-41, 1995.
Kandasamy et al. "The late pollen specific actins in angiosperms" Plant J 18, 681-691, 1999.
Kelly, D. E., and Perry, R. P. "Transcriptional and post-transcriptional control of Ig mRNA production during B lymphocyte development" Nucleic Acids Research 14, 5431-5441, 1986.
Kim et al. "Immortalization of human embryonic fibroblasts by overexpression of c-myc and simian virus 40 large T antigen" Exp Mol Med 33, 293-8, 2001.
Kim et al. "Differential signaling through the Ig-α and Ig-β components of the B cell antigen receptor" Mol. Immunol. 23: 911-916, 1993.

(56) References Cited

OTHER PUBLICATIONS

Kiyono et al. "Both Rb/p16$^{INK4a}$ inactivation and telomerase activity are required to immortalize human epithelial cells" Nature 396, 84-8, 1998.
Kobrin, B. J. et al. Sequences near the 3'secretion-specific polyadenylation site influence levels of secretion-specific and membrane-specific IgG2b mRNA in myeloma cells Molecular and Cellular Biology 6, 1687-1697, 1986.
Kohler and Milstein. "Derivation of specific antibody-producing tissue culture and tumor lines by cell fusion." Eur. J. Immunol. 6:495-497, 1975.
Kohler, G., and Milstein, C. "Continuous cultures of fused cells secreting antibody of predefined specificity" Nature 256, 495, 1975.
Kraus et al. "Ig-α Cytoplasmic Truncation Renders Immature B Cell More Sensitive to Antigen Contact," Immunity 11:537-545, 1999.
Laird et al. "50 million years of chordate evolution: Seeking the origins of adaptive immunity." PNAS 97(13):6924-6926, 2000.
Lassman et al. "Plasma cell-regulated polyadenylation at the Ig gamma 2b secretion-specific poly(A) site" J Immunol 148, 1251-60, 1992.
Lassman, C. R., and Milcarek, C. "Regulated expression of the mouse γ2b Ig H chain gene is influenced by polyA site order and strength" J Immunol 148(8), 2578-2585, 1992.
Lebman et al. "Regulation of usage of membrane and secreted 3' termini of alpha mRNA differs from mu mRNA" Journal of Immunology 148, 3282-3289, 1992.
Leno et al. "IgG Production in Hybridoma Batch Culture: Kinetics of IgG mRNA, Cytoplasmic-, Secreted- and Membrane-Bound Antibody Levels" Journal of Biotechnology 20: 301-312, 1991.
Li et al. "Genetic diversity of the human immunoglobulin heavy chain $V_H$ region." Immunological Reviews 190:53-68, 2002.
Li et al. "Rapid isolation of monoclonal antibodies: monitoring enzymes in the phytochelatin synthesis pathway" Plant Physiol, 711-719, 2001.
Lockhart, D.J. and Winzeler, E.A. "Genomics, gene expression and DNA arrays" Nature 405, 827-36, 2000.
MacBeath, G. and Schreiber, S.L. "Printing proteins as microarrays for high-throughput function determination" Science 289, 1760-3, 2000.
Matis et al. "B-lineage regulated polyadenylation occurs on weak poly(A) sites regardless of sequence composition at the cleavage and downstream regions" Nucleic Acids Res 24, 4684-92, 1996.
Matsuuchi et al. "The membrane IgM-associated proteins MB-1 and Ig-β are sufficient to promote surface expression of a partially functional B-cell antigen receptor in a nonlymphoid cell line" Proc. Natl. Acad. Sci. USA 89:3404-3408, 1992.
McKinney et al. "Optimizing antibody production in batch hybridoma cell culture" Journal of Biotechnology 40: 31-48, 1995.
Meilhoc et al. "Application of flow cytometric measurement of surface IgG in kinetic analysis of monoclonal antibody synthesis and secretion by murine hybridoma cells" J Immunol Methods 121, 167-174, 1989.
Milcarek et al. "Changes in abundance of IgG 2a mRNA in the nucleus and cytoplasm of a murine B-lymphoma before and after fusion to a myeloma cell" Mol Immunol 33, 691-701, 1996.
Milcarek et al. "The Metabolism of a Poly(a) Minus mRNA Fraction in LeLa Cells." Cell 3:1-10, 1974.
Milcarek, C., and Hall, B. "Cell-specific expression of secreted versus membrane forms of immunoglobulin gamma 2b mRNA involves selective use of alternate polyadenylation sites" Mol Cell Biol 5, 2514-2520, 1985.
Miller et al. "Treatment of B-cell lymphoma with monoclonal anti-idiotype antibody." N Engl J Med 306, 517-22, 1982.
Milstein, C. "The hybridoma revolution: an offshoot of basic research." BioEssay 21:966-973, 1999.
Milstein, C. "With the benefit of hindsight" Immunol Today 21, 359-64, 2000.
Morio et al. "The Dictyostelium developmental cDNA project: generation and analysis of expressed sequence tags from the first-finger stage of development" DNA Res 5, 335-40, 1998.
Munn et al. "Role of Low-Affinity Fc Receptors in Antibody-Dependent Tumor Cell Phagocytosis by Human Monocyte-Derived Macrophages" Cancer Res. 51: 1117-1123, 1991.
Nygren and Uhlen. "Scaffolds for eingeering novel binding sites in proteins." Engineering and Design 7:463-469, 1997.
Oi et al. "Immunoglobulin gene expression in transformed lymphoid cells" Proc Natl Acad Sci U S A 80, 825-9, 1983.
Opitz et al. "Cyclin D1 overexpression and p53 inactivation immortalize primary oral keratinocytes by a telomerase-independent mechanism" J Clin Invest 108, 725-32, 2001.
O'Reilly et al. "Rapid hybridoma screening method for the identification of monoclonal antibodies to low-abundance cytoplasmic proteins" Biotechniques 25, 824-30, 1998.
Ozturk and Palsson: "Loss of Antibody Productivity During Long-Term Cultivation of a Hybridoma Cell Line in Low Serum and Serum-Free Media" Hybridoma 9: 167-175, 1990.
Pandey et al. "Analysis of receptor signaling pathways by mass spectrometry: identification of vav-2 as a substrate of the epidermal and platelet-derived growth factor receptors" Proc Natl Acad Sci U S A 97, 179-84, 2000.
Pandey, A., and Mann, M. "Proteomics to study genes and genomes" Nature 405, 837-46, 2000.
Papavasiliou et al. "The Cytoplasmic Domains of Immunoglobulin (Ig) α and Igβ Can Independently Induce the Precursor B Cell Transition and Allelic Exclusion," J. Exp. Med 182:1389-1393, 1995.
Parks et al. "Antigen-specific identification and cloning of hybridomas with a fluorescence-activated cell sorter" Proc Natl Acad Sci U S A 76, 1962-6, 1979.
Pelanda et al. "B Cell Progenitors Are Arrested in Maturatin but Have Intact VDJ Recombination in the Absence of Ig-α and Ig-β$^1$." J. of Immun 169:865-872, 2002.
Persidis, A. "Proteomics" Nat Biotechnol 16, 393-4, 1998.
Phillips et al. "Regulation of nuclear poly(A) addition controls the expression of immunoglobulin M secretory mRNA" The EMBO Journal 20(22):6443-6452, 2001.
Rapp et al. "The Use of the Flourescent-Activated Cell Sorter to Monitor Changes in Cell-Specific Productivity and its Application to Large Scale Culture" Advances in Animal Cell Biology and Technology for BioProcesses, 129-133, 1989.
Reichlin et al. B Cell Development is Arrested at the Immature B Cell State in Mice Carrying a Mutation in the Cytoplasmic Domain of Immunoglobin b. J. Exp. Med.01, 193(1):13-23, Jan. 2001.
Reth et al. "An unsolved problem of the clonal selection theory and the model of an oligomeric B-cell antigen receptor" Immunol. Rev. 176: 10-18, 2000.
Reth et al. "The B-cell antigen receptor complex." Immun Today 12(6):196-201, 1991.
Reth, Michael "Antigen Receptors on B Lymphocytes." Annu. Rev. Immunol. 10:97-121, 1992.
Richards et al. "Reconstitution of B cell antigen receptor-induced signaling events in a nonlymphoid cell line by expressing the Syk protein-tyrosine kinase" J Biol Chem 271, 6458-66, 1996.
Russo et al. "A telomere-independent senescence mechanism is the sole barrier to Syrian hamster cell immortalization" Oncogene 17, 3417-26, 1998.
Sakaguchi et al. "B lymphocyte lineage-restricted expression of mb-1, a gene with CD3-like structural properties" Embo J 7, 3457-64, 1988.
Schamel and Reth, "Stability of the B cell antigen receptor complex." Molecular Immunology 37:253-259, 2000.
Schildbach et al. "Contribution of a single heavy chain residue to specificity of an anti-digoxin monoclonal antibody" Protein Science 3:737-749, 1994.
Stevens et al. "A Mutation of the µ Transmembrane that Disrupts Endoplasmic Reticulum Retention," J. Immunol. 4397-4406, 1994.
Sun et al. "Transfectomas expressing both secreted and membrane-bound forms of chimeric IgE with anti-viral specificity" J Immunol 146, 199-205, 1991.
Syrigos et al. "Use of monoclonal antibodies for the diagnosis and treatment of bladder cancer" Hybridoma 18, 219-224, 1999.
Torris et al. "Aberrant B Cell Development and Immune Response in Mice with a Compromised BCR Complex." Science 272(5269):1804-1808, 1996.

(56) References Cited

OTHER PUBLICATIONS

Wang and Clark, "Igα: B all that you can B," J. Clin Invest. 104(8):1011-1012, 1999.
Weiser et al. The internalization of the IgG2a antigen receptor does not require the association with Ig-α and Ig-β but the activation of protein tyrosine kinases does. Eur. J. Immunol. 24:665-671, 1994.
Wienands et al. "Molecular components of the B cell antigen receptor complex of class IgD differ partly from those of IgM" EMBO Journal 9: 449-456, 1990.
Yuan, D., and Tucker, P. W. "Transcriptional regulation of the mu-delta heavy chain locus in normal murine B-lymphocytes" J Exp Medicine 160, 564-572, 1984.
International Preliminary Examination Report completed on Mar. 24, 2003 for PCT/US2002/004936 filed on Feb. 20, 2002 and published as WO/2002/066618 on Aug. 29, 2002 (Applicants—University of Georgia Research Foundation, Inc. et al. // Inventors—Meagher et al.) (5 pages).
International Search Report mailed on Jul. 15, 2002 for PCT/US2002/004936 filed on Feb. 20, 2002 and published as WO/2002/066618 on Aug. 29, 2002 (Applicants—University of Georgia Research Foundation, Inc. et al. // Inventors—Meagher et al.) (2 pages).
Preliminary Amendment, Specification, and Claims entered by the U.S. Patent & Trademark Office on Nov. 16, 2006 for U.S. Appl. No. 11/600,595, filed Nov. 16, 2006 (Applicants—University of Georgia et al.; Inventors—Meagher et al.) (17 pages).
Preliminary Amendment, Claims, Drawings, and Sequence Listing entered by the U.S. Patent & Trademark Office on May 15, 2007 for U.S. Appl. No. 11/600,595, filed Nov. 16, 2006 (Applicants—University of Georgia et al.; Inventors—Meagher et al.) (28 pages).
Requirement for Restriction/Election mailed on Nov. 14, 2007 for U.S. Appl. No. 11/600,595, filed Nov. 16, 2006 (Applicants—University of Georgia et al.; Inventors—Meagher et al.) (7 pages).
Response to Election/Restriction Requirement mailed on May 13, 2008 for U.S. Appl. No. 11/600,595, filed Nov. 16, 2006 (Applicants—University of Georgia et al.; Inventors—Meagher et al.) (4 pages).
Non-Final Rejection mailed on Aug. 29, 2008 for U.S. Appl. No. 11/600,595, filed Nov. 16, 2006 (Applicants—University of Georgia et al.; Inventors—Meagher et al.) (9 pages).
Examiner Interview Summary Record mailed on Dec. 18, 2008 for U.S. Appl. No. 11/600,595, filed Nov. 16, 2006 (Applicants—University of Georgia et al.; Inventors—Meagher et al.) (2 pages).
Amendment and Response to Office Action mailed on Dec. 29, 2008 for U.S. Appl. No. 11/600,595, filed Nov. 16, 2006 (Applicants—University of Georgia et al.; Inventors—Meagher et al.) (16 pages).
Final Rejection mailed on Apr. 17, 2009 for U.S. Appl. No. 11/600,595, filed Nov. 16, 2006 (Applicants—University of Georgia et al.; Inventors—Meagher et al.) (5 pages).
Amendment and Response to Office Action mailed Jul. 17, 2009 for U.S. Appl. No. 11/600,595, filed Nov. 16, 2006 (Applicants—University of Georgia et al.; Inventors—Meagher et al.) (9 pages).
Notice of Allowance and Fees Due mailed on Jul. 28, 2009 for U.S. Appl. No. 11/600,595, filed Nov. 16, 2006 (Applicants—University of Georgia et al.; Inventors—Meagher et al.) (4 pages).
Issue Notification issued on Dec. 8, 2009 for U.S. Appl. No. 11/600,595, filed Nov. 16, 2006 (Applicants—University of Georgia et al.; Inventors—Meagher et al.) (1 page).
Preliminary Amendment mailed on Feb. 5, 2003 for U.S. Appl. No. 10/079,130, filed Feb. 20, 2002 (Applicants—University of Georgia et al.; Inventors—Meagher et al.) (2 pages).
Amendment and Sequence Listing mailed on May 6, 2003 for U.S. Appl. No. 10/079,130, filed Feb. 20, 2002 (Applicants—University of Georgia et al.; Inventors—Meagher et al.) (9 pages).
Requirement for Restriction/Election mailed on Oct. 19, 2004 for U.S. Appl. No. 10/079,130, filed Feb. 20, 2002 (Applicants—University of Georgia et al.; Inventors—Meagher et al.) (10 pages).
Amendment and Response to Election/Restriction Requirement mailed on Nov. 16, 2004 for U.S. Appl. No. 10/079,130, filed Feb. 20, 2002 (Applicants—University of Georgia et al.; Inventors—Meagher et al.) (24 pages).
Non-Final Rejection mailed on Mar. 4, 2005 for U.S. Appl. No. 10/079,130, filed Feb. 20, 2002 (Applicants—University of Georgia et al.; Inventors—Meagher et al.) (14 pages).
Amendment and Response to Office Action mailed on Sep. 6, 2005 for U.S. Appl. No. 10/079,130, filed Feb. 20, 2002 (Applicants—University of Georgia et al.; Inventors—Meagher et al.) (65 pages).
Final Rejection mailed on Nov. 15, 2005 for U.S. Appl. No. 10/079,130, filed Feb. 20, 2002 (Applicants—University of Georgia et al.; Inventors—Meagher et al.) (8 pages).
Examiner Interview Summary Record entered by the U.S. Patent & Trademark Office on Apr. 24, 2006 for U.S. Appl. No. 10/079,130, filed Feb. 20, 2002 (Applicants—University of Georgia et al.; Inventors—Meagher et al.) (1 page).
Amendment and Response to Office Action entered by the U.S. Patent & Trademark Office on May 15, 2006 for U.S. Appl. No. 10/079,130, filed Feb. 20, 2002 (Applicants—University of Georgia et al.; Inventors—Meagher et al.) (28 pages).
Examiner Interview Summary Record for Interview on Aug. 1, 2006 for U.S. Appl. No. 10/079,130, filed Feb. 20, 2002 (Applicants—University of Georgia et al.; Inventors—Meagher et al.) (2 pages).
Notice of Allowance and Fees Due mailed on Aug. 4, 2006 for U.S. Appl. No. 10/079,130, filed Feb. 20, 2002 (Applicants—University of Georgia et al.; Inventors—Meagher et al.) (8 pages).
Issue Notification issued on Dec. 12, 2006 for U.S. Appl. No. 10/079,130, filed Feb. 20, 2002 (Applicants—University of Georgia et al.; Inventors—Meagher et al.) (1 page).
Decision to grant a European patent pursuant to Article 97(1) EPC by the European Patent Office on Oct. 21, 2010 for European Patent Application No. 02723187.7, which was filed on Feb. 20, 2002 (Applicants—University of Georgia et al.; Inventor—Meagher) (2 pages).
Communication under Rule 71(3) EPC about intention to grant a European patent mailed by the European Patent Office on May 25, 2010 for European Patent Application No. 02723187.7, which was filed on Feb. 20, 2002 (Applicants—University of Georgia et al.; Inventor—Meagher) (73 pages).
Written submission mailed Apr. 27, 2010 in reply to the Result of Consultation dated Apr. 26, 2010 and in preparation of the Oral Proceedings on Apr. 28, 2010 for European Patent Application No. 02723187.7, which was filed on Feb. 20, 2002 (Applicants—University of Georgia et al.; Inventor—Meagher) (12 pages).
Findings upon submissions and Notification relating to oral proceedings mailed Apr. 27, 2010 for European Patent Application No. 02723187.7, which was filed on Feb. 20, 2002 (Applicants—University of Georgia et al.; Inventor—Meagher) (13 pages).
Results of consultation by telephone/in person dated Apr. 26, 2010 for European Patent Application No. 02723187.7, which was filed on Feb. 20, 2002 (Applicants—University of Georgia et al.; Inventor—Meagher) (3 pages).
Written submission mailed Apr. 23, 2010 in reply to the Result of Consultation dated Apr. 14, 2010 and in preparation to the Oral Proceedings on Apr. 28, 2010 for European Patent Application No. 02723187.7, which was filed on Feb. 20, 2002 (Applicants—University of Georgia et al.; Inventor—Meagher) (115 pages).
Results of consultation by telephone/in person dated Apr. 14, 2010 for European Patent Application No. 02723187.7, which was filed on Feb. 20, 2002 (Applicants—University of Georgia et al.; Inventor—Meagher) (4 pages).
Reply mailed Mar. 29, 2010 to the Summons to Attend Oral Proceedings dated Dec. 10, 2009 and in Preparation for the Oral Proceedings on Apr. 28, 2010 for European Patent Application No. 02723187.7, which was filed on Feb. 20, 2002 (Applicants—University of Georgia et al.; Inventor—Meagher) (11 pages).
Summons to attend oral proceedings pursuant to Rule 115(1) EPC mailed Dec. 10, 2009 for European Patent Application No. 02723187.7, which was filed on Feb. 20, 2002 (Applicants—University of Georgia et al.; Inventor—Meagher) (6 pages).
Reply mailed Feb. 16, 2009 to communication from the Examining Division dated Aug. 6, 2008 for European Patent Application No.

(56) References Cited

OTHER PUBLICATIONS 02723187.7, which was filed on Feb. 20, 2002 (Applicants—University of Georgia et al.; Inventor—Meagher) (10 pages).
Communication from the Examining Division pursuant to Article 94(3) EPC dated Aug. 6, 2008 for European Patent Application No. 02723187.7, which was filed on Feb. 20, 2002 (Applicants—University of Georgia et al.; Inventor—Meagher) (5 pages).
Response mailed Feb. 18, 2008 to communication from the Examining Division pursuant to Article 96(2) EPC, dated Aug. 10, 2007 for European Patent Application No. 02723187.7, which was filed on Feb. 20, 2002 (Applicants—University of Georgia et al.; Inventor—Meagher) (19 pages).
Communication from the Examining Division pursuant to Article 96(2) EPC dated Aug. 10, 2007 for European Patent Application No. 02723187.7, which was filed on Feb. 20, 2002 (Applicants—University of Georgia et al.; Inventor—Meagher) (8 pages).
Reply mailed Nov. 15, 2006 to communication from the Examining Division dated May 5, 2006 for European Patent Application No. 02723187.7, which was filed on Feb. 20, 2002 (Applicants—University of Georgia et al.; Inventor—Meagher) (34 pages).
Communication from the Examining Division pursuant to Article 96(2) EPC dated May 5, 2006 for European Patent Application No. 02723187.7, which was filed on Feb. 20, 2002 (Applicants—University of Georgia et al.; Inventor—Meagher) (7 pages).
Supplementary European Search Report dated Mar. 24, 2004 for European Patent Application No. 02723187, which was filed on Feb. 20, 2002 (Applicants—University of Georgia et al.; Inventor—Meagher) (1 page).
Amended claims mailed Oct. 28, 2003 in response to communication pursuant to Rules 109/110 EPC dated Sep. 29, 2003 for European Patent Application No. 02723187.7, which was filed on Feb. 20, 2002 (Applicants—University of Georgia et al.; Inventor—Meagher) (13 pages).
Sequence listing mailed Oct. 10, 2003 for European Patent Application No. 02723187.7, which was filed on Feb. 20, 2002 (Applicants—University of Georgia et al.; Inventor—Meagher) (5 pages).
Priority Document dated May 14, 2002 of U.S. Appl. No. 60/270,322 for European Patent Application No. 02723187.7, which was filed on Feb. 20, 2002 (Applicants—University of Georgia et al.; Inventor—Meagher) (70 pages).
Notice of Acceptance by IP Australia Patent Office dated Feb. 7, 2008 for Australian Patent Application No. 2002253981, which was filed on Feb. 20, 2002 (Applicants—University of Georgia et al.; Inventor—Meagher) (3 pages).
Response mailed Jan. 16, 2008 to Examiner's Report dated May 19, 2006 for Australian Patent Application No. 2002253981, which was filed on Feb. 20, 2002 (Applicants—University of Georgia et al.; Inventor—Meagher) (17 pages).
Examiner's First Report mailed by IP Australia Patent Office on May 19, 2006 for Australian Patent Application No. 2002253981, which was filed on Feb. 20, 2002 (Applicants—University of Georgia et al.; Inventor—Meagher) (2 pages).
Issue Notification issued by IP Australia Patent Office on Jun. 5, 2008 for Australian Patent Application No. 2002253981, which was filed on Feb. 20, 2002 (Applicants—University of Georgia et al.; Inventor—Meagher) (2 pages).
Voluntary Amendment filed on Jan. 12, 2004 for Canadian Patent Application No. 2,438,818, which was filed on Feb. 20, 2002 (Applicants—University of Georgia et al.; Inventor—Meagher) (6 pages).
Official Action issued by the Canadian Patent Office on Jul. 8, 2008 for Canadian Patent Application No. 2,438,818, which was filed on Feb. 20, 2002 (Applicants—University of Georgia et al.; Inventor—Meagher) (5 pages).
Response to Official Action filed on Jan. 8, 2009 for Canadian Patent Application No. 2,438,818, which was filed on Feb. 20, 2002 (Applicants—University of Georgia et al.; Inventor—Meagher) (47 pages).
Response to Examiner's Requisition under Section 29 of the Patent Rules filed on Jan. 8, 2009 for Canadian Patent Application No. 2,438,818, which was filed on Feb. 20, 2002 (Applicants—University of Georgia et al.; Inventor—Meagher) (26 pages).
Voluntary Amendment filed on Jan. 9, 2009 for Canadian Patent Application No. 2,438,818, which was filed on Feb. 20, 2002 (Applicants—University of Georgia et al.; Inventor—Meagher) (18 pages).
Official Action issued by the Canadian Patent Office on Mar. 10, 2010 for Canadian Patent Application No. 2,438,818, which was filed on Feb. 20, 2002 (Applicants—University of Georgia et al.; Inventor—Meagher) (5 pages).
Response to Official Action filed on Sep. 10, 2010 for Canadian Patent Application No. 2,438,818, which was filed on Feb. 20, 2002 (Applicants—University of Georgia et al.; Inventor—Meagher) (26 pages).
Official Action issued by the Canadian Patent Office on Sep. 19, 2011 for Canadian Patent Application No. 2,438,818, which was filed on Feb. 20, 2002 (Applicants—University of Georgia et al.; Inventor—Meagher) (5 pages).
Notice of Allowance issued by the Canadian Patent Office on Oct. 16, 2012 for Canadian Patent Application No. 2,438,818, which was filed on Feb. 20, 2002 (Applicants—University of Georgia et al.; Inventor—Meagher) (1 page).

* cited by examiner

Igα-1S (sense oligo for Igα containing and SpeI and HindIII cloning sites)
5' TAG TGA ACT AGT AAG CTT GCC ACC ATG CCA GGG GGT CTA GAA GCC CTC A 3'

Igα-221A (antisense oligo for Igα containing EcoRI and ClaI cloning sites)
5' GTC TAG ATC GAT GAA TTC TCA TGG CTT TTC CAG CTG GGC ATC 3'

Igβ-IS (sense oligo for Igβ containing SpeI and HindIII cloning sites)
5 ' TAG TGA ACT AGT AAG CTT GCC ACC ATG GCC ACA CTG GTG CTG TCT TCC ATG 3'

IgB-229A (antisense oligo for Igβ containing XhoI and ClaI cloning sites)
5' GTC TAG ATC GAT CTC GAG TCA TTC CTG GCC TGG ATG CTC TCC TAC CGA 3'

FIG.2A p3.1Neo1g_    Length: 681
    Translation

```
HindIII Signal M   P   G   G   L   E   A   L   R   A   L   P   L
AAGCTT GCCACC ATG CCA GGG GGT CTA GAA GCC CTC AGA GCC CTG CCT CTC L   L   F   L   S   Y   A   C   L   G   P   G   C   Q   A   L   R
       CTC CTC TTC TTG TCA TAC GCC TGT TTG GGT CCC GGA TGC CAG GCC CTG CGG V   E   G   G   P   P   S   L   T   V   N   L   G   E   E   A   R
       GTA GAA GGG GGT CCA CCA TCC CTG ACG GTG AAC TTG GGC GAG GAG GCC CGC L   T   C   E   N   N   G   R   N   P   N   I   T   W   W   F   S
       CTC ACC TGT GAA AAC AAT GGC AGG AAC CCT AAT ATC ACA TGG TGG TTC AGC L   Q   S   N   I   T   W   P   P   V   P   L   G   P   G   Q   G
       CTT CAG TCT AAC ATC ACA TGG CCC CCA GTG CCA CTG GGT CCT GGC CAG GGT T   T   G   Q   L   F   F   P   E   V   N   K   N   H   R   G   L
       ACC ACA GGC CAG CTG TTC TTC CCC GAA GTA AAC AAG AAC CAC AGG GGC TTG Y   W   C   Q   V   I   E   N   N   I   L   K   R   S   C   G   T
       TAC TGG TGC CAA GTG ATA GAA AAC AAC ATA TTA AAA CGC TCC TGT GGT ACT Y   L   R   V   R   N   P   V   P   R   P   F   L   D   M   G   E
       TAC CTC CGC GTG CGC AAT CCA GTC CCT AGG CCC TTC CTG GAC ATG GGG AAA G   T   K   N   R   I   I   T   A   E   G   I   I   L   L   F   C
       GGT ACC AAG AAC CGC ATC ATC ACA GCA GAA GGG ATC ATC TTG CTG TTC TGT A   V   V   P   G   T   L   L   L   F   R   K   R   W   Q   N   E
       GCA GTG GTG CCA GGG ACG CTG CTG CTA TTC AGG AAA CGG TGG CAA AAT GAG K   F   G   V   D   M   P   D   D   Y   E   D   E   N   L   Y   E
       AAG TTT GGG GTG GAC ATG CCA GAT GAC TAT GAA GAT GAA AAT CTC TAT GAG G   L   N   L   D   D   C   S   M   Y   E   D   I   S   R   G   L
       GGC CTG AAC CTT GAT GAC TGT TCT ATG TAT GAG GAC ATC TCC AGG GGA CTC Q   G   T   Y   Q   D   V   G   N   L   H   I   G   D   A   Q   L
       CAG GGC ACC TAC CAG GAT GTG GGC AAC CTC CAC ATT GGA GAT GCC CAG CTG E   K   P   *   EcoRI
       GAA AAG CCA TGA GAATTC
```

FIG.3

P3.1ZeoIg_    Length: 705
      Translation

```
HindIII Signal M   A   T   L   V   L   S   S   M   P   C   H   W
AAGCTT GCCACC ATG GCC ACA CTG GTG CTG TCT TCC ATG CCC TGC CAC TGG L   L   F   L   L   L   L   F   S   G   E   P   V   P   A   M   T
        CTG TTG TTC CTG CTG CTG CTC TTC TCA GGT GAG CCG GTA CCA GCA ATG ACA S   S   D   L   P   L   N   F   Q   G   S   P   C   S   Q   I   W
        AGC AGT GAC CTG CCA CTG AAT TTC CAA GGA AGC CCT TGT TCC CAG ATC TGG Q   H   P   R   F   A   A   K   K   R   S   S   M   V   K   F   H
        CAG CAC CCG AGG TTT GCA GCC AAA AAG CGG AGC TCC ATG GTG AAG TTT CAC C   Y   T   N   H   S   G   A   L   T   W   F   R   K   R   G   S
        TGC TAC ACA AAC CAC TCA GGT GCA CTG ACC TGG TTC CGA AAG CGA GGG AGC Q   Q   P   Q   E   L   V   S   E   E   G   R   I   V   Q   T   Q
        CAG CAG CCC CAG GAA CTG GTC TCA GAA GAG GGA CGC ATT GTG CAG ACC CAG N   G   S   V   Y   T   L   T   I   Q   N   I   Q   Y   E   D   N
        AAT GGC TCT GTC TAC ACC CTC ACT ATC CAA AAC ATC CAG TAC GAG GAT AAT G   I   Y   F   C   K   Q   K   C   D   S   A   N   H   N   V   T
        GGT ATC TAC TTC TGC AAG CAG AAA TGT GAC AGC GCC AAC CAT AAT GTC ACC D   S   C   G   T   E   L   L   V   L   G   F   S   T   L   D   Q
        GAC AGC TGT GGC ACG GAA CTT CTA GTC TTA GGA TTC AGC ACG TTG GAC CAA L   K   R   R   N   T   L   K   D   G   I   I   L   I   Q   T   L
        CTG AAG CGG CGG AAC ACA CTG AAA GAT GGC ATT ATC TTG ATC CAG ACC CTC L   I   I   L   F   I   I   V   P   I   F   L   L   L   D   K   D
        CTC ATC ATC CTC TTC ATC ATT GTG CCC ATC TTC CTG CTA CTT GAC AAG GAT D   G   K   A   G   M   E   E   D   H   T   Y   E   G   L   N   I
        GAC GGC AAG GCT GGG ATG GAG GAA GAT CAC ACC TAT GAG GGC TTG AAC ATT D   Q   T   A   T   Y   E   D   I   V   T   L   R   T   G   E   V
        GAC CAG ACA GCC ACC TAT GAA GAC ATA GTG ACT CTT CGG ACA GGG GAG TA K   W   S   V   G   E   H   P   G   Q   E   *   XhoI
        AAG TGG TCG GTA GGA GAG CAT CCA GGC CAG GAA TGA CTCGAG
```

FIG.4

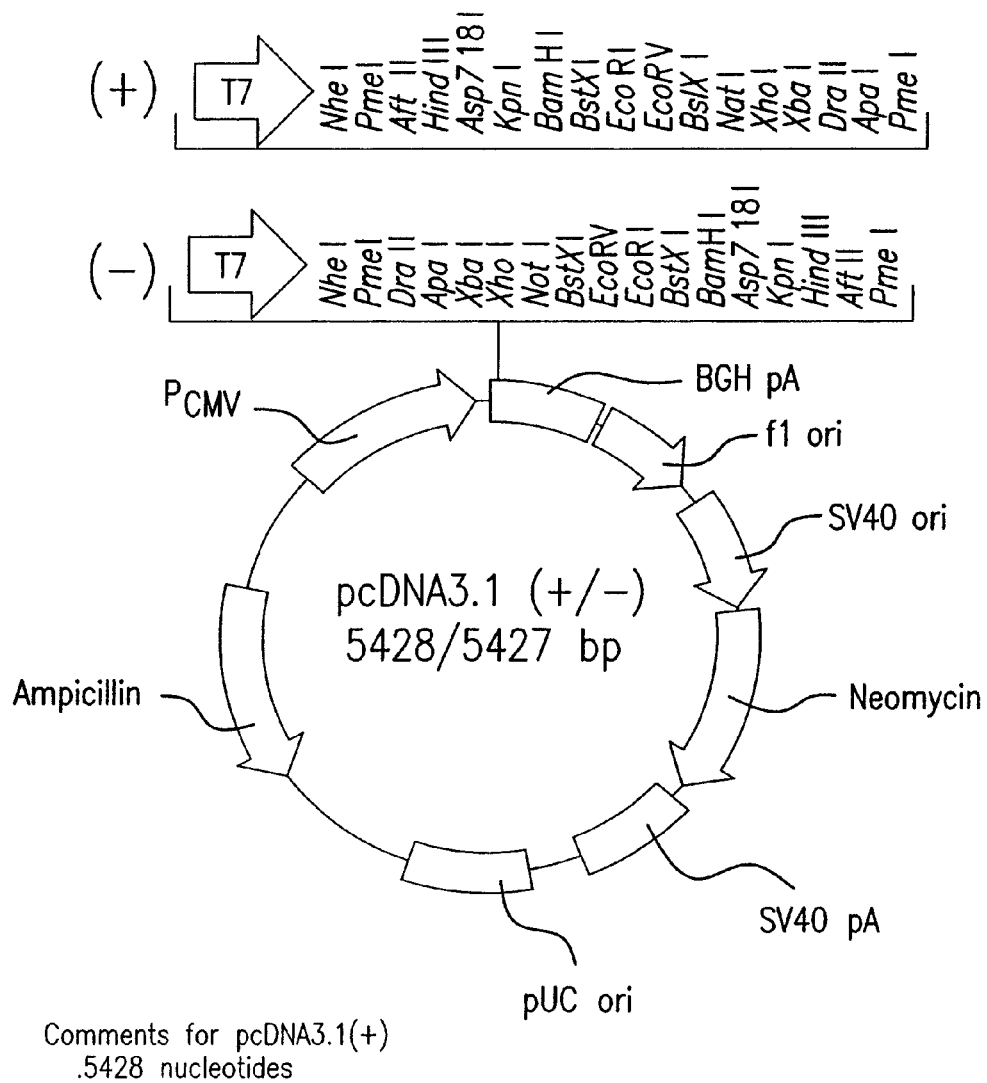

Comments for pcDNA3.1(+)
.5428 nucleotides

CMV promoter: bases 232-819
T7 promoter/priming site: bases 83-882
Multiple cloning site:bases 895-1010
pcDNA3.1/BGH reverse priming site: bases 1022-1039
BGH polyadenylation sequence: bases 1028-1252
f1:origin: bases 1298-1728
SV40 early promoter and origin: bases 1731-2074
Neomycin resistance gene (ORP): BASES 2136-2930
SV40 early polyadenylation signal bases 3104-3234
pUC origin: bases 3617-4257 complementary strand
Ampicillin resistance gene (*bla*): bases 4432-5428 (complementary strand)
ORF: bases 4482-5292 (complementary strand)
Ribosome binding site-bases 5300-5304 (complementary strand)
*bla* promoter (P3): bases 5327-5333 (complementary strand)

FIG.5

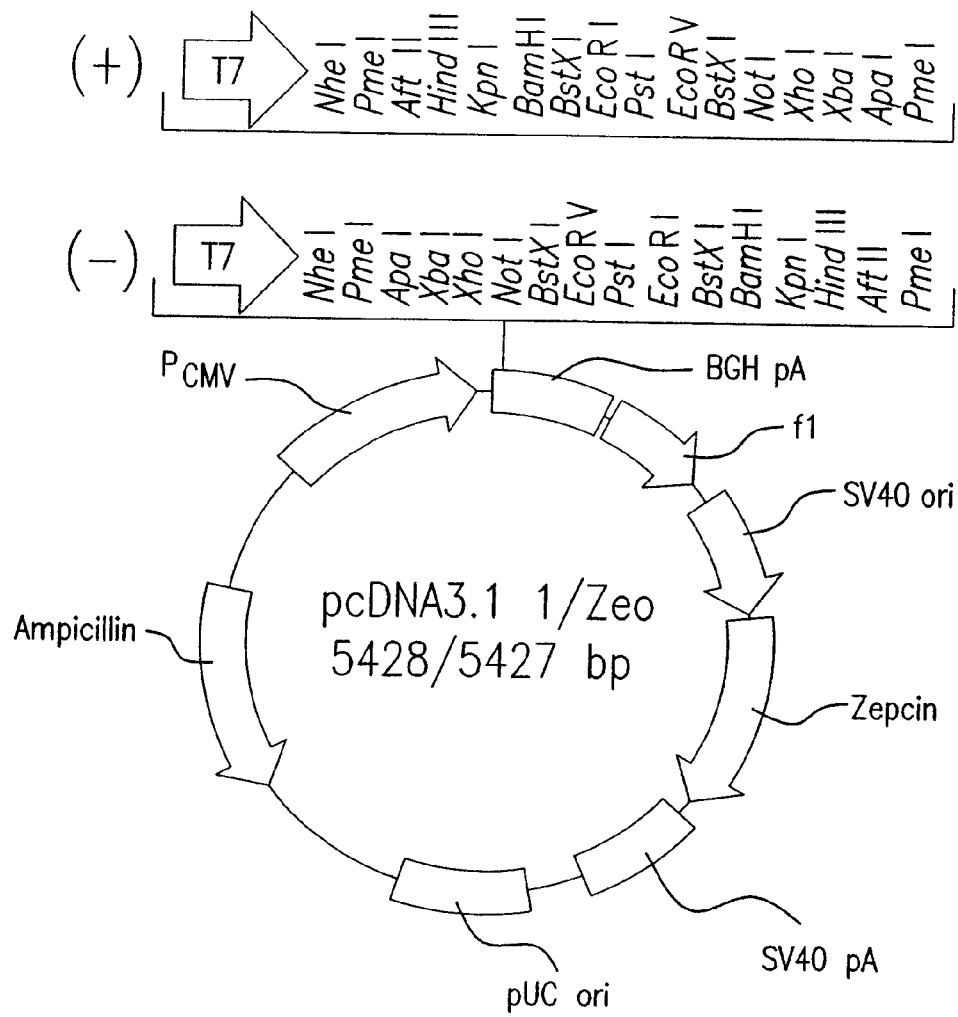

Comments for pcDNA3.1/Zeo(+)
.5015 nucleotides

CMV promoter: bases 209-863
T7 promoter priming site: bases 863-882
Multiple cloning site: bases 895-1010
BGH reverse priming site: bases 1022-1039
BGH polyadenylation signal: bases 1021-1235
f1 origin: bases 1298-1711
SV40 promoter and origin: bases 1776-2101
EM7 promoter: bases 2117-2183
Zeocin™ resistance gene: bases 2184-2558
SV40 polyadenylation: bases 2688-2827
pUC origin: bases 3201-3874
*bla* promoter: bases 4880-4978 (C)
Ampicillin (*bla*) resistance gene: bases 4019-1879 (C)

FIG.6

RAPID PRODUCTION OF MONOCLONAL ANTIBODIES

This application is a divisional of and claims priority to U.S. application Ser. No. 11/600,595, filed on Nov. 16, 2006 (now allowed) now U.S. Pat. No. 7,629,171, which is a divisional of U.S. application Ser. No. 10/079,130, filed Feb. 20, 2002, now U.S. Pat. No. 7,148,040, which claims benefit of U.S. provisional Patent Application No. 60/270,322, filed Feb. 20, 2001 and are hereby incorporated herein by reference in their entirety.

FIELD OF THE INVENTION

The present invention relates to genetically altered hybridomas, myelomas and B cells. The invention also relates to utilizing genetically altered hybridomas, myelomas and B cells in methods of making monoclonal antibodies.

BACKGROUND

Major efforts in functional genomics and proteomics are creating an unprecedented demand for monoclonal antibodies to be used for protein function studies. Monoclonal antibodies can be used in every stage of research involving protein target discovery and characterization including purification, quantification, and organ and cellular localization. Recent advances in proteomics are creating a need for large numbers of antibodies for use in high throughput studies and on protein chips. Monoclonal antibodies have been used for decades as key reagents in clinical diagnostics and they are emerging as an important new class of therapeutics agents.

Hybridoma technology is the most commonly used method for accessing monoclonal antibodies. Monoclonal antibodies are secreted from hybridoma cells, created by fusing normal antibody producing splenic B-cells with immortal myeloma cells or other immortal cells. Hybridoma production has changed little since its inception 26 years ago (Kohler and Milstein, 1975).

A typical protocol for hybridoma generation involves: (i) immunizing an animal (e.g., mouse, rat or rabbit) with a purified protein antigen; (ii) harvesting antibody producing B-cells, typically from the spleen; (iii) fusing B-cells with a non-secretory myeloma cell line deficient for the enzyme hypoxanthine guanine phosphoribosyl transferase (e.g., x63-Ag 8.653 from a BALB/c mouse strain); (iv) growing hybridoma cells in a selection medium containing hypoxanthine, aminopterin and thymidine (HAT) and (v) screening for cells that produce the desired antibody and (vi) limit dilution cloning to obtain a homogenous cell line that secretes the antibody (Antczak, 1982).

Conventional hybridoma technology does not allow researchers to access large numbers of antibodies to different antigens or large numbers of antibodies to a single target antigen in an efficient manner. Hybridoma cell cloning by limit dilution is perhaps the most problematic, time consuming and labor intensive step in generating monoclonal antibodies (O'Reilly et. al., 1998). In this step, cells are repeatedly diluted out to low cell numbers and their supernatants assayed for secreted monoclonal antibody. Screening must be artfully performed to ensure that desired hybridomas are not lost. In the case of rapidly growing hybridomas, cells may die in the microtiter wells from exhaustion of nutrients if they are not moved to larger vessels or fresh medium quickly. Also, in typical wells containing several hybridomas, undesirable hybridomas may continuously overgrow desired hybridomas. This can cause the limit dilution step to be extended weeks or months and may even result in loss of important hybridomas. If the hybridomas have not grown to a reasonable size by the time of assay, they may not have produced sufficient antibody for detection. Therefore, a time for screening supernatants must be chosen carefully. The available "window" for initial screening is not large and usually extends over two to three days (Antczak, 1982). Once started, the limit dilution isolation of pure cell lines typically goes on for 3-4 weeks for any one hybridoma.

There is a need for more rapid methods of isolating desired hybridoma cells. At least two laboratories attempted to sort normal hybridomas based on traces of surface presentation of antibody (Parks et al., 1979; Meilhoc et al., 1989). They showed that a subset of hybridoma cells in any population presented a small but measurable number (~20) of surface antibody molecules. This was enough to sort these cells when labeled with antigen, if the antigen was coupled to highly fluorescent microspheres to increase the fluorescence signal. Even with these highly fluorescent spheres the signal was only a few-fold above the background.

There is a need for a significant increase in the presentation of surface antibody on hybridoma cells as well as a need for a significant increase in the percentage of hybridoma cells presenting surface antibody in any population to enable rapid screening. The present invention provides both by providing DISH (Direct Screening of Hybridoma Cells). The DISH technology of the present invention provides a simple, rapid and reliable selection of hybridoma cells that may be accomplished in a matter of hours instead of weeks. DISH provides several significant improvements over conventional hybridoma technology that allow researchers to access much larger repertoires of antibodies in an efficient manner. Using current hybridoma protocols approximately 40,000 fusions are typically prepared. A main reason more fusions are not made is the difficulty encountered in isolating desired clones using limit dilution. DISH enables very rapid, high throughput cell selection using fluorescence activated cell sorting (FACS) and other modalities. Since FACS technology permits millions of cells to be sorted in a matter of hours, the number of hybridoma fusions one can screen using DISH technology is orders of magnitude larger than by limit dilution. Significantly, FACS sorting allows for single cell deposition of desired hybridomas into discrete wells. Hence, the problem of desirable, but slow growing cells being lost is eliminated using DISH. Thus, DISH replaces current antibody screening and limit dilution procedures with a rapid, high throughput, selection process. The present invention can also be utilized to provide populations of plasma cells that surface present adequate immunoglobulin to enable high throughput fluorescence activated cell sorting technology to be used to determine whether single plasma cells produce immunoglobin that reacts with target antigens.

SUMMARY OF THE INVENTION

The present invention provides a population of hybridoma cells wherein greater than 15% of the cells in the population express monoclonal antibody that is bound to the cell surface.

Also provided by the present invention is a population of hybridoma cells wherein greater than 25% of the cells in the population express monoclonal antibody that is bound to the cell surface.

Further provided is a population of hybridoma cells wherein greater than 50% of the cells in the population express monoclonal antibody that is bound to the cell surface.

Also provided by the present invention is a population of hybridoma cells wherein greater than 75% of the cells in the population express monoclonal antibody that is bound to the cell surface.

The present invention also provides a hybridoma cell, wherein greater than twenty monoclonal antibody molecules are expressed and bound to the cell surface.

The present invention further provides a hybridoma cell, wherein greater than fifty monoclonal antibody molecules are expressed and bound to the cell surface.

Also provided by the present invention is a hybridoma cell, wherein greater than one hundred monoclonal antibody molecules are expressed and bound to the cell surface.

Further provided by the present invention is a hybridoma cell, wherein greater than two hundred and fifty monoclonal antibody molecules are expressed and bound to the cell surface.

Also provided by the present invention is a hybridoma cell, wherein greater than five hundred monoclonal antibody molecules are expressed and bound to the cell surface.

Further provided by the present invention is a population of hybridoma cells wherein greater than 15% of the cells in the population express monoclonal antibody that is bound to the cell surface and wherein greater than twenty monoclonal antibody molecules are expressed and bound to the cell surface of the cells in the population that express monoclonal antibody.

Also provided by the present invention is a population of hybridoma cells wherein greater than 15% of the cells in the population express monoclonal antibody that is bound to the cell surface and wherein greater than fifty monoclonal antibody molecules are expressed and bound to the cell surface of the cells in the population that express monoclonal antibody.

Further provided by the present invention is a population of hybridoma cells wherein greater than 25% of the cells in the population express monoclonal antibody that is bound to the cell surface and wherein greater than twenty monoclonal antibody molecules are expressed and bound to the cell surface of the cells in the population that express monoclonal antibody.

The present invention also provides a population of hybridoma cells wherein greater than 25% of the cells in the population express monoclonal antibody that is bound to the cell surface and wherein greater than fifty monoclonal antibody molecules are expressed and bound to the cell surface of the cells in the population that express monoclonal antibody.

Also provided by the present invention is a hybridoma cell, wherein from about 0.01% to about 10% of the total amount of monoclonal antibody produced by the hybridoma cell is expressed and bound to the cell surface.

Also provided by the present invention is a population of hybridoma cells wherein greater than 15% of the hybridoma cells in the population express from about 0.01% to about 10% of the total amount of monoclonal antibody produced by the hybridoma cells on the cell surface.

Further provided by the present invention is a population of hybridoma cells wherein greater than 15% of the hybridoma cells in the population express from about 0.01% to about 10% of the total amount of monoclonal antibody produced by the hybridoma cells on the cell surface, and wherein greater than twenty monoclonal antibodies are expressed and bound to the cell surface.

Also provided by the present invention is a hybridoma cell comprising a vector, wherein the vector comprises a nucleic acid encoding at least one surface-expressed antibody receptor selected from the group consisting of Igα and Igfβ.

Further provided by the present invention is a hybridoma cell comprising a vector, wherein the vector comprises a nucleic acid encoding at least one surface-expressed antibody receptor selected from the group consisting of Igα and Igβ, wherein the nucleic acid is linked to an inducible functional expression sequence.

The present invention also provides a method for making a hybridoma cell comprising at least one surface-expressed antibody receptor selected from the group consisting of Igα and Id comprising fusing a myeloma cell comprising a vector, wherein the vector comprises a nucleic acid encoding at least one surface-expressed antibody receptor selected from the group consisting of Igα and Igβ, with a B cell to produce a hybridoma cell comprising at least one surface-expressed antibody receptor selected from the group consisting of Igα and Igβ.

The present invention also provides a B cell comprising a vector, wherein the vector comprises a nucleic acid encoding at least one surface-expressed antibody receptor selected from the group consisting of Igα and Igβ.

Also provided by the present invention is a B cell comprising a vector, wherein the vector comprises a nucleic acid encoding at least one surface-expressed antibody receptor selected from the group consisting of Igα and Igβ, wherein the vector comprises a nucleic acid encoding Igα and Igβ and wherein the vector is integrated into the genome of the B cell.

The present invention also provides a myeloma cell comprising at least one nucleic acid functionally encoding at least one surface-expressed antibody receptor selected from the group consisting of Igα and Igβ, wherein the nucleic acid encoding the surface-expressed antibody receptor is functionally linked to an inducible expression sequence.

Also provided by the present invention is a myeloma cell comprising at least one nucleic acid functionally encoding at least one mutated surface-expressed antibody receptor selected from the group consisting of Igα and Igβ, wherein the nucleic acid encoding the surface-expressed antibody receptor is functionally linked to an inducible expression sequence.

Also provided by the present invention is a method of making a monoclonal antibody of interest comprising: a) contacting a population of hybridoma cells wherein greater than 15% of the cells in the population express monoclonal antibody that is bound to the cell surface with an antigen linked to a detectable label, wherein the antigen binds to the monoclonal antibody to yield a detectably labeled hybridoma cell; b) isolating the detectably labeled hybridoma cell, thus identifying a hybridoma cell that produces the monoclonal antibody of interest; and c) making the monoclonal antibody of interest from the hybridoma cell.

Also provided by the present invention is a method of making a monoclonal antibody of interest comprising: a) contacting a population of hybridoma cells wherein greater than 15% of the cells in the population express monoclonal antibody that is bound to the cell surface with an antigen, wherein the antigen binds to the monoclonal antibody; b) adding a detectable label to the antigen to yield a detectably labeled hybridoma cell; c) isolating the detectably labeled hybridoma cell, thus identifying a hybridoma cell that produces the monoclonal antibody of interest; and d) making the monoclonal antibody of interest from the hybridoma cell.

Further provided by the present invention is a method of making a monoclonal antibody of interest comprising: a) contacting a hybridoma cell, wherein greater than twenty monoclonal antibody molecules are expressed and bound to the cell surface with an antigen linked to a detectable label, wherein the antigen binds to the monoclonal antibody to yield a detectably labeled hybridoma cell; b) isolating the detectably labeled hybridoma cell, thus identifying a hybridoma cell that produces the monoclonal antibody of interest; and c) making the monoclonal antibody of interest from the hybridoma cell.

Also provided by the present invention is a method of making a monoclonal antibody of interest comprising: a) contacting a hybridoma cell, wherein greater than twenty monoclonal antibody molecules are expressed and bound to the cell surface with an antigen, wherein the antigen binds to the monoclonal antibody; b) adding a detectable label to the antigen to yield a detectably labeled hybridoma cell; c) isolating the detectably labeled hybridoma cell, thus identifying a hybridoma cell that produces the monoclonal antibody of interest; and d) making the monoclonal antibody of interest from the hybridoma cell.

Also provided by the present invention is a method of making a monoclonal antibody of interest comprising: a) contacting a B cell comprising a vector, wherein the vector comprises a nucleic acid encoding at least one surface-expressed antibody receptor selected from the group consisting of Igα and Igβ with an antigen linked to a detectable label, wherein the antigen binds to the monoclonal antibody to yield a detectably labeled B cell; b) isolating the detectably labeled B cell, thus identifying a B cell that produces the monoclonal antibody of interest; and c) making the monoclonal antibody of interest.

The present invention also provides a method of making a monoclonal antibody of interest comprising: a) contacting a B cell comprising a vector, wherein the vector comprises a nucleic acid encoding at least one surface-expressed antibody receptor selected from the group consisting of Igα and Igβ with an antigen; b) adding a detectable label that binds to the antigen to yield a detectably labeled B cell; c) isolating the detectably labeled B cell, thus identifying a B cell that produces the monoclonal antibody of interest; and d) making the monoclonal antibody of interest.

Also provided is a method of making a hybridoma cell that produces a monoclonal antibody that recognizes a selected antigen comprising: a) immunizing a mouse with the antigen; b) fusing a B cell from the immunized mouse with a myeloma cell that comprises at least one nucleic acid functionally encoding at least one surface-expressed antibody receptor selected from the group consisting of Igα and Iβ to produce a monoclonal antibody producing hybridoma cell, wherein the monoclonal antibody produced by the hybridoma cell is expressed and bound to the cell surface; c) contacting the monoclonal antibody producing hybridoma cell with the antigen, wherein the antigen binds to the monoclonal antibody on the cell surface to produce a detectable hybridoma cell, d) detecting the hybridoma cell and; e) isolating the hybridoma cell, thus making a hybridoma cell that produces a monoclonal antibody that recognizes a specific antigen.

The present invention also provides a transgenic animal comprising B cells comprising a vector, wherein the vector comprises a nucleic acid encoding at least one surface-expressed antibody receptor selected from the group consisting of Igα and Igβ.

The present invention also provides a hematopoietic stem cell comprising a vector, wherein the vector comprises a nucleic acid encoding at least one surface-expressed antibody receptor selected from the group consisting of Igα and Igβ.

The invention further provides a population of hybridoma cells comprising a vector comprising a nucleic acid encoding Igα and/or Igβ that expresses monoclonal antibody bound to the cell surface, wherein when the monoclonal antibody is detected by fluorescence, the fluorescence intensity of at least 10% of the cells is at least two fold greater than a the fluorescence intensity of a population of hybridoma cells that do not comprise a vector comprising a nucleic acid encoding Igα and/or Igβ.

The present invention also provides a population of plasma cells comprising a vector comprising a nucleic acid encoding Igα and/or Igβ that expresses monoclonal antibody bound to the cell surface, wherein when the monoclonal antibody is detected by fluorescence the fluorescence intensity of the population of cells is at least two fold greater than the fluorescence intensity of a population of plasma cells that does not comprise a vector comprising a nucleic acid encoding Igα and/or Igβ.

The present invention also provides a population of hybridoma cells comprising a vector comprising a nucleic acid encoding Igα and/or Igβ that expresses monoclonal antibody bound to the cell surface, wherein when the monoclonal antibody is detected by fluorescence, the fluorescence intensity of at least 10% of the cells is at least two fold greater than a the fluorescence intensity of a population of hybridoma cells that do not comprise a vector comprising a nucleic acid encoding Igα and/or Iβ.

Further provided by the present invention a population of plasma cells comprising a vector comprising a nucleic acid encoding Igα and/or Igβ that expresses monoclonal antibody bound to the cell surface, wherein when the monoclonal antibody is detected by fluorescence the fluorescence intensity of at least 10% of the cells is at least two fold greater than the fluorescence intensity of a population of plasma cells that do not comprise a vector comprising a nucleic acid encoding Igα and/or Igβ.

BRIEF DESCRIPTION OF THE FIGURES

FIG. 3 shows the sequence of PCR modified mouse Igα cDNA extending from the HindIII to EcoRI cloning sites used to construct Igα expression plasmid p3.1NeoIgα. The Protein sequence is shown above the DNA sequence. The main DNA and protein sequence listings in GenBank for Igα have the accession numbers NM_007655 and NP_031681, respectively. The cDNA sequence obtained was inconsistent with this original Igα sequence in a small region, but agrees with the data given by Sakaguchi et al. ("B lymphocyte lineage-restricted expression of mb-1, a gene with CD3-like structural properties" *EMBO J.* 7:3457-64 (1988)) encoding a protein with the sequence encoding six amino acids listed in bold.

FIG. 4 shows the sequence of PCR modified mouse Igβ cDNA extending from the HindIII to EcoRI cloning sites used to construct Igβ expression plasmid p3.1NeoIgα. Protein sequence is shown above the DNA sequence. The main sequence listing in GenBank for Igβ has the accession number NM_008339.

FIG. 5 shows the structure of pcDNA3.1 NeoR vector (Invitrogen, Inc. Life Sciences Division) used to express Igα receptor protein in transgenic cells.

FIG. 6 shows the structure of pcDNA3.1 Zeo vector (Invitrogen, Inc. Life Sciences Division) used to express Igβ receptor protein in transgenic cells.

DETAILED DESCRIPTION OF THE INVENTION

Figure 1:
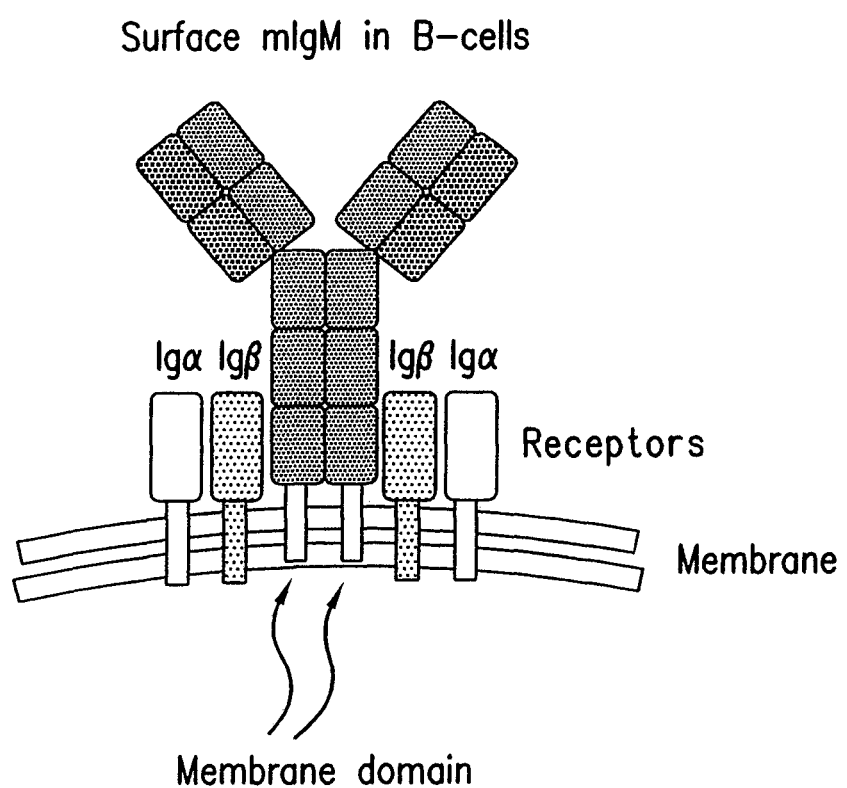
FIG. 1 shows that the surface presentation of antibody such as mIgM in B-cells requires the presence of one or two membrane receptors, Igα and/or Igβ. In B-cells these receptors bind the membrane domain of the membrane form of the heavy chain (mHC, dark gray) portion of an antibody such as mIgM. The small immunoglobulin light chain is drawn in black. In most myelomas the Igα (white) receptor shown here is missing or expressed at very low levels. In some myelomas Igα and/or Igβ may be absent or expressed at low levels. As a result, most hybridomas cannot present significant amounts of mIgM on their surface.

The present invention may be understood more readily by reference to the following detailed description of the preferred embodiments of the invention.

Before the present methods are disclosed and described, it is to be understood that this invention is not limited to specific constructs, molecules and methods, as such may of course, vary. It is also to be understood that the teiminology used herein is for the purpose of describing particular embodiments only and is not intended to be limiting.

It must be noted that, as used in the specification and the appended claims, the singular foams "a," "an," and "the" include plural referents unless the context clearly dictates otherwise. For example, a cell can mean a single cell or more than one cell.

Hybridomas

The present invention provides a population of hybridoma cells wherein greater than 15% of the cells in the population express monoclonal antibody that is bound to the cell surface. Also provided by this invention is a population of hybridoma cells wherein greater than 20%, 25%, 30%, 35%, 40%, 45%, 50%, 55%, 60%, 65%, 70%, 75%, 80%, 85%, 90%, 95% or numbers in between, of the cells in the population express monoclonal antibody that is bound to the cell surface.

As used herein, "hybridoma" is a cell or a cell line that is produced by fusing an antibody producing cell, e.g. a B cell, and an immortalized cell, e.g. a myeloma cell. As used herein "B cell" means an immature B cell, a mature naïve B cell, a mature activated B cell, a memory B cell, a B lineage lymphocyte, a plasma cell or any other B lineage cell of human origin or from non-human animal sources. The hybridomas of this invention can be made by fusing a B cell of human origin or from non-human animal sources, with an immortalized cell line using a suitable fusing agent, such as polyethylene glycol, to form a hybridoma cell (Goding, "Monoclonal Antibodies: Principles and Practice" Academic Press, (1986) pp. 59-103).

In order to obtain the B cells for the production of a hybridoma, a mouse or other appropriate host animal, is typically immunized with an immunizing agent or antigen to elicit B cells that produce or are capable of producing antibodies that will specifically bind to the immunizing agent or antigen. Alternatively, the B cells may be immunized in vitro. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, although HAT is not necessary for DISH, typically, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support high level expression of antibody by the selected antibody-producing cells, and are sensitive to a medium. The immortalized cell line can be sensitive to HAT medium. More preferred immortalized cell lines are murine myeloma lines, which can be obtained, for instance, from the Salk Institute Cell Distribution Center, San Diego, Calif. and the American Type Culture Collection (ATCC), Rockville, Md. Human myeloma and mouse-human heteromyeloma cell lines also have been described for the production of human monoclonal antibodies (Kozbor, J. Immunol., 133:3001 (1984) and Brodeur et al., "Monoclonal Antibody Production Techniques and Applications" Marcel Dekker, Inc., New York, (1987) pp. 51-63). For example, the following myeloma cell lines can be obtained from the ATCC: MOPC-31C, RPMI 8226, IM-9, MPC-11, CCL-189, HK-PEG-1, HS-Sultan, A2B5 clone 105, P3X63Ag8.653, Sp2/0-Ag14, Sp2/0-Ag14/SF, P3X63Ag8U.1, HFN 36.3 HFN 7.1, 45.6.TG1.7, ARH-77, Y3-Ag 1.2.3, SJK-132-20, SJK-287-38 and SJK-237-71.

The hybridoma cells of the present invention can be assayed for surface expression and the culture medium in which the hybridoma cells are cultured can be assayed for the presence of monoclonal antibodies directed against a desired immunogen by methods known in the art such as ELISA, western blot, FACS, magnetic separation etc. The binding specificity of monoclonal antibodies secreted by the hybridoma cells can be, for example, determined by immunoprecipitation or by an in vitro binding assay, such as radioimmunoassay (RIA) or enzyme-linked immunoabsorbent assay (ELISA). Such techniques and assays are known in the art.

The binding affinity of the monoclonal antibody can, for example, be determined by the Scatchard analysis of Munson et al., Anal. Biochem., 107:220 (1980).

After a desired hybridoma cell is identified, either by assaying surface expression or by assaying the culture medium, the selected hybridoma cell can be grown by standard methods. Suitable culture media for this purpose include, for example, Dulbecco's Modified Eagle's Medium and RPMI-1640 medium. Alternatively, the hybridoma cells may be grown in vivo as ascites in a mammal.

As used herein, "a population of hybridoma cells" means a sufficient number of cells such that a percentage of the cells expressing antibody can be determined. The hybridoma cells of the population can be cells from a pure hybridoma cell line where all of the cells of the line produce only one monoclonal antibody specific for a particular antigen or a mixture of cells wherein multiple monoclonal antibodies are produced. Thus, a population of hybridoma cells can produce more than one monoclonal antibody such that some cells produce a monoclonal antibody that recognize one antigen and other cells in the population produce monoclonal antibody that recognizes a second antigen and other cells in the population produce a monoclonal antibody that recognizes a third antigen etc.

As used herein, "express" means that the monoclonal antibody can be detected by means standard in the art such as Western blot, ELISA, immunofluorescence, hemolytic assay, fluorescence activated cell sorting (FACS) as they are currently practiced in the art.

Antibodies are typically proteins which exhibit binding specificity to a specific antigen. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain can have regularly spaced intrachain disulfide bridges. Each heavy chain can have at one end a variable domain (V(H)) followed by a number of constant domains. Each light chain can have a variable domain at one end (V(L)) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. The light chains of antibodies from any vertebrate species can be assigned to one of two clearly distinct types, called kappa (κ) and lambda (λ), based on the amino acid sequences of their constant domains. Depending on the amino acid sequence of the constant domain of their heavy chains, immunoglobulins can be assigned to different classes. There currently are five major classes of immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. The present invention provides the presentation of all of the immunoglobulin classes via binding to Ig α and/or Ig β. The heavy chain constant domains that correspond to the different classes of immunoglobulins are called alpha, delta, epsilon, gamma, and mu, respectively.

The Immunoglobulin (Ig) heavy chain genes are typically complex transcription units with multiple poly(A) sites in which changes in the cleavage and polyadenylation machinery can play an important role in B-cell, stage-specific expression. Ig u heavy chains can be expressed in pre, immature, and mature-B-cells and IgM+plasma cells. The α, ε, and γ heavy chains can be expressed in memory and IgA$^+$, IgE$^+$, and IgG+plasma cells, respectively (Janeway and Travers, 1994). RNA from each of the five classes of Ig heavy chain genes ($\alpha$, $\delta$, $\epsilon$, $\gamma$, $\mu$) can be alternatively processed to produce two types of mRNAs: one encodes the secreted form of the Ig protein and is produced by use of the promoter-proximal, weak Ig sec (secretory-specific) poly(A) site in plasma cells; the other mRNA encodes the membrane-bound (mb) receptor for antigen on the surface of mature or memory B-cells and can be produced by use of the downstream, strong Ig membrane poly(A) site [Alt, 1980; Rogers, 1980; Rogers, 1981].

There can be a 2-5-fold change in the transcription rate of the Ig genes in different B-cell stages (Kelly and Perry, 1986). The site of termination can vary in the $\mu$ (Galli et al., 1987; Guise et al., 1988; Yuan and Tucker, 1984) but not the $\gamma$ and $\alpha$ genes (Flaspohler et al., 1995; Flaspohler and Milcarek., 1990; Lehman et al., 1992). RNA processing events can play the major role in determining the ratios of the two forms of IgG heavy chain mRNA as first shown in 1985 (Milcarek and Hall, 1985). The crucial role for RNA processing has been further substantiated (See Edwalds-Gilbert and Milcarek, 1995; Edwalds-Gilbert and Milcarek, 1995; Flaspohler et al., 1995; Flaspohler and Milcarek., 1990; Genovese et al., 1991; Genovese and Milcarek, 1990; Hall and Milcarek, 1989; Kobrin et al., 1986; Lassman et al., 1992; Lassman and Milcarek, 1992; Matis et al., 1996; Milcarek et al., 1996). See also (Edwalds-Gilbert et al., 1997). Polyadenylation at the weak secretory-specific poly(A) site, which is promoter proximal to the membrane specific poly(A) site, and splicing to the membrane-specific exons at the sub-optimal splice site, in the last secretory-specific exon, can bemutually exclusive events. It has been shown that changes in the cleavage and polyadenylation of the precursor RNA tip the balance in plasma cells to the use of the first, weak poly(A) site.

The term "variable" is used herein to describe certain portions of the variable domains which differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains can each comprise four FR regions, largely adopting a $\beta$-sheet configuration, connected by three CDRs, which form loops connecting, and in some cases forming part of the $\beta$-sheet structure. The CDRs in each chain can be held together in close proximity by the FR regions and, with the CDRs from the other chain, contribute to the formation of the antigen binding site of antibodies (see Kabat E. A. et al., "Sequences of Proteins of Immunological Interest" National Institutes of Health, Bethesda, Md. (1987)). The constant domains are not typically involved directly in binding an antibody to an antigen, but exhibit various effector functions, such as participation of the antibody in antibody-dependent cellular toxicity.

As used herein, "monoclonal antibody" refers to an antibody that is produced by cells that are all derived from a single antibody-producing cell type and has a specific affinity for an antigen. Monoclonal antibodies are obtained from a substantially homogeneous population of antibodies, i.e., the individual antibodies comprising the population are identical except for possible naturally occurring mutations that may be present in minor amounts. The monoclonal antibodies secreted by the hybridoma cells of the present invention can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Once hybridomas are isolated by the present invention, the antibody coding regions of the hybridomas can be used to makemonoclonal antibodies by recombinant DNA methods, such as those described in U.S. Pat. No. 4,816,567 or U.S. Pat. No. 6,331,415. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody comprising one antigen-combining site having specificity for one antigen and second antigen-combining site having specificity for a different antigen.

The present invention also provides a hybridoma cell, wherein greater than twenty monoclonal antibody molecules are expressed and bound to the cell surface. Also provided by the present invention is a hybridoma cell, wherein greater than fifty monoclonal antibody molecules are expressed and bound to the cell surface. Further provided by the present invention is a hybridoma cell, wherein greater than one hundred monoclonal antibody molecules are expressed and bound to the cell surface. The present invention also provides a hybridoma cell, wherein greater than two hundred and fifty monoclonal antibody molecules are expressed and bound to the cell surface. Also provided by the present invention is a hybridoma cell, wherein greater than five hundred monoclonal antibody molecules are expressed and bound to the cell surface. Numbers of antibodies in between these numbers are also provided.

Further provided by the present invention is a population of hybridoma cells wherein greater than 15% of the cells in the population express monoclonal antibody that is bound to the cell surface and wherein greater than twenty monoclonal antibody molecules are expressed and bound to the cell surface of the cells in the population that express monoclonal antibody.

Also provided by the present invention is a population of hybridoma cells wherein greater than 15% of the cells in the population express monoclonal antibody that is bound to the cell surface and wherein greater than fifty monoclonal antibody molecules are expressed and bound to the cell surface of the cells in the population that express monoclonal antibody.

Further provided by the present invention is a population of hybridoma cells wherein greater than 15% of the cells in the population express monoclonal antibody that is bound to the cell surface and wherein greater than one hundred monoclonal antibody molecules are expressed and bound to the cell surface of the cells in the population that express monoclonal antibody.

The present invention also provides a population of hybridoma cells wherein greater than 15% of the cells in the population express monoclonal antibody that is bound to the cell surface and wherein greater than two hundred and fifty monoclonal antibody molecules are expressed and bound to the cell surface of the cells in the population that express monoclonal antibody.

Further provided by the present invention is a population of hybridoma cells wherein greater than 15% of the cells in the population express monoclonal antibody that is bound to the cell surface and wherein greater than five hundred monoclonal antibody molecules are expressed and bound to the cell surface of the cells in the population that express monoclonal antibody.

Further provided by the present invention is a population of hybridoma cells wherein greater than 25% of the cells in the population express monoclonal antibody that is bound to the cell surface and wherein greater than twenty monoclonal antibody molecules are expressed and bound to the cell surface of the cells in the population that express monoclonal antibody.

Also provided by the present invention is a population of hybridoma cells wherein greater than 25% of the cells in the population express monoclonal antibody that is bound to the cell surface and wherein greater than fifty monoclonal antibody molecules are expressed and bound to the cell surface of the cells in the population that express monoclonal antibody.

Further provided by the present invention is a population of hybridoma cells wherein greater than 25% of the cells in the population express monoclonal antibody that is bound to the cell surface and wherein greater than one hundred monoclonal antibody molecules are expressed and bound to the cell surface of the cells in the population that express monoclonal antibody.

The present invention also provides a population of hybridoma cells wherein greater than 25% of the cells in the population express monoclonal antibody that is bound to the cell surface and wherein greater than two hundred and fifty monoclonal antibody molecules are expressed and bound to the cell surface of the cells in the population that express monoclonal antibody.

Further provided by the present invention is a population of hybridoma cells wherein greater than 25% of the cells in the population express monoclonal antibody that is bound to the cell surface and wherein greater than five hundred monoclonal antibody molecules are expressed and bound to the cell surface of the cells in the population that express monoclonal antibody.

Further provided by the present invention is a population of hybridoma cells wherein greater than 50% of the cells in the population express monoclonal antibody that is bound to the cell surface and wherein greater than twenty monoclonal antibody molecules are expressed and bound to the cell surface of the cells in the population that express monoclonal antibody.

Also provided by the present invention is a population of hybridoma cells wherein greater than 50% of the cells in the population express monoclonal antibody that is bound to the cell surface and wherein greater than fifty monoclonal antibody molecules are expressed and bound to the cell surface of the cells in the population that express monoclonal antibody.

Further provided by the present invention is a population of hybridoma cells wherein greater than 50% of the cells in the population express monoclonal antibody that is bound to the cell surface and wherein greater than one hundred monoclonal antibody molecules are expressed and bound to the cell surface of the cells in the population that express monoclonal antibody.

The present invention also provides a population of hybridoma cells wherein greater than 50% of the cells in the population express monoclonal antibody that is bound to the cell surface and wherein greater than two hundred and fifty monoclonal antibody molecules are expressed and bound to the cell surface of the cells in the population that express monoclonal antibody.

Further provided by the present invention is a population of hybridoma cells wherein greater than 50% of the cells in the population express monoclonal antibody that is bound to the cell surface and wherein greater than five hundred monoclonal antibody molecules are expressed and bound to the cell surface of the cells in the population that express monoclonal antibody.

Further provided by the present invention is a population of hybridoma cells wherein greater than 75% of the cells in the population express monoclonal antibody that is bound to the cell surface and wherein greater than twenty monoclonal antibody molecules are expressed and bound to the cell surface of the cells in the population that express monoclonal antibody.

Also provided by the present invention is a population of hybridoma cells wherein greater than 75% of the cells in the population express monoclonal antibody that is bound to the cell surface and wherein greater than fifty monoclonal antibody molecules are expressed and bound to the cell surface of the cells in the population that express monoclonal antibody.

Further provided by the present invention is a population of hybridoma cells wherein greater than 75% of the cells in the population express monoclonal antibody that is bound to the cell surface and wherein greater than one hundred monoclonal antibody molecules are expressed and bound to the cell surface of the cells in the population that express monoclonal antibody.

The present invention also provides a population of hybridoma cells wherein greater than 75% of the cells in the population express monoclonal antibody that is bound to the cell surface and wherein greater than two hundred and fifty monoclonal antibody molecules are expressed and bound to the cell surface of the cells in the population that express monoclonal antibody.

Further provided by the present invention is a population of hybridoma cells wherein greater than 75% of the cells in the population express monoclonal antibody that is bound to the cell surface and wherein greater than five hundred monoclonal antibody molecules are expressed and bound to the cell surface of the cells in the population that express monoclonal antibody.

Further provided by the present invention is a population of hybridoma cells wherein greater than 90% of the cells in the population express monoclonal antibody that is bound to the cell surface and wherein greater than twenty monoclonal antibody molecules are expressed and bound to the cell surface of the cells in the population that express monoclonal antibody.

Also provided by the present invention is a population of hybridoma cells wherein greater than 90% of the cells in the population express monoclonal antibody that is bound to the cell surface and wherein greater than fifty monoclonal antibody molecules are expressed and bound to the cell surface of the cells in the population that express monoclonal antibody.

Further provided by the present invention is a population of hybridoma cells wherein greater than 90% of the cells in the population express monoclonal antibody that is bound to the cell surface and wherein greater than one hundred monoclonal antibody molecules are expressed and bound to the cell surface of the cells in the population that express monoclonal antibody.

The present invention also provides a population of hybridoma cells wherein greater than 90% of the cells in the population express monoclonal antibody that is bound to the cell surface and wherein greater than two hundred and fifty monoclonal antibody molecules are expressed and bound to the cell surface of the cells in the population that express monoclonal antibody.

Further provided by the present invention is a population of hybridoma cells wherein greater than 90% of the cells in the population express monoclonal antibody that is bound to the cell surface and wherein greater than five hundred monoclonal antibody molecules are expressed and bound to the cell surface of the cells in the population that express monoclonal antibody.

Also provided by the present invention is a hybridoma cell, wherein from about 0.001% to about 10% of the total amount of monoclonal antibody produced by the hybridoma cell is expressed and bound to the cell surface.

Any combinations of the above percentages of cells and number of antibodies per cell is also provided as well as numbers in between the specifically listed percentages of cell and number of antibodies per cell.

The total amount of monoclonal antibody produced by a cell can be determined by any of the standard methods in the art, including, but not limited to, Western blot, ELISA, immunofluorescence and FACS. These methods are utilized to measure the amount of antibody secreted into the medium by the cell, the amount of antibody bound to the cell surface and the amount of intracellular antibody present in the cells. One of skill in the art would know how to measure these amounts utilizing the above techniques or others known to the skilled artisan to obtain a total amount of antibody produced by a cell, such that a percentage of the total amount of antibody that is expressed and bound to the cell surface is obtained.

Also provided by the present invention is a hybridoma cell, wherein from about 0.01% to about 10% of the total amount of monoclonal antibody produced by the hybridoma cell is expressed and bound to the cell surface.

Also provided by the present invention is a hybridoma cell, wherein from about 10% to about 20% of the total amount of monoclonal antibody produced by the hybridoma cell is expressed and bound to the cell surface.

Also provided by the present invention is a hybridoma cell, wherein from about 20% to about 30% of the total amount of monoclonal antibody produced by the hybridoma cell is expressed and bound to the cell surface.

Also provided by the present invention is a hybridoma cell, wherein from about 30% to about 40% of the total amount of monoclonal antibody produced by the hybridoma cell is expressed and bound to the cell surface.

Also provided by the present invention is a hybridoma cell, wherein from about 40% to about 50% of the total amount of monoclonal antibody produced by the hybridoma cell is expressed and bound to the cell surface.

Also provided by the present invention is a hybridoma cell, wherein from about 50% to about 60% of the total amount of monoclonal antibody produced by the hybridoma cell is expressed and bound to the cell surface.

Also provided by the present invention is a hybridoma cell, wherein from about 60% to about 70% of the total amount of monoclonal antibody produced by the hybridoma cell is expressed and bound to the cell surface.

Also provided by the present invention is a hybridoma cell, wherein from about 70% to about 80% of the total amount of monoclonal antibody produced by the hybridoma cell is expressed and bound to the cell surface.

Also provided by the present invention is a hybridoma cell, wherein from about 80% to about 90% of the total amount of monoclonal antibody produced by the hybridoma cell is expressed and bound to the cell surface.

Also provided by the present invention is a hybridoma cell, wherein from about 90% to about 100% of the total amount of monoclonal antibody produced by the hybridoma cell is expressed and bound to the cell surface.

Further provided by the present invention is a population of hybridoma cells wherein greater than 15% of the hybridoma cells in the population express from about 0.01% to about 10% of the total amount of monoclonal antibody produced by the hybridoma cells on the cell surface. Also provided by this invention is a population of hybridoma cells wherein greater than 20%, 25%, 30%, 35%, 40%, 45%, 50%, 55%, 60%, 65%, 70%, 75%, 80%, 85%, 90%, or 95% of the hybridoma cells in the population express from about 0.01% to about 10% of the total amount of monoclonal antibody produced by the hybridoma cells on the cell surface.

Further provided by the present invention is a population of hybridoma cells wherein greater than 15% of the hybridoma cells in the population express from about 10% to about 20% of the total amount of monoclonal antibody produced by the hybridoma cells on the cell surface. Also provided by this invention is a population of hybridoma cells wherein greater than 20%, 25%, 30%, 35%, 40%, 45%, 50%, 55%, 60%, 65%, 70%, 75%, 80%, 85%, 90%, or 95% of the hybridoma cells in the population express from about 10% to about 20% of the total amount of monoclonal antibody produced by the hybridoma cells on the cell surface.

Further provided by the present invention is a population of hybridoma cells wherein greater than 15% of the hybridoma cells in the population express from about 20% to about 30% of the total amount of monoclonal antibody produced by the hybridoma cells on the cell surface. Also provided by this invention is a population of hybridoma cells wherein greater than 20%, 25%, 30%, 35%, 40%, 45%, 50%, 55%, 60%, 65%, 70%, 75%, 80%, 85%, 90%, or 95% of the hybridoma cells in the population express from about 20% to about 30% of the total amount of monoclonal antibody produced by the hybridoma cells on the cell surface.

Further provided by the present invention is a population of hybridoma cells wherein greater than 15% of the hybridoma cells in the population express from about 30% to about 40% of the total amount of monoclonal antibody produced by the hybridoma cells on the cell surface. Also provided by this invention is a population of hybridoma cells wherein greater than 20%, 25%, 30%, 35%, 40%, 45%, 50%, 55%, 60%, 65%, 70%, 75%, 80%, 85%, 90%, or 95% of the hybridoma cells in the population express from about 30% to about 40% of the total amount of monoclonal antibody produced by the hybridoma cells on the cell surface.

Further provided by the present invention is a population of hybridoma cells wherein greater than 15% of the hybridoma cells in the population express from about 40% to about 50% of the total amount of monoclonal antibody produced by the hybridoma cells on the cell surface. Also provided by this invention is a population of hybridoma cells wherein greater than 20%, 25%, 30%, 35%, 40%, 45%, 50%, 55%, 60° A, 65%, 70%, 75%, 80%, 85%, 90%, or 95% of the hybridoma cells in the population express from about 40% to about 50% of the total amount of monoclonal antibody produced by the hybridoma cells on the cell surface.

Further provided by the present invention is a population of hybridoma cells wherein greater than 15% of the hybridoma cells in the population express from about 50% to about 60% of the total amount of monoclonal antibody produced by the hybridoma cells on the cell surface. Also provided by this invention is a population of hybridoma cells wherein greater than 20%, 25%, 30%, 35%, 40%, 45%, 50%, 55%, 60%, 65%, 70%, 75%, 80%, 85%, 90%, or 95% of the hybridoma cells in the population express from about 50% to about 60% of the total amount of monoclonal antibody produced by the hybridoma cells on the cell surface.

Further provided by the present invention is a population of hybridoma cells wherein greater than 15% of the hybridoma cells in the population express from about 60% to about 70% of the total amount of monoclonal antibody produced by the hybridoma cells on the cell surface. Also provided by this invention is a population of hybridoma cells wherein greater than 20%, 25%, 30%, 35%, 40%, 45%, 50%, 55%, 60%, 65%, 70%, 75%, 80%, 85%, 90%, or 95% of the hybridoma cells in the population express from about 60% to about 70% of the total amount of monoclonal antibody produced by the hybridoma cells on the cell surface.

Further provided by the present invention is a population of hybridoma cells wherein greater than 15% of the hybridoma cells in the population express from about 70% to about 80% of the total amount of monoclonal antibody produced by the hybridoma cells on the cell surface. Also provided by this invention is a population of hybridoma cells wherein greater than 20%, 25%, 30%, 35%, 40%, 45%, 50%, 55%, 60%, 65%, 70%, 75%, 80%, 85%, 90%, or 95% of the hybridoma cells in the population express from about 70% to about 80% of the total amount of monoclonal antibody produced by the hybridoma cells on the cell surface.

Further provided by the present invention is a population of hybridoma cells wherein greater than 15% of the hybridoma cells in the population express from about 80% to about 90% of the total amount of monoclonal antibody produced by the hybridoma cells on the cell surface. Also provided by this invention is a population of hybridoma cells wherein greater than 20%, 25%, 30%, 35%, 40%, 45%, 50%, 55%, 60%, 65%, 70%, 75%, 80%, 85%, 90%, or 95% of the hybridoma cells in the population express from about 80% to about 90% of the total amount of monoclonal antibody produced by the hybridoma cells on the cell surface.

Further provided by the present invention is a population of hybridoma cells wherein greater than 15% of the hybridoma cells in the population express from about 90% to about 100% of the total amount of monoclonal antibody produced by the hybridoma cells on the cell surface. Also provided by this invention is a population of hybridoma cells wherein greater than 20%, 25%, 30%, 35%, 40%, 45%, 50%, 55%, 60%, 65%, 70%, 75%, 80%, 85%, 90%, or 95% of the hybridoma cells in the population express from about 90% to about 100% of the total amount of monoclonal antibody produced by the hybridoma cells on the cell surface.

Also provided by the present invention is a population Of hybridoma cells wherein greater than 15% of the hybridoma cells in the population express from about 0.01% to about 10% of the total amount of monoclonal antibody produced by the hybridoma cells on the cell surface, and wherein greater than twenty monoclonal antibodies are expressed and bound to the cell surface. Also provided by this invention is a population of hybridoma cells wherein greater than 20%, 25%, 30%, 35%, 40%, 45%, 50%, 55%, 60%, 65%, 70%, 75%, 80%, 85%, 90%, or 95% of the hybridoma cells in the population express from about 0.01% to about 10% of the total amount of monoclonal antibody produced by the hybridoma cells on the cell surface and wherein greater than 20%, 25%, 30%, 35%, 40%, 45%, 50%, 55%, 60%, 65%, 70%, 75%, 80%, 85%, 90%, or 95% of the population are hybridoma cells wherein greater than twenty monoclonal antibodies are expressed and bound to the cell surface.

Also provided by the present invention is a population of hybridoma cells wherein greater than 15% of the hybridoma cells in the population express from about 10% to about 20% of the total amount of monoclonal antibody produced by the hybridoma cells on the cell surface, and wherein greater than twenty monoclonal antibodies are expressed and bound to the cell surface. Also provided by this invention is a population of hybridoma cells wherein greater than 20%, 25%, 30%, 35%, 40%, 45%, 50%, 55%, 60%, 65%, 70%, 75%, 80%, 85%, 90%, or 95% of the hybridoma cells in the population express from about 10% to about 20% of the total amount of monoclonal antibody produced by the hybridoma cells on the cell surface and wherein greater than 20%, 25%, 30%, 35%, 40%, 45%, 50%, 55%, 60%, 65%, 70%, 75%, 80%, 85%, 90%, or 95% of the population are hybridoma cells wherein greater than twenty monoclonal antibodies are expressed and bound to the cell surface.

Also provided by the present invention is a population of hybridoma cells wherein greater than 15% of the hybridoma cells in the population express from about 20% to about 30% of the total amount of monoclonal antibody produced by the hybridoma cells on the cell surface, and wherein greater than twenty monoclonal antibodies are expressed and bound to the cell surface. Also provided by this invention is a population of hybridoma cells wherein greater than 20%, 25%, 30%, 35%, 40%, 45%, 50%, 55%, 60%, 65%, 70%, 75%, 80%, 85%, 90%, or 95% of the hybridoma cells in the population express from about 20% to about 30% of the total amount of monoclonal antibody produced by the hybridoma cells on the cell surface and wherein greater than 20%, 25%, 30%, 35%, 40%, 45%, 50%, 55%, 60%, 65%, 70%, 75%, 80%, 85%, 90%, or 95% of the population are hybridoma cells wherein greater than twenty monoclonal antibodies are expressed and bound to the cell surface.

Also provided by the present invention is a population of hybridoma cells wherein greater than 15% of the hybridoma cells in the population express from about 30% to about 40% of the total amount of monoclonal antibody produced by the hybridoma cells on the cell surface, and wherein greater than twenty monoclonal antibodies are expressed and bound to the cell surface. Also provided by this invention is a population of hybridoma cells wherein greater than 20%, 25%, 30%, 35%, 40%, 45%, 50%, 55%, 60%, 65%, 70%, 75%, 80%, 85%, 90%, or 95% of the hybridoma cells in the population express from about 30% to about 40% of the total amount of monoclonal antibody produced by the hybridoma cells on the cell surface and wherein greater than 20%, 25%, 30%, 35° A, 40%, 45%, 50%, 55%, 60%, 65%, 70%, 75%, 80%, 85%, 90%, or 95% of the population are hybridoma cells wherein greater than twenty monoclonal antibodies are expressed and bound to the cell surface.

Also provided by the present invention is a population of hybridoma cells wherein greater than 15% of the hybridoma cells in the population express from about 40% to about 50% of the total amount of monoclonal antibody produced by the hybridoma cells on the cell surface, and wherein greater than twenty monoclonal antibodies are expressed and bound to the cell surface. Also provided by this invention is a population of hybridoma cells wherein greater than 20%, 25%, 30%, 35%, 40%, 45%, 50%, 55%, 60%, 65%, 70%, 75%, 80%, 85%, 90%, or 95% of the hybridoma cells in the population express from about 40% to about 50% of the total amount of monoclonal antibody produced by the hybridoma cells on the cell surface and wherein, greater than 20%, 25%, 30%, 35%, 40%, 45%, 50%, 55%, 60%, 65%, 70%, 75%, 80%, 85%, 90%, or 95% of the population are hybridoma cells wherein greater than twenty monoclonal antibodies are expressed and bound to the cell surface.

Also provided by the present invention is a population of hybridoma cells wherein greater than 15% of the hybridoma cells in the population express from about 50% to about 60% of the total amount of monoclonal antibody produced by the hybridoma cells on the cell surface, and wherein greater than twenty monoclonal antibodies are expressed and bound to the cell surface. Also provided by this invention is a population of hybridoma cells wherein greater than 20%, 25%, 30%, 35%, 40%, 45%, 50%, 55%, 60%, 65%, 70%, 75%, 80%, 85%, 90%, or 95% of the hybridoma cells in the population express from about 50% to about 60% of the total amount of monoclonal antibody produced by the hybridoma cells on the cell surface and wherein greater than 20%, 25%, 30%, 35%, 40%, 45%, 50%, 55%, 60%, 65%, 70%, 75%, 80%, 85%, 90%, or 95% of the population are hybridoma cells wherein greater than twenty monoclonal antibodies are expressed and bound to the cell surface.

Also provided by the present invention is a population of hybridoma cells wherein greater than 15% of the hybridoma cells in the population express from about 60% to about 70% of the total amount of monoclonal antibody produced by the hybridoma cells on the cell surface, and wherein greater than twenty monoclonal antibodies are expressed and bound to the cell surface. Also provided by this invention is a population of hybridoma cells wherein greater than 20%, 25%, 30%, 35%, 40%, 45%, 50%, 55%, 60%, 65%, 70%, 75%, 80%, 85%, 90%, or 95% of the hybridoma cells in the population express from about 60% to about 70% of the total amount of monoclonal antibody produced by the hybridoma cells on the cell surface and wherein greater than 20%, 25%, 30%, 35%, 40%, 45%, 50%, 55%, 60%, 65%, 70%, 75%, 80%, 85%, 90%, or 95% of the population are hybridoma cells wherein greater than twenty monoclonal antibodies are expressed and bound to the cell surface.

Also provided by the present invention is a population of hybridoma cells wherein greater than 15% of the hybridoma cells in the population express from about 70% to about 80% of the total amount of monoclonal antibody produced by the hybridoma cells on the cell surface, and wherein greater than twenty monoclonal antibodies are expressed and bound to the cell surface. Also provided by this invention is a population of hybridoma cells wherein greater than 20%, 25%, 30%, 35%, 40%, 45%, 50%, 55%, 60%, 65%, 70%, 75%, 80%, 85%, 90%, or 95% of the hybridoma cells in the population express from about 70% to about 80% of the total amount of monoclonal antibody produced by the hybridoma cells on the cell surface and wherein greater than 20%, 25%, 30%, 35%, 40%, 45%, 50%, 55%, 60%, 65%, 70%, 75%, 80%, 85%, 90%, or 95% of the population are hybridoma cells wherein greater than twenty monoclonal antibodies are expressed and bound to the cell surface.

Also provided by the present invention is a population of hybridoma cells wherein greater than 15% of the hybridoma cells in the population express from about 80% to about 90% of the total amount of monoclonal antibody produced by the hybridoma cells on the cell surface, and wherein greater than twenty monoclonal antibodies are expressed and bound to the cell surface. Also provided by this invention is a population of hybridoma cells wherein greater than 20%, 25%, 30%, 35%, 40%, 45%, 50%, 55%, 60%, 65%, 70%, 75%, 80%, 85%, 90%, or 95% of the hybridoma cells in the population express from about 80% to about 90% of the total amount of monoclonal antibody produced by the hybridoma cells on the cell surface and wherein greater than 20%, 25%, 30%, 35%, 40%, 45%, 50%, 55%, 60%, 65%, 70%, 75%, 80%, 85%, 90%, or 95% of the population are hybridoma cells wherein greater than twenty monoclonal antibodies are expressed and bound to the cell surface.

Also provided by the present invention is a population of hybridoma cells wherein greater than 15% of the hybridoma cells in the population express from about 90% to about 100% of the total amount of monoclonal antibody produced by the hybridoma cells on the cell surface, and wherein greater than twenty monoclonal antibodies are expressed and bound to the cell surface. Also provided by this invention is a population of hybridoma cells wherein greater than 20%, 25%, 30%, 35%, 40%, 45%, 50%, 55%, 60%, 65%, 70%, 75%, 80%, 85%, 90%, or 95% of the hybridoma cells in the population express from about 90% to about 100% of the total amount of monoclonal antibody produced by the hybridoma cells on the cell surface and wherein greater than 20%, 25%, 30%, 35%, 40%, 45%, 50%, 55%, 60%, 65%, 70%, 75%, 80%, 85%, 90%, or 95% of the population are hybridoma cells wherein greater than twenty monoclonal antibodies are expressed and bound to the cell surface.

Also provided by the present invention is a population of hybridoma cells wherein greater than 15% of the hybridoma cells in the population express from about 0.01% to about 10% of the total amount of monoclonal antibody produced by the hybridoma cells on the cell surface, and wherein greater than 15% of the population are hybridoma cells wherein greater than fifty, one hundred, two hundred and fifty or five hundred monoclonal antibodies are expressed and bound to the cell surface. Also provided by this invention is a population of hybridoma cells wherein greater than 20%, 25%, 30%, 35%, 40%, 45%, 50%, 55%, 60%, 65%, 70%, 75%, 80%, 85%, 90%, or 95% of the hybridoma cells in the population express from about 0.01% to about 10% of the total amount of monoclonal antibody produced by the hybridoma cells on the cell surface and wherein greater than 20%, 25%, 30%, 35%, 40%, 45%, 50%, 55%, 60%, 65%, 70%, 75%, 80%, 85%, 90%, or 95% of the population are hybridoma cells wherein greater than fifty, one hundred, two hundred and fifty or five hundred monoclonal antibodies are expressed and bound to the cell surface.

Also provided by the present invention is a population of hybridoma cells wherein greater than 15% of the hybridoma cells in the population express from about 10% to about 20% of the total amount of monoclonal antibody produced by the hybridoma cells on the cell surface, and wherein greater than 15% of the population are hybridoma cells wherein greater than fifty, one hundred, two hundred and fifty or five hundred monoclonal antibodies are expressed and bound to the cell surface. Also provided by this invention is a population of hybridoma cells wherein greater than 20%, 25%, 30%, 35%, 40%, 45%, 50%, 55%, 60%, 65%, 70%, 75%, 80%, 85%, 90%, or 95% of the hybridoma cells in the population express from about 10% to about 20% of the total amount of monoclonal antibody produced by the hybridoma cells on the cell surface and wherein greater than 20%, 25%, 30%, 35%, 40%, 45%, 50%, 55%, 60%, 65%, 70%, 75%, 80%, 85%, 90%, or 95% of the population are hybridoma cells wherein greater than fifty, one hundred, two hundred and fifty or five hundred monoclonal antibodies are expressed and bound to the cell surface.

Also provided by the present invention is a population of hybridoma cells wherein greater than 15% of the hybridoma cells in the population express from about 20% to about 30% of the total amount of monoclonal antibody produced by the hybridoma cells on the cell surface, and wherein greater than 15% of the population are hybridoma cells wherein greater than fifty, one hundred, two hundred and fifty or five hundred monoclonal antibodies are expressed and bound to the cell surface. Also provided by this invention is a population of hybridoma cells wherein greater than 20%, 25%, 30%, 35%, 40%, 45%, 50%, 55%, 60%, 65%, 70%, 75%, 80%, 85%, 90%, or 95% of the hybridoma cells in the population express from about 20% to about 30% of the total amount of monoclonal antibody produced by the hybridoma cells on the cell surface and wherein greater than 20%, 25%, 30%, 35%, 40%, 45%, 50%, 55%, 60%, 65%, 70%, 75%, 80%, 85%, 90%, or 95% of the population are hybridoma cells wherein greater than fifty, one hundred, two hundred and fifty or five hundred monoclonal antibodies are expressed and bound to the cell surface.

Also provided by the present invention is a population of hybridoma cells wherein greater than 15% of the hybridoma cells in the population express from about 30% to about 40% of the total amount of monoclonal antibody produced by the hybridoma cells on the cell surface, and wherein greater than 15% of the population are hybridoma cells wherein greater than fifty, one hundred, two hundred and fifty or five hundred monoclonal antibodies are expressed and bound to the cell surface. Also provided by this invention is a population of hybridoma cells wherein greater than 20%, 25%, 30%, 35%, 40%, 45%, 50%, 55%, 60%, 65%, 70%, 75%, 80%, 85%, 90%, or 95% of the hybridoma cells in the population express from about 30% to about 40% of the total amount of monoclonal antibody produced by the hybridoma cells on the cell surface and wherein greater than 20%, 25%, 30%, 35%, 40%, 45%, 50%, 55%, 60%, 65%, 70%, 75%, 80%, 85%, 90%, or 95% of the population are hybridoma cells wherein greater than fifty, one hundred, two hundred and fifty or five hundred monoclonal antibodies are expressed and bound to the cell surface.

Also provided by the present invention is a population of hybridoma cells wherein greater than 15% of the hybridoma cells in the population express from about 40% to about 50% of the total amount of monoclonal antibody produced by the hybridoma cells on the cell surface, and wherein greater than 15% of the population are hybridoma cells wherein greater than fifty, one hundred, two hundred and fifty or five hundred monoclonal antibodies are expressed and bound to the cell surface. Also provided by this invention is a population of hybridoma cells wherein greater than 20%, 25%, 30%, 35%, 40%, 45%, 50%, 55%, 60%, 65%, 70%, 75%, 80%, 85%, 90%, or 95% of the hybridoma cells in the population express from about 40% to about 50% of the total amount of monoclonal antibody produced by the hybridoma cells on the cell surface and wherein greater than 20%, 25%, 30%, 35%, 40%, 45%, 50%, 55%, 60%, 65%, 70%, 75%, 80%, 85%, 90%, or 95% of the population are hybridoma cells wherein greater than fifty, one hundred, two hundred and fifty or five hundred monoclonal antibodies are expressed and bound to the cell surface.

Also provided by the present invention is a population of hybridoma cells wherein greater than 15% of the hybridoma cells in the population express from about 50% to about 60% of the total amount of monoclonal antibody produced by the hybridoma cells on the cell surface, and wherein greater than 15% of the population are hybridoma cells wherein greater than fifty, one hundred, two hundred and fifty or five hundred monoclonal antibodies are expressed and bound to the cell surface. Also provided by this invention is a population of hybridoma cells wherein greater than 20%, 25%, 30%, 35%, 40%, 45%, 50%, 55%, 60%, 65%, 70%, 75%, 80%, 85%, 90%, or 95% of the hybridoma cells in the population express from about 50% to about 60% of the total amount of monoclonal antibody produced by the hybridoma cells on the cell surface and wherein greater than 20%, 25%, 30%, 35%, 40%, 45%, 50%, 55%, 60%, 65%, 70%, 75%, 80%, 85%, 90%, or 95% of the population are hybridoma cells wherein greater than fifty, one hundred, two hundred and fifty or five hundred monoclonal antibodies are expressed and bound to the cell surface.

Also provided by the present invention is a population of hybridoma cells wherein greater than 15% of the hybridoma cells in the population express from about 60% to about 70% of the total amount of monoclonal antibody produced by the hybridoma cells on the cell surface, and wherein greater than 15% of the population are hybridoma cells wherein greater than fifty, one hundred, two hundred and fifty or five hundred monoclonal antibodies monoclonal antibodies are expressed and bound to the cell surface. Also provided by this invention is a population of hybridoma cells wherein greater than 20%, 25%, 30%, 35%, 40%, 45%, 50%, 55%, 60%, 65%, 70%, 75%, 80%, 85%, 90%, or 95% of the hybridoma cells in the population express from about 60% to about 70% of the total amount of monoclonal antibody produced by the hybridoma cells on the cell surface and wherein greater than 20%, 25%, 30%, 35%, 40%, 45%, 50%, 55%, 60%, 65%, 70%, 75%, 80%, 85%, 90%, or 95% of the population are hybridoma cells wherein greater than fifty, one hundred, two hundred and fifty or five hundred monoclonal antibodies are expressed and bound to the cell surface.

Also provided by the present invention is a population of hybridoma cells wherein greater than 15% of the hybridoma cells in the population express from about 70% to about 80% of the total amount of monoclonal antibody produced by the hybridoma cells on the cell surface, and wherein greater than 15% of the population are hybridoma cells wherein greater than fifty, one hundred, two hundred and fifty or five hundred monoclonal antibodies are expressed and bound to the cell surface. Also provided by this invention is a population of hybridoma cells wherein greater than 20%, 25%, 30%, 35%, 40%, 45%, 50%, 55%, 60%, 65%, 70%, 75%, 80%, 85%, 90%, or 95% of the hybridoma cells in the population express from about 70% to about 80% of the total amount of monoclonal antibody produced by the hybridoma cells on the cell surface and wherein greater than 20%, 25%, 30%, 35%, 40%, 45%, 50%, 55%, 60%, 65%, 70%, 75%, 80%, 85%, 90%, or 95% of the population are hybridoma cells wherein greater than fifty, one hundred, two hundred and fifty or five hundred monoclonal antibodies are expressed and bound to the cell surface.

Also provided by the present invention is a population of hybridoma cells wherein greater than 15% of the hybridoma cells in the population express from about 80% to about 90% of the total amount of monoclonal antibody produced by the hybridoma cells on the cell surface, and wherein greater than 15% of the population are hybridoma cells wherein greater than fifty, one hundred, two hundred and fifty or five hundred monoclonal antibodies are expressed and bound to the cell surface. Also provided by this invention is a population of hybridoma cells wherein greater than 20%, 25%, 30%, 35%, 40%, 45%, 50%, 55%, 60%, 65%, 70%, 75%, 80%, 85%, 90%, or 95% of the hybridoma cells in the population express from about 80% to about 90% of the total amount of monoclonal antibody produced by the hybridoma cells on the cell surface and wherein greater than 20%, 25%, 30%, 35%, 40%, 45%, 50%, 55%, 60%, 65%, 70%, 75%, 80%, 85%, 90%, or 95% of the population are hybridoma cells wherein greater than fifty, one hundred, two hundred and fifty or five hundred monoclonal antibodies are expressed and bound to the cell surface.

Also provided by the present invention is a population of hybridoma cells wherein greater than 15% of the hybridoma cells in the population express from about 90% to about 100% of the total amount of monoclonal antibody produced by the hybridoma cells on the cell surface, and wherein greater than 15% of the population are hybridoma cells wherein greater than fifty, one hundred, two hundred and fifty or five hundred monoclonal antibodies are expressed and bound to the cell surface. Also provided by this invention is a population of hybridoma cells wherein greater than 20%, 25%, 30%, 35%, 40%, 45%, 50%, 55%, 60%, 65%, 70%, 75%, 80%, 85%, 90%, or 95% of the hybridoma cells in the population express from about 90% to about 100% of the total amount of monoclonal antibody produced by the hybridoma cells on the cell surface and wherein greater than 20%, 25%, 30%, 35%, 40%, 45%, 50%, 55%, 60%, 65%, 70%, 75%, 80%, 85%, 90%, or 95% of the population are hybridoma cells wherein greater than fifty, one hundred, two hundred and fifty or five hundred monoclonal antibodies are expressed and bound to the cell surface.

Also provided by this invention is a population of hybridoma cells comprising monoclonal antibodies bound to the cell surface having about two, three, four, five, six, seven, eight, nine, ten times more antibody on the cell surface than control cells, i.e. standard hybridoma cells.

Further provided by this invention is a population of hybridoma cells comprising a vector comprising a nucleic acid encoding Igα and/or Igβ that expresses monoclonal antibody bound to the cell surface, wherein when the monoclonal antibody is detected by fluorescence, the fluorescence intensity of the population of cells is at least two fold greater than the fluorescence intensity of a population of hybridoma cells that do not comprise a vector comprising a nucleic acid encoding Igα and/or Igβ.

The invention also provides a population of hybridoma cells comprising a vector comprising a nucleic acid encoding Igα and/or Igβ that expresses monoclonal antibody bound to the cell surface, wherein when the monoclonal antibody is detected by fluorescence, the fluorescence intensity of the population of cells is at least two fold, three fold, four fold, five fold, six fold, seven fold, eight fold, nine fold, ten fold, fifteen fold, twenty fold, thirty fold, forty fold, fifty fold, sixty fold, seventy fold, eighty fold, ninety fold, one hundred fold, two hundred and fifty fold, five hundred fold or one thousand fold greater than the fluorescence intensity of a population of hybridoma cells that do not comprise a vector comprising a nucleic acid encoding Igα and/or Igβ. The fold increase in fluorescence intensity can also be any amount in between the fold increases listed above. The fold increase in fluorescence intensity can be measured by methods standard in the art and is described herein in the Examples.

The population of hybridoma cells utilized to measure fluorescence intensity can be between 25 and 500 cells. Therefore, the population can be about 25, 50, 75, 100, 125, 150, 175, 200, 225, 250, 275, 300, 325, 350, 375, 400, 425, 450, 475, 500 cells or any number of cells in between these values.

The hybridomas in the population can comprise a vector comprising a nucleic acid encoding Igα.

Further provided by the present invention is a population of hybridoma cells comprising a vector comprising a nucleic acid encoding Igα and/or Igβ that expresses monoclonal antibody bound to the cell surface, wherein when the monoclonal antibody is detected by fluorescence, the fluorescence intensity of at least 10% of the cells is at least two fold greater than the fluorescence intensity of a population of hybridoma cells that do not comprise a vector comprising a nucleic acid encoding Igα and/or Igβ.

The present invention also provides a population of hybridoma cells comprising a vector comprising a nucleic acid encoding Igα and/or Igβ that expresses monoclonal antibody bound to the cell surface, wherein when the monoclonal antibody is detected by fluorescence, the fluorescence intensity of at least 20%, 30%, 40%, 50%, 60%, 70%, 80%, 90%, 100% or any percentage in between of the cells is at least two fold greater than the fluorescence intensity of a population of hybridoma cells that do not comprise a vector comprising a nucleic acid encoding Igα and/or Igβ.

The present invention also provides a population of hybridoma cells comprising a vector comprising a nucleic acid encoding Igα and/or Igβ that expresses monoclonal antibody bound to the cell surface, wherein when the monoclonal antibody is detected by fluorescence, the fluorescence intensity of at least 10%, 20%, 30%, 40%, 50%, 60%, 70%, 80%, 90%, 100% or any percentage in between of the cells is at least two fold, three fold, five fold, six fold, seven fold, eight fold, nine fold, ten fold, twenty fold, thirty fold, forty fold, fifty fold, sixty fold, seventy fold, eight fold, ninety fold, one hundred fold, two hundred and fifty fold, five hundred fold, one thousand fold or any amount in between, greater than the fluorescence intensity of a population of hybridoma cells that do not comprise a vector comprising a nucleic acid encoding Igα and/or Igβ.

Further provided by the present invention is a hybridoma cell comprising a vector, wherein the vector comprises a nucleic acid encoding at least one surface-expressed antibody receptor selected from the group consisting of Igα and Igβ. Therefore, the hybridoma can comprise a vector comprising a nucleic acid encoding Igα, or the hybridoma can comprise a vector comprising a nucleic acid encoding Id, or the hybridoma can comprise a vector comprising a nucleic acid encoding both Igα and a nucleic acid encoding Igβ. The nucleic acids encoding Igα or Igβ can be present in a single vector or in multiple vectors. For example, the hybridoma can comprise a vector comprising a nucleic acid encoding Igβ and a vector comprising a nucleic acid encoding Igβ or a vector comprising the nucleic acid sequences for both Igα and Igβ. Any of the vectors can be integrated into the genome of the cell or carried extrachromosomally to allow transient expression of Igα and/or Igβ.

As used herein, the term "nucleic acid" refers to single- or multiple stranded molecules which may be DNA or RNA, or any combination thereof, including modifications to those nucleic acids. The nucleic acid may represent a coding strand or its complement, or any combination thereof. Nucleic acids may be identical in sequence to the sequences which are naturally occurring for the Igα and Igβ receptors discussed herein or may include alternative codons which encode the same amino acid as that which is found in the naturally occurring sequence. Also contemplated are nucleic acid sequences encoding Igα and Igβ that contain deletions, substitutions, mutations and combinations thereof as long as the nucleic acid encodes a functional receptor. These nucleic acids can also be modified from their typical structure. Such modifications include, but are not limited to, methylated nucleic acids, the substitution of a non-bridging oxygen on the phosphate residue with either a sulfur (yielding phosphorothioate deoxynucleotides), selenium (yielding phosphorselenoate deoxynucleotides), or methyl groups (yielding methylphosphonate deoxynucleotides).

The nucleic acid sequence for the Igα receptor is available from GenBAnk via Accession No. NM_007655 and the polypeptide encoded by this nucleic acid sequence is available from GenBank via Accession Number NP_031681. The nucleic acid sequence encoding Igα that was utilized in the Examples described herein differs from the original Igα receptor available from GenBAnk via Accession No. NM_007655, but is consistent with the sequence provided by Sakaguchi et al. This sequence is provided in FIG. 3.

A nucleic acid molecule encoding Igα and a nucleic acid encoding Igβ can be isolated from the organism in which it is normally found. For example, a genomic DNA or cDNA library can be constructed and screened for the presence of the nucleic acid of interest. Methods of constructing and screening such libraries are well known in the art and kits for performing the construction and screening steps are commercially available (for example, Stratagene Cloning Systems, La Jolla, Calif.). Once isolated, the nucleic acid can be directly cloned into an appropriate vector, or if necessary, be modified to facilitate the subsequent cloning steps. Such modification steps are routine, an example of which is the addition of oligonucleotide linkers which contain restriction sites to the termini of the nucleic acid. General methods are set forth in Sambrook et al., "Molecular Cloning, a Laboratory Manual," Cold Spring Harbor Laboratory Press (1989).

Once the nucleic acid sequence of the desired Igα and/or Igβ is obtained, the sequence encoding specific amino acids can be modified or changed at any particular amino acid position by techniques well known in the art. For example, PCR primers can be designed which span the amino acid position or positions and which can substitute any amino acid for another amino acid. Then a nucleic acid can be amplified and inserted into the wild-type receptor coding sequence in order to obtain any of a number of possible combinations of amino acids at any position of the receptors. Alternatively, one skilled in the art can introduce specific mutations at any point in a particular nucleic acid sequence through techniques for point mutagenesis. General methods are set forth in Smith, M. "In vitro mutagenesis" Ann. Rev. Gen., 19:423-462 (1985) and Zoller, M. J. "New molecular biology methods for protein engineering" Curr. Opin. Struct. Biol., 1:605-610 (1991). Techniques such as these can be used to alter the coding sequence without altering the amino acid sequence that is encoded.

Another example of a method of obtaining a DNA molecule encoding Igα is to synthesize a recombinant DNA molecule which encodes Igα. A nucleic acid encoding Iβ, can also be obtained in this manner. For example, oligonucleotide synthesis procedures are routine in the art and oligonucleotides coding for a particular protein region are readily obtainable through automated DNA synthesis. A nucleic acid for one strand of a double-stranded molecule can be synthesized and hybridized to its complementary strand. One can design these oligonucleotides such that the resulting double-stranded molecule has either internal restriction sites or appropriate 5' or 3' overhangs at the termini for cloning into an appropriate vector. Double-stranded molecules coding for relatively large proteins can readily be synthesized by first constructing several different double-stranded molecules that code for particular regions of the protein, followed by ligating these DNA molecules together. For example, Cunningham, et al., "Receptor and Antibody Epitopes in Human Growth Hormone Identified by Homolog-Scanning Mutagenesis," Science, 243:1330-1336 (1989), have constructed a synthetic gene encoding the human growth hormone gene by first constructing overlapping and complementary synthetic oligonucleotides and ligating these fragments together. See also, Ferretti, et al., Proc. Nat. Acad. Sci. 82:599-603 (1986), wherein synthesis of a 1057 base pair synthetic bovine rhodopsin gene from synthetic oligonucleotides is disclosed. By constructing a nucleic acid in this manner, one skilled in the art can readily obtain any particular Igα or Igβ with desired amino acids at any particular position or positions within the Igα or Igβ. See also, U.S. Pat. No. 5,503,995 which describes an enzyme template reaction method of making synthetic genes. Techniques such as this are routine in the art and are well documented. These nucleic acids or fragments of a nucleic acid encoding Igα or Igβ can then be expressed in vivo or in vitro as discussed below. Similarly, nucleic acids or fragments of a nucleic acid encoding can be expressed in vivo or in vitro.

Once a nucleic acid encoding Igα or a region of that nucleic acid, is constructed, modified, or isolated, that nucleic acid can then be cloned into an appropriate vector, which can direct the in vivo or in vitro synthesis of that wild-type and/or modified Igα receptor protein. Also, once a nucleic acid encoding Igβ or a region of that nucleic acid, is constructed, modified, or isolated, that nucleic acid can then be cloned into an appropriate vector, which can direct the in vivo or in vitro synthesis of that wild-type and/or modified Igβ receptor protein. The vector is contemplated to have the necessary functional elements that direct and regulate transcription of the inserted gene, or nucleic acid. These functional elements include, but are not limited to, a promoter, regions upstream or downstream of the promoter, such as enhancers that may regulate the transcriptional activity of the promoter, an origin of replication, appropriate restriction sites to facilitate cloning of inserts adjacent to the promoter, antibiotic resistance genes or other markers which can serve to select for cells containing the vector or the vector containing the insert, RNA splice junctions, a transcription teiinination region, or any other region which may serve to facilitate the expression of the inserted gene or hybrid gene. (See generally, Sambrook et al.). One could also transfect DNA or RNA encoding an extra copy of Igα and/or Igβ directly into the cell in the absence of additional functional elements, e.g. as naked DNA or RNA, as long as the Igα and/or Igβ resulted in increased expression of the receptor.

The vector comprising a nucleic acid encoding Igα and Igβ of the present invention can be any vector suitable for expression of a nucleic acid in a eukaryotic cell as are known in the art. For example, pcDNA3.1 NeoR vector or pcDNA 3.1 Zeo can be utilized (Invitrogen, Inc. Life Sciences Division). Other vectors include, but are not limited to, a two vector inducible system from Invitrogen (pIND and pVgRXR plasmids), a two vector inducible system from Clontech (pTet-ON or pTet-Off and pTRE2 plasmids), single plasmids for constitutive expression from Promega (pCI or pSI plasmids), a two vector inducible system from Stratagene (pCMVLacI and pOPRSVI/MCS plasmids), single plasmid inducible systems from Stratagene (pERV3 or pEGSH plasmids) and single retroviral inducible systems from Stratagene (pCFB-EGSH or pFB-ERV retroviral vectors). The vector can also be a viral vector such as an adenoviral vector, an adeno-associated viral vector, a retroviral vector, a lentiviral vector, a pseudotyped retroviral vector, or a pox virus vector, such as a vaccinia virus vector.

The present invention also provides a hybridoma cell comprising a vector, wherein the vector comprises a nucleic acid encoding at least one mutated surface-expressed antibody receptor selected from the group consisting of Igα and Igβ. Thus, the present invention provides a hybridoma cell comprising a vector that comprises a nucleic acid encoding a mutant Igα receptor, a hybridoma cell comprising a vector that comprises a nucleic acid encoding a mutant Igβ receptor, and a hybridoma cell that comprises a vector that comprises both a nucleic acid encoding mutant Igα receptor and a nucleic acid encoding a mutant Igβ receptor.

The mutant Igα and Igβ receptors include non-signalling receptors with altered cytoplasmic domains. An example of such a mutant receptor is an Igα receptor comprising mutations at amino acid residues 176, 182, 193 and 204. The mutated Igαreceptors of the present invention also include a mutated Igα that comprises one or more mutations selected from the group consisting of Y176F, Y182F, Y193F and Y204F. Further provided by the present invention is a mutated Igα receptor that comprises a deletion of amino acid residues 176-220. Another example of a mutant surface expressed antibody receptor is a mutated Igβ receptor comprising mutations at amino acid residues 190 and 206. The mutated Igβ receptors of the present invention also include a mutated Igβ receptor comprising one or more mutations selected from the group consisting of Y190F and Y206F. The mutations described herein for the Igα and the Igβ are designed such that the receptors retain the ability to bind antibodies, but are unable to act as signaling receptors. One of skill in the art would know how to manipulate the nucleic acids encoding Igα and Igβ as described above as well as other techniques known in the art to obtain the mutant receptors described herein as well as other mutant receptors.

Also provided by the present invention is a hybridoma cell comprising a vector, wherein the vector comprises a nucleic acid encoding at least one chimeric surface-expressed antibody receptor selected from the group consisting of Igα and Igβ. As used throughout this application, "chimeric" means that the cell surface receptor can comprise a sequence derived from a receptor sequence of one species, e.g. human, and a receptor sequence derived from another species. For example, a chimeric Igα can comprise a human Igα extracellular domain and a mouse Igα transmembrane domain and mouse intracellular (cytoplasmic) domain or a chimeric Igα can comprise a human Igα extracellular domain and a human transmembrane domain and a mouse intracellular domain. Similarly, a chimeric Igβ can comprise a human Igβ extracellular domain and a mouse Igβ transmembrane and mouse intracellular domain or a chimeric Igβ can comprise a human Igβ extracellular domain and a human Igβ transmembrane and a mouse intracellular domain. Receptor sequences from other species such as chicken, dog, rabbit, rat, gerbil and hamster can also be utilized to make the chimeric receptors of the present invention. Other examples of chimeric receptors include, but are not limited to a chimeric Igα or Igβ receptor comprising a rabbit N-terminal extracellular domain, a mouse transmembrane domain and a mouse C-terminal intracellular domain; a chimeric receptor comprising a chicken N-terminal domain, a mouse transmembrane domain and a mouse C-terminal domain; a chimeric receptor comprising a mouse N-teiniinal extracellular domain, a chicken transmembrane domain and a chicken C-terminal intracellular signaling domain; a chimeric receptor comprising a mouse N-terminal extracellular domain, a rabbit transmembrane domain and a human C-terminal intracellular signaling domain; a chimeric receptor comprising a mouse N-terminal extracellular domain a human transmembrane domain and a mutant C-terminal intracellular non-signaling domain from mouse."

The chimeric receptors of this invention also include chimeric receptors comprising a sequence derived from Igα or Igβ and another non-related sequence. For example, the present invention contemplates a chimeric Igα receptor comprising an extracellular domain from a non-related protein, such as CD8 or any other protein with an extracellular domain and a transmembrane Igα domain and an intracellular Igα-domain.

The present invention further provides a hybridoma cell comprising a vector, wherein the vector comprises a nucleic acid encoding at least one surface-expressed antibody receptor selected from the group consisting of Igα and Igβ, wherein the nucleic acid is linked to an inducible functional expression sequence.

All of the sequences encoding Igα and Igβ can be functionally linked to an expression sequence. The expression sequences can include a promoter, an enhancer, a silencer and necessary information processing sites, such as ribosome binding sites, RNA splice sites, polyadenylation sites and transcriptional terminator sequences. The promoters utilized can be constitutive promoters or inducible promoters.

The inducible expression systems that can be used for the compositions and methods of the present invention include the IPTG based regulatory system, a tetracycline based regulatory system, CID based regulatory system, an ecdysone based regulatory system, and an estrogen-based regulatory system. Burcin et al., "A Regulatory System for Target Gene Expression" *Frontiers in Bioscience*, 3:1-7 (1998) describes these systems in detail and is incorporated herein in its entirety for the purposes of describing these inducible expression systems. Another inducible system that can be utilized is the cre-lox system (See Lakso "Targeted oncogene activation by site-specific recombination in transgenic mice." *Proc. Natl Acad Sci USA* 89: 6861-65 (1992); Orban et al., "Tissue and site-specific DNA recombination in transgenic mice" *Proc Natl Acad Sci USA* 90: 6861-65 (1992); Gu et al., "Deletion of a DNA polymerase beta gene segment in T cells using cell type-specific gene targeting" *Science* 265: 103-106 (1994)). The nucleic acids of the present invention can also be under the control of an inducible metallothionine promoter (See Cox and Maness "Neurite extension and protein tyrosine phosphorylation elicited by inducible expression of the v-src oncogene in a PC12 cell line" Exp Cell Res 195: 423-31 (1991)).

In addition to comprising vectors comprising a nucleic acid encoding at least one surface expressed antibody receptor selected from the group consisting of Igα and Igβ, the hybridomas of the present invention can also comprise a vector comprising a nucleic acid encoding U1A, an enzyme involved in inhibiting the expression of the secretory form of immunoglobulin M (See Philips et al., "Regulation of nuclear poly (A) addition controls the expression of immunoglobulin M secretory mRNA, *EMBO* 22:6443-6452 (2001).

All of the hybridoma cells described in this application can be utilized in the methods described herein to make a monoclonal antibody of interest.

Methods of Making Hybridomas

Also provided by the present invention is a method for making a hybridoma cell comprising at least one surface-expressed antibody receptor selected from the group consisting of Igα and 10 comprising fusing a myeloma cell comprising a vector, wherein the vector comprises a nucleic acid encoding at least one surface-expressed antibody receptor selected from the group consisting of Igα and/or Igβ, with a B cell to produce a hybridoma cell comprising at least one surface-expressed antibody receptor selected from the group consisting of Igα and Igβ.

In the methods of making the hybridoma cells of the present invention, the vector can integrate into the genome of the cell. The vector may also be carried extrachromosomally in the cell, thus allowing transient expression of Igα and Igβ. In the methods of making the hybridomas of the present invention, the nucleic acids encoding Igα and Igβ can be functionally linked to an inducible expression sequence. Inducible expression systems are discussed above.

The myeloma cells of the present invention can comprise at least one nucleic acid functionally encoding at least one surface-expressed antibody receptor selected from the group consisting of Igα and Igβ, wherein the nucleic acid encoding the surface-expressed antibody receptor is functionally linked to an inducible expression sequence. The myeloma cells of the present invention can also comprise a nucleic acid encoding a mutated Igα receptor and/or a mutated Igβ receptor. An example of such a mutant receptor is an Igα receptor comprising mutations at amino acid residues 176, 182, 193 and 204. The mutated Igα receptors of the present invention also include a mutated Igα that comprises one or more mutations selected from the group consisting of Y176F, Y182F, Y193F and Y204F. Further provided by the present invention is a myeloma cell comprising a nucleic acid encoding a mutated Igα receptor that comprises a deletion of amino acid residues 176-220. Another example of a mutant surface expressed antibody receptor is a mutated Igβ receptor comprising mutations at amino acid residues 190 and 206. The mutated Igβ receptors of the present invention also include a mutated Igβ receptor comprising one or more mutations selected from the group consisting of Y190F and Y206F. The myeloma cell of the present invention can be a myeloma cell comprising a vector that encodes a mutant Igα receptor, a myeloma cell comprising a vector that comprises a mutant Igβ receptor, or a myeloma cell that comprises a mutant Igα receptor and a mutant Igβ receptor.

The myeloma cell utilized in the methods of the present invention can also comprise a nucleic acid encoding a chimeric Igα receptor and/or a chimeric Igβ receptor.

B Cells

The present invention also provides a B cell comprising a vector, wherein the vector comprises a nucleic acid encoding at least one surface-expressed antibody receptor selected from the group consisting of Igα and Igβ. Therefore, the B cells of this invention can comprise a vector comprising a nucleic acid encoding Igα, or a vector comprising a nucleic acid encoding Igβ, or a vector comprising a nucleic acid encoding both Igα and Igf3.

The B cells of the present invention can also comprise a vector comprising a nucleic acid encoding a mutated Igα receptor and/or a mutated Igβ receptor. An example of such a mutant receptor is an Igα receptor comprising mutations at amino acid residues 176, 182, 193 and 204. The mutated Igα receptors of the present invention also include a mutated Igα that comprises one or more mutations selected from the group consisting of Y176F, Y182F, Y193F and Y204F. Further provided by the present invention is a B cell comprising a vector comprising a nucleic acid encoding a mutated Igα receptor that comprises a deletion of amino acid residues 176-220. Another example of a mutant surface expressed antibody receptor is a mutated Igβ receptor comprising mutations at amino acid residues 190 and 206. The mutated Id receptors of the present invention also include a mutated Igβ receptor comprising one or more mutations selected from the group consisting of Y190F and Y206F. The B cell of the present invention can be a B cell comprising a vector that encodes a mutant Igαreceptor, a B cell comprising a vector that encodes a mutant Igβ receptor, or a B cell that comprises a vector encoding a mutant Igα receptor and a mutant Igβ receptor.

The B cells of the present invention can also comprise a nucleic acid encoding a chimeric Igα receptor and/or a chimeric Igβ receptor.

The present invention also provides a B cell comprising a vector, wherein the vector comprises a nucleic acid encoding Igα and Igβ, wherein the nucleic acid encoding Igα and Igβ is functionally linked to an inducible expression sequence and wherein the nucleic acid encoding Igα and Igβ is integrated into the genome of the cell. Such a B cell can be obtained from the transgenic animals described herein.

The present invention also provides a method of making a B cell comprising a vector, wherein the vector comprises a nucleic acid encoding at least one surface-expressed antibody receptor selected from the group consisting of Igα and Igβ comprising the steps of transfecting a B cell with a vector comprising at least one nucleic acid functionally encoding at least one surface-expressed antibody receptor selected from the group consisting of Igα and Igβ, wherein the nucleic acid encoding the surface-expressed antibody receptor is functionally linked to an expression sequence. In the methods of making the B cells of the present invention, the nucleic acids encoding Igα and Igβ can be functionally linked to an inducible expression sequence. In the methods of making the B cells of the present invention, the vector comprising at least one nucleic acid functionally encoding at least one surface-expressed antibody receptor selected from the group consisting of Igα and Igβ can be integrated into the genome of the B cell. Alternatively, the vector does not integrate into the genome of the cell and the vector is carried extrachromosomally to allow transient expression of Igα and/or Igβ.

The vectors of the present invention can be transfected into cells using any technique known in the art. For example, lipofectamine transfection, microinjection, electroporation, liposomal delivery and particle gun bombardment can all be utilized to effect vector delivery to cells.

In order to transfect B cells removed from an animal's spleen, B cells can be propagated for 24-48 hours in culture so that they divide. A retroviral vector comprising a nucleic acid encoding comprising at least one nucleic acid functionally encoding at least one surface-expressed antibody receptor selected from the group consisting of Igα and Igβ can then be transfected into the cells. In order to promote proliferation, cytokines can be added to the culture. Cytokines that can be utilized in these methods include, but are not limited to, IL-2, IL-4, IL-5, IL-6, IFN-γ, and/or TGF-13. B cells that produce antibodies bound to their cell surface can then be detected by methods known in the art and described herein, such as FACS, cell panning, ELISA etc. Alternatively, a viral vector such as an adenoviral vector, a lentiviral vector, an adeno-associated vector, a vaccinia virus vector, a pseudotyped retroviral vector can be utilized to transfect B cells. One of skill in the art would know how to test B cells for their ability to be transfected by a vector and select the vector that is most suitable for the introduction of nucleic acids into these cells. One of skill in the art can also engineer the B cells of the present invention to produce a cell surface receptor that would be recognized by a particular vector. For example, the B cells of the present invention could be engineered such that a cell-surface receptor for adenovirus is present on the cell surface of the B cells in order to facilitate entry of the adenoviral vector into the B cells. Alternatively, a viral vector comprising a ligand that binds to a receptor (other than Igβ and Igβ) that has been introduced into the B cell can also be utilized to effect vector transfer. The presence of these cell surface receptors can be controlled by an inducible expression system described herein or elsewhere in the art, such that after transfection, expression of the cell surface receptor necessary for viral entry is no longer induced and thus the receptor is no longer expressed on the cell surface of the B cell. These B cells can then be fused to an immortalized cell, such as a naturally occurring myeloma or a genetically altered myeloma cell, such as those provided herein to make a hybridoma cell line expressing a monoclonal antibody of interest. Alternatively the amino acid sequence of the antibody or desired portion thereof, such as a variable region made by such B cell, or the nucleic acid (cDNA) that codes for such antibody or portion thereof, may be determined or isolated. Such DNA sequence may then be incorporated into a vector which directs the expression and secretion of such antibody and such vector transfected into a host cell. such as a myeloma or other appropriate immortal cell. Techniques for determining transfecting and expressing such antibody sequences are described in U.S. Pat. No. 5,627,052 and U.S. Pat. No. 6,331,415.

The B cells of the present invention can further comprise a detectable label.

The present invention also provides an immortalized B cell made by transfecting the B cell with a nucleic acid encoding telomerase. (See Bunk "Immortalizing Human Cells, *The Scientist* 14:19 (2000)). Immortalized B cells can also be made be inactivating pRB/p16 (INK4a) in addition to enhanced telomerase expression (See Kiyono et al., 1998; Dickson et al., 2000). Furtheimore, immortalized cells can be made by overexpressing c-myc and simian virus 40 large T antigen (Greenberg et al., 1999; Kim et al., 2001). Immortalized B cells can also be made by overexpressing Cyclin D1 and inactivating p 53 (See Opitz et al., 2001) or by overexpressing SV40 large T antigen alone (Russo et al., 1998). Other methods of immortalizing B cells include overexpressing ras genes and overexpressing human papillomavirus 16E6 and E7 genes (See Coursen et al., 1997). Another combination of genes that can be utilized is hTERT, sv40 large T oncoprotein and an onco-allele of H-ras.

For some applications it may be desirable to generate B cells that are capable of expressing one or more Ig receptors and are also immortal. One means of achieving this is to use embryos derived from an animal that is transgenic for one or more immortalizing genes. One such animal is an IMMORTOMOUSE® mouse, commercially available through Charles River Laboratories. Such mice have a temperature sensitive SV40 T antigen gene in most cells. Those of ordinary skill in the art will recognize that immortal B cells may also be obtained by using transgenic animals that carry additional genes known to immortalize cells as described above such as hTERT or H-ras.

In addition to comprising vectors comprising a nucleic acid encoding at least one surface expressed antibody receptor selected from the group consisting of Igα and Igβ, the B cells of the present invention can also comprise a vector comprising a nucleic acid encoding U1A, an enzyme involved in inhibiting the expression of the secretory form of immunoglobulin M (See Philips et al., "Regulation of nuclear poly (A) addition controls the expression of immunoglobulin M secretory mRNA, *EMBO* 22:6443-6452 (2001).

All of the B cells comprising vectors described herein can be fused to a myeloma cell or other immortal cell line to make a hybridoma cell. The resulting hybridoma cell can be utilized in the methods of making a monoclonal antibody of interest described herein.

Plasma Cells

There are approximately $10^8$ B cells in a typical mouse spleen. About 99% of such B cells surface present antibody. However 1%, or $10^6$ of such cells are plasma cells and typically surface present only trace amounts of antibody. Plasma cells are known to produce immunoglobin that is highly specific and of strong affinity for particular target antigens. This invention provides populations of plasma cells that surface present adequate immunoglobin to enable high throughput fluorescence activated cell sorting technology to be used to determine whether single cells produce immunoglobin that react with target antigens. Such plasma cells may be obtained from any animal such as the transgenic animals provided herein and can produce fully human immunoglobin, if isolated from a transgenic animal that expresses a nucleic acid coding for human antibodies in its B cells.

As stated above, plasma cells make very specific, high affinity antibodies to target antigens. Therefore, it is desirable to isolate plasma cells from among a larger population of B cells prior to sorting the plasma cells to identify cells that produce desired antibodies. The marker SYNDECAN-1 is expressed to a higher degree on plasma cells than on other B cells. In addition, plasma cells do not express IGD or B220, whereas other B cells do express both markers. Commercial antibodies for SYNDECAN, IGD and B220 are available and the three markers may be used by those of ordinary skill in the art to segregate plasma cells from among B cell populations by methods known in the art. Plasma cells may also be separated from other cells by density-based centrifugation where the fraction containing plasma cells is collected using an elutriator. Alternatively, a purified plasma cell population may be achieved using separation/purification columns such as those that utilizing magnetic beads.

The present invention provides a population of plasma cells wherein greater than 5% of the cells in the population express monoclonal antibody that is bound to the cell surface. Also provided by this invention is a population of plasma cells wherein greater than 10%, 15%, 20%, 25%, 30%, 35%, 40%, 45%, 50%, 55%, 60%, 65%, 70%, 75%, 80%, 85%, 90%, or 95% of the cells in the population express monoclonal antibody that is bound to the cell surface.

The present invention also provides a plasma cell, wherein greater than twenty monoclonal antibody molecules are expressed and bound to the cell surface. Also provided by the present invention is a plasma cell, wherein greater than fifty monoclonal antibody molecules are expressed and bound to the cell surface. Further provided by the present invention is a plasma cell, wherein greater than one hundred monoclonal antibody molecules are expressed and bound to the cell surface. The present invention also provides a plasma cell, wherein greater than two hundred and fifty monoclonal antibody molecules are expressed and bound to the cell surface. Also provided by the present invention is a plasma cell, wherein greater than five hundred monoclonal antibody molecules are expressed and bound to the cell surface.

Further provided by this invention is a population of plasma cells comprising a vector comprising a nucleic acid encoding Igα and/or Igβ that expresses monoclonal antibody bound to the cell surface, wherein when the monoclonal antibody is detected by fluorescence, the fluorescence intensity of the population of cells is at least two fold greater than the fluorescence intensity of a population of plasma cells that do not comprise a vector comprising a nucleic acid encoding Igα and/or Igβ.

The invention also provides a population of plasma cells comprising a vector comprising a nucleic acid encoding Igα and/or Igβ that expresses monoclonal antibody bound to the cell surface, wherein when the monoclonal antibody is detected by fluorescence, the fluorescence intensity of the population of cells is at least two fold, three fold, four fold, five fold, six fold, seven fold, eight fold, nine fold, ten fold, fifteen fold, twenty fold, thirty fold, forty fold, fifty fold, sixty fold, seventy fold, eighty fold, ninety fold, one hundred fold, two hundred and fifty fold, five hundred fold, one hundred fold, two hundred and fifty fold, five hundred fold or one thousand fold greater than the fluorescence intensity of a population of plasma cells that do not comprise a vector comprising a nucleic acid encoding Igα and/or Id. The fold increase in fluorescence intensity can also be any amount in between the fold increases listed above. The fold increase in fluorescence intensity can be measured by methods standard in the art and is described herein in the Examples.

The population of plasma cells utilized to measure fluorescence intensity can be between 25 and 500 cells. Therefore, the population can be about 25, 50, 75, 100, 125, 150, 175, 200, 225, 250, 275, 300, 325, 350, 375, 400, 425, 450, 475, 500 cells or any number of cells in between these values.

The plasma cells in the population can comprise a vector comprising a nucleic acid encoding Igα.

Further provided by the present invention is a population of plasma cells comprising a vector comprising a nucleic acid encoding Igα and/or Igβ that expresses monoclonal antibody bound to the cell surface, wherein when the monoclonal antibody is detected by fluorescence, the fluorescence intensity of at least 10% of the cells is at least two fold greater than the fluorescence intensity of a population of plasma cells that do not comprise a vector comprising a nucleic acid encoding Igα and/or Id.

The present invention also provides a population of plasma cells comprising a vector comprising a nucleic acid encoding Igα and/or Igβ that expresses monoclonal antibody bound to the cell surface, wherein when the monoclonal antibody is detected by fluorescence, the fluorescence intensity of at least 20%, 30%, 40%, 50%, 60%, 70%, 80%, 90%, 100% or any percentage in between of the cells is at least two fold greater than the fluorescence intensity of a population of plasma cells that do not comprise a vector comprising a nucleic acid encoding Igα and/or Ig13.

The present invention also provides a population of plasma cells comprising a vector comprising a nucleic acid encoding Igα and/or Igβ that expresses monoclonal antibody bound to the cell surface, wherein when the monoclonal antibody is detected by fluorescence, the fluorescence intensity of at least 10%, 20%, 30%, 40%, 50%, 60%, 70%, 80%, 90%, 100% or any percentage in between of the cells is at least two fold, three fold, five fold, six fold, seven fold, eight fold, nine fold, ten fold, twenty fold, thirty fold, forty fold, fifty fold, sixty fold, seventy fold, eight fold, ninety fold, one hundred fold, two hundred and fifty fold, five hundred fold, one thousand fold or any amount in between, greater than the fluorescence intensity of a population of plasma cells that do not comprise a vector comprising a nucleic acid encoding Igα and/or Igβ.

All of the populations of plasma cells described herein can be utilized in the methods of making antibodies provide by the present invention such that the plasma cells of the present invention can be contacted with an antigen/antigens in order to identify monoclonal antibody producing cells which can be isolated and subsequently produced.

Myeloma Cells

The present invention also provides a myeloma cell that comprises at least one nucleic acid functionally encoding at least one surface-expressed antibody receptor selected from the group consisting of Igα and Igβ, wherein the nucleic acid encoding the surface-expressed antibody receptor is functionally linked to an inducible expression sequence.

Further provided by the present invention is a myeloma cell that comprises at least one nucleic acid functionally encoding at least one mutated surface-expressed antibody receptor selected from the group consisting of Igα and Igβ, wherein the nucleic acid encoding the surface-expressed antibody receptor is functionally linked to an inducible expression sequence.

Also provided by the present invention is a myeloma cell that comprises a nucleic acid functionally encoding a mutated Igα receptor having a deletion of amino acid residues 176-220, wherein the nucleic acid encoding the surface-expressed antibody receptor is functionally linked to an inducible expression sequence.

Further provided by this invention is a myeloma cell that comprises a nucleic acid functionally encoding a mutated Igα receptor having one or more mutations selected from the group consisting of: Y176F, Y182F, Y193F, Y204F, wherein the nucleic acid encoding the surface-expressed antibody receptor is functionally linked to an inducible expression sequence.

The present invention further provides a myeloma cell that comprises a nucleic acid functionally encoding a mutated Igβ receptor having one or more mutations selected from the group consisting of: Y190F and Y206F, wherein the nucleic acid encoding the surface-expressed antibody receptor is functionally linked to an inducible expression sequence.

Any of the myeloma cells comprising vectors provided by the present invention can be fused to a B cell, including a B cell comprising a vector of the present invention, to make a hybridoma cell. The resulting hybridoma cell can then be used in the methods of making monoclonal antibodies described herein.

The present invention also provides a method of making a myeloma cell that comprises at least one nucleic acid functionally encoding at least one surface-expressed antibody receptor selected from the group consisting of Igα and Igβ, wherein the nucleic acid encoding the surface-expressed antibody receptor is functionally linked to an inducible expression sequence comprising the steps of transfecting a myeloma cell with at least one nucleic acid functionally encoding at least one surface-expressed antibody receptor selected from the group consisting of Igα and Igβ, wherein the nucleic acid encoding the surface-expressed antibody receptor is functionally linked to an inducible expression sequence.

The present invention also provides a method of making a myeloma cell that comprises at least one nucleic acid functionally encoding at least one mutated surface-expressed antibody receptor selected from the group consisting of Igα and Igβ, wherein the nucleic acid encoding the surface-expressed antibody receptor is functionally linked to an inducible expression sequence comprising transfecting a myeloma cell with at least one nucleic acid functionally encoding at least one mutated surface-expressed antibody receptor selected from the group consisting of Igα and Igβ, wherein the nucleic acid encoding the surface-expressed antibody receptor is functionally linked to an inducible expression sequence.

Also provided by the present invention is a method of making a myeloma cell that comprises a nucleic acid functionally encoding a mutated Igα receptor having one or more mutations selected from the group consisting of: Y176F, Y182F, Y193F, Y204F, wherein the nucleic acid encoding the surface-expressed antibody receptor is functionally linked to an inducible expression sequence comprising transfecting a myeloma cell with a nucleic acid functionally encoding a mutated Igα receptor having one or more mutations selected from the group consisting of: Y176F, Y182F, Y193F, Y204F, wherein the nucleic acid encoding the surface-expressed antibody receptor is functionally linked to an inducible expression sequence.

The present invention provides a method of making a myeloma cell that comprises a nucleic acid functionally encoding a mutated Igβ receptor having one or more mutations selected from the group consisting of: Y190F and Y206F, wherein the nucleic acid encoding the surface-expressed antibody receptor is functionally linked to an inducible expression sequence comprising transfecting a myeloma cell with a nucleic acid functionally encoding a mutated Igβ receptor having one or more mutations selected from the group consisting of: Y190F and Y206F, wherein the nucleic acid encoding the surface-expressed antibody receptor is functionally linked to an inducible expression sequence.

The present invention provides a method of making a myeloma cell that comprises a nucleic acid functionally encoding a mutated Igα receptor having a deletion of amino acid residues 176-220, wherein the nucleic acid encoding the surface-expressed antibody receptor is functionally linked to an inducible expression sequence comprising transfecting a myeloma cell with a nucleic acid functionally encoding a mutated Igα receptor having a deletion of amino acid residues 176-220, wherein the nucleic acid encoding the surface-expressed antibody receptor is functionally linked to an inducible expression sequence.

In addition to comprising vectors comprising a nucleic acid encoding at least one surface expressed antibody receptor selected from the group consisting of Igα and Igβ the myeloma cells of the present invention can also comprise a vector comprising a nucleic acid encoding U1A, an enzyme involved in inhibiting the expression of the secretory form of immunoglobulin M (See Philips et al., "Regulation of nuclear poly (A) addition controls the expression of immunoglobulin M secretory mRNA, *EMBO* 22:6443-6452 (2001).

The present invention also provides a method of screening myeloma cells or other other immortal cells for the presence of Igα and Igβ on their surface. If a myeloma cell or am immortal cell naturally expressing Iva and Igβ is identified, this cell can be fused to B cells to produce hybridoma cells expressing monoclonal antibodies on their cell surface. If a myeloma cell or an immortal cell naturally expressing Igα is identified, this cell can be fused to the B cells of the present invention to produce hybridoma cells expressing monoclonal antibodies on their cell surface. Alternatively, this cell can be transfected with a vector comprising a nucleic acid encoding Igβ and then fused to a B cell in order to produce hybridoma cells expressing monoclonal antibodies on their cell surface. If a myeloma cell or an immortal cell naturally expressing Igβ is identified, this cell can be fused to the B cells of the present invention to produce hybridoma cells expressing monoclonal antibodies on their cell surface. Alternatively, this cell can be transfected with a vector comprising a nucleic acid encoding Igα and then fused to a B cell in order to produce hybridoma cells expressing monoclonal antibodies on their cell surface.

Myeloma cells can also be screened to determine which of the myeloma cells is a suitable fusion partner for making hybridomas. One of skill in the art would know how to test myelomas for desirable fusion characteristics either before or after screening for the presence of Igα and/or Igβ in order to determine which ones are best suited for fusion with B cells. Alternatively, once a myeloma cell or immortalized cell is deemed to be suitable for fusion, this myeloma cell can be transfected with Igα and/or Igβ prior to fusion with a B cell. In addition, since HAT selection is not required, the investigator's choice of the cell to be used as a fusion partner for B cells in a given protocol is greatly expanded. Using DISH, myelomas or other candidate fusion partners can be identified that are more cell sparing or offer other advantages over standard myelomas in use today.

Methods of Making Monoclonal Antibodies

The present invention provides method of making a monoclonal antibody of interest comprising: a) contacting a population of hybridoma cells wherein greater than 15% of the cells in the population express monoclonal antibody that is bound to the cell surface with an antigen linked to a detectable label, wherein the antigen binds to the monoclonal antibody to yield a detectably labeled hybridoma cell; b) isolating the detectably labeled hybridoma cell, thus identifying a hybridoma cell that produces the monoclonal antibody of interest; c) making the monoclonal antibody of interest from the hybridoma cell.

Also provided is a method of making a monoclonal antibody of interest comprising: a) contacting a population of hybridoma cells wherein greater than 15% of the cells in the population express monoclonal antibody that is bound to the cell surface with an antigen, wherein the antigen binds to the monoclonal antibody; b) adding a detectable label to the antigen to yield a detectably labeled hybridoma cell; c) isolating the detectably labeled hybridoma cell, thus identifying a hybridoma cell that produces the monoclonal antibody of interest; d) making the monoclonal antibody of interest from the hybridoma cell.

In the methods of making a monoclonal antibody described herein, conditions whereby an antigen/antibody complex can form as well as assays for the detection of the formation of an antigen/antibody complex and quantitation of the detected protein are standard in the art. Such assays can include, but are not limited to, Western blotting, immunoprecipitation, immunofluorescence, immunocytochemistry, immunohistochemistry, fluorescence activated cell sorting (FACS), fluorescence in situ hybridization (FISH), immunomagnetic assays, ELISA, ELISPOT (Coligan et al., eds., Current Protocols in Immunology, Wiley, New York (1995)), agglutination assays, flocculation assays, cell panning, magnetic separation etc., as are well known to those of skill in the art.

The antigen of this invention can be bound to a substrate (e.g., beads, tubes, slides, plates, nitrocellulose sheets, etc.) or conjugated with a detectable label (moiety) or both bound and conjugated. The detectable moieties contemplated for the present invention can include, but are not limited to, an immunofluorescence moiety (e.g., fluorescein, rhodamine), a radioactive moiety (e.g., $^{32}P$, $^{125}I$, $^{35}S$), an enzyme moiety (e.g., horseradish peroxidase, alkaline phosphatase), a colloidal gold moiety, a dye and a biotin moiety. Such conjugation techniques are standard in the art (see, e.g., Harlow and Lane, "Antibodies, A Laboratory Manual" Cold Spring Harbor Publications, New York, (1988); Yang et al., *Nature* 382: 319-324 (1996)). Labels can be coupled either directly or indirectly to the antigens. One example of indirect coupling is by use of a spacer moiety. These spacer moieties, in turn, can be either insoluble or soluble (Diener et al., *Science* 231: 148 (1986)).

There are many different labels and methods of labeling known to those of ordinary skill in the art. Examples of the types of labels which can be used in the present invention include enzymes, radioisotopes, fluorescent compounds, chemiluminescent compounds, microspheres dyes and bioluminescent compounds. Furthermore, the binding of these labels to the antigens required for practice of the invention can be done using standard techniques common to those of ordinary skill in the art.

Since the populations of hybridomas described herein can produce more than one monoclonal antibody, the present invention provides for methods of making monoclonal antibodies, wherein the population of cells is contacted with more than one antigen. Once each antigen binds a monoclonal antibody of interest, each one can be detected by a separate label, thus identifying more than one monoclonal antibody of interest in a population of cells. For example, the population can be contacted with three antigens, wherein each antigen is labeled either directly or indirectly with a different fluorescent label. The monoclonal antibody producing cells can be detected and the three different monoclonal antibody producing cells can be distinguished based on the differences in fluorescence associated with the different labels. Therefore, the present invention allows the isolation and production of more than one monoclonal antibody from a population of cells. This same approach can be applied to the isolation and production of multiple monoclonal antibodies from the B cells of this invention, including the isolation and production of monoclonal antibodies from the plasma cells of this invention.

In the above methods of making a monoclonal antibody of interest, a population of hybridoma cells wherein greater than 20%, 25%, 30%, 35%, 40%, 45%, 50%, 55%, 60%, 65%, 70%, 75%, 80%, 85%, 90%, or 95% can be contacted with the antigen.

A method of making a monoclonal antibody of interest comprising: a) contacting a hybridoma cell, wherein greater than twenty monoclonal antibody molecules are expressed and bound to the cell surface with an antigen linked to a detectable label, wherein the antigen binds to the monoclonal antibody to yield a detectably labeled hybridoma cell; b) isolating the detectably labeled hybridoma cell, thus identifying a hybridoma cell that produces the monoclonal antibody of interest; c) making the monoclonal antibody of interest from the hybridoma cell.

A method of making a monoclonal antibody of interest comprising: a) contacting a hybridoma cell, wherein greater than twenty monoclonal antibody molecules are expressed and bound to the cell surface with an antigen, wherein the antigen binds to the monoclonal antibody; b) adding a detectable label to the antigen to yield a detectably labeled hybridoma cell; c) isolating the detectably labeled hybridoma cell, thus identifying a hybridoma cell that produces the monoclonal antibody of interest; d) making the monoclonal antibody of interest from the hybridoma cell.

In the above methods of making a monoclonal antibody of interest, a hybridoma cell wherein greater than fifty, one hundred, two hundred and fifty or five hundred monoclonal antibody molecules are expressed and bound to the cell surface can be contacted with the antigen.

In all of the methods of making a monoclonal antibody of interest, the hybridoma cells can comprise a vector comprising a nucleic acid encoding at least one surface-expressed antibody receptor selected from the group consisting of Igα and Igβ. The nucleic acid encoding at least one surface-expressed antibody receptor selected from the group consisting of Igα and Igβ can be a mutated Igα and/or mutated Igβ, a chimeric Igα and/or chimeric Igβ as described above.

The present invention also provides a method of making a monoclonal antibody of interest comprising: a) contacting a B cell comprising a vector, wherein the vector comprises a nucleic acid encoding at least one surface-expressed antibody receptor selected from the group consisting of Igα and Igβ with an antigen linked to a detectable label, wherein the antigen binds to the monoclonal antibody to yield a detectably labeled B cell; b) isolating the detectably labeled B cell, thus identifying a B cell that produces the monoclonal antibody of interest; and c) making the monoclonal antibody of interest.

The present invention also provides a method of making a monoclonal antibody of interest comprising: a) contacting a B cell comprising a vector, wherein the vector comprises a nucleic acid encoding at least one surface-expressed antibody receptor selected from the group consisting of Igα and Igβ with an antigen; b) add a detectable label that binds to the antigen to yield a detectably labeled B cell; c) isolating the detectably labeled B cell, thus identifying a B cell that produces the monoclonal antibody of interest; and d) making the monoclonal antibody of interest.

The invention further provides a method of making a monoclonal antibody of interest comprising: a) contacting a B cell comprising a vector, wherein the vector comprises a nucleic acid encoding at least one surface-expressed antibody receptor selected from the group consisting of Igα and Igβ with an antigen linked to a detectable label, wherein the antigen binds to the monoclonal antibody to yield a detectably labeled B cell; b) isolating the detectably labeled B cell, thus identifying a B cell that produces the monoclonal antibody of interest; c) determining the amino acid sequence of the variable region of the monoclonal antibody; and d) making the monoclonal antibody of interest. The amino acid sequence of the variable region of the monoclonal antibody can be determined by obtaining RNA from an antibody producing cell, such as a B cell, constructing a cDNA, amplifying the cDNA by utilizing primers corresponding to a DNA sequence in the variable region of the immunoglobulin chain, determining the nucleotide sequence and translating the nucleotide sequence in order to obtain an amino acid sequence for the variable region of the monoclonal antibody. For the purposes of determining the amino acid sequence of the variable region of a monoclonal antibody, please see, U.S. Pat. No. 5,627,052 which is hereby incorporated in its entirety by this reference.

The invention further provides a method of making a monoclonal antibody of interest comprising: a) contacting a B cell comprising a vector, wherein the vector comprises a nucleic acid encoding at least one surface-expressed antibody receptor selected from the group consisting of Igα and Igβ with an antigen linked to a detectable label, wherein the antigen binds to the monoclonal antibody to yield a detectably labeled B cell; b) isolating the detectably labeled B cell, thus identifying a B cell that produces the monoclonal antibody of interest; c) obtaining a nucleic acid encoding the variable region of the monoclonal antibody and d) making the monoclonal antibody of interest. A nucleic acid encoding the variable region of the monoclonal antibody can be obtained by isolating DNA from an antibody producing cell, such as a B cell. Once DNA is isolated, the DNA sequences encoding the rearranged variable regions, including the complementarity determining regions are amplified by PCR and the resulting amplification product sequenced. For the purposes of obtaining a nucleic acid encoding the variable region of a monoclonal antibody, please see U.S. Pat. No. 5,627,052 which is hereby incorporated in its entirety by this reference. In all of the methods of making a monoclonal antibody of interest from B cells, the B cells can comprise a vector comprising a nucleic acid encoding at least one surface-expressed antibody receptor selected from the group consisting of Igα and Igβ. The nucleic acid encoding at least one surface-expressed antibody receptor selected from the group consisting of Igα and Igβ can be a mutated Igα and/or mutated Igβ, a chimeric Igα and/or chimeric Id.

The present invention also provides a method of making a hybridoma cell that produces a monoclonal antibody that recognizes a selected antigen comprising: a) immunizing a mouse with the antigen; b) fusing a B cell from the immunized mouse with a myeloma cell that comprises at least one nucleic acid functionally encoding at least one surface-expressed antibody receptor selected from the group consisting of Igα and Igβ to produce a monoclonal antibody producing hybridoma cell, wherein the monoclonal antibody produced by the hybridoma cell is expressed and bound to the cell surface; c) contacting the monoclonal antibody producing hybridoma cell with the antigen, wherein the antigen binds to the monoclonal antibody on the cell surface to produce a detectable hybridoma cell, and d) isolating the detectable hybridoma cell, thus making a hybridoma cell that produces a monoclonal antibody that recognizes a specific antigen. In this method, the antigen can be directly labeled to yield a detectably labeled hybridoma cell.

As used herein, an "antigen" can be a peptide, a polypeptide, a recombinant polypeptide, a carbohydrate, a nucleic acid, a lipid, a fragment of a polypeptide, such as a C-terminal fragment or an N-terminal fragment, an organic compound, a synthetic compound, a naturally occurring compound derived from bacterial, plant, animal, protist or fungal source. The antigen can also comprise the binding site of a cell surface receptor such that monoclonal antibodies against that particular site can be made to target a cell surface receptor.

A method of making a hybridoma cell that produces a monoclonal antibody that recognizes a selected antigen comprising: a) contacting a B cell comprising a vector, wherein the vector comprises a nucleic acid encoding at least one surface-expressed antibody receptor selected from the group consisting of Igα and Igβ with an antigen wherein the antigen binds to the monoclonal antibody to yield a detectable B cell; b) isolating the detectable B cell, thus identifying a B cell that produces the monoclonal antibody of interest and; c) fusing the B cell that produces the monoclonal antibody of interest to a myeloma cell to produce a hybridoma cell that produces a monoclonal antibody that recognizes a selected antigen. In this method, the antigen can be directly labeled to yield a detectably labeled B cell.

Also provided by this invention is a transgenic animal comprising B cells comprising a vector, wherein the vector comprises a nucleic acid encoding at least one surface-expressed antibody receptor selected from the group consisting of Igα and Igβ functionally linked to expression sequences, including but not limited to a promoter, intronic sequences and poly-adenylation signal sequences. The B cells comprising a vector can comprise at least one mutated surface-expressed antibody receptor selected from the group consisting of Igα and Igβ. The B cells comprising a vector can comprise at least one chimeric surface-expressed antibody receptor selected from the group consisting of Igα and Igβ. The B cells comprising a vector can comprise a mutated Igα receptor comprising one or more mutations selected from the group consisting of: Y176F, Y182F, Y193F, Y204F. The B cells comprising a vector can comprise a mutated Igβ receptor comprising one or more mutations selected from the group consisting of: Y190F and Y206F.

The "transgenic non-human animals" of the invention are produced by introducing transgenes into the germline of the non-human animal. The transgenic animals of this invention can be made by methods known in the art. For the purposes of generating a transgenic animal, screening the transgenic animal for the presence of a transgene and other methodology regarding transgenic animals, please see U.S. Pat. No. 6,111,166 which is incorporated by this reference in its entirety. For example, the transgenic animals of this invention can be made by a) injecting a transgene comprising a nucleic acid encoding Igα. functionally linked to an expression sequence and/or a transgene comprising a nucleic acid encoding Igβ. functionally linked to an expression sequence into an embryo, wherein the transgene is incorporated into the genome of the embryo and b) allowing the embryo to develop into an animal. This can further comprise crossing the animal with a second animal to produce a third animal. B cells comprising a transgene, wherein the transgene comprises a nucleic acid encoding at least one surface-expressed antibody receptor selected from the group consisting of Igα and Igβ can be isolated from the transgenic animal of this invention. The transgenic animals of the present invention include, but are not limited to, mouse, rat, rabbit, guinea pig.

In the transgenic animals of the present invention, the transgene can be expressed in immature B cells, mature naive B cells, mature activated B cells, memory B cells, B lineage lymphocytes and/or plasma cells. Therefore, the expression sequences can be selected such that expression of the transgene is directed to B cells, but not exclusively to B cells. The expression sequence can direct expression to one, more than one or all of the following types of B cells: immature B cells, mature naive B cells, mature activated B cells, memory B cells, B lineage lymphocytes and plasma cells.

In the transgenic animals of the present invention, expression of the transgene can be controlled by an inducible promoter. The transgenic animal of this invention can utilize an inducible expression system such as the cre-lox, metallothionene, or tetracycline-regulated transactivator system. Using the example of the cre-lox system, the genes of interest (Igα and Igβ) are inserted onto a plasmid or suitable viral vector containing a stop codon flanked by locus of crossing over (loxP) sites which comprise two 13 base pair inverted repeats separated by an 8 base pair spacer region. This cassette is under control of a specific promoter such as the immunoglobulin kappa, immunoglobulin lambda, CD19, CD45R/B220, CD81 (TAPA-1), or CD138 (syndecan-1) promoter. The genes of interest are inserted in the plasmid on the opposite side of the loxP-stop-loxP region from the cell specific promoter. In another plasmid, cre-recombinase is inserted next to a promoter whose expression may be controlled (proI). Each plasmid is micro-injected into the pronuclei of separate embryos and the embryos implanted into a pseudopregnant female. Additionally, the plasmids may be used to transform embryonic stem cells from a suitable animal. The latter will thereafter be combined with blastocysts from the same or similar non-human animal and re-implanted into pseudopregnant foster mothers to generate chimeric animals comprising the plasmid comprising the transgene. Further methods of generating transgenic animals well known in the art, such as lipofectin or viral transfection of embryonic stem cells or pre-implantation embryos, may also be used. Alternatively, mice bearing a proI-cre transgene may include already established mice such as the interferon inducible 'Mx-Cre' mouse by Kuhn et al. (see below).

Transgenic animals are mated and the resulting F1 animals are screened for the gene via PCR and/or Southern blot analysis. After homozygocity for the transgene is established, animals possessing the proI-cre sequence are then mated with animals with an intact pro-loxP-stop-loxP-Igα-Igβ. The resulting F1 animals are then screened for individuals possessing both transgenes by PCR and/or Southern blot analysis. In the case of the 'Mx-Cre' cre recombinase transgene, expression of the pro-loxP-stop-loxP-Igα-Igβ transgene is achieved by initiating expression of the cre recombinase such as through the injection of type-1 interferon (IFN) as is the case with the 'Mx-Cre' cre recombinase transgene. The cre-recombinase will then initiate a recombination event targeted at the loxP sites by binding at the inverted repeats of one loxP site and forming a synapse with the second site. Cre-recombinase will then cleave the DNA in the spacer region and initiate strand exchange between the synapted loxP sites. This will result in the deletion of the stop codon and transcription from the promoter through the Igα and Igβ genes. A similar method is detailed by M. Lasko et al., in "Targeted oncogene activation by site-specific recombination in transgenic mice," PNAS, 89, 6232-6236, July 1992, and is included herein in its entirety. Though this is only one method of using the cre/lox system similar results may be achieved by inserting the Igα and Igβ genes onto a plasmid or viral vector in reverse orientation to the promoter and between loxP sites in opposite orientation (pro-loxP-Ig3-Igα-loxP). In this scenario, once a recombination event is initiated the genes may reverse orientation (pro-Igα-Igβ allowing transcription. An example of this is documented in M. Mitsou et al., "Memory B-cell persistence is independent of persisting immunizing antigen," Nature 407, 636-642, Oct. 5, 2000 and included herein in its entirety. The use of Mx-Cre transgenic mouse and type-1 IFN as an inducer was published by R. Kuhn et al., "Inducible gene targeting in mice," Science, 269(5229): 1427-1429, Sep. 8, 1995, and is included herein by reference in its entirety.

In another approach, B cells from animals with an intact pro-loxP-stop-ioxP-Igα-Igβ will be treated in vitro with a cell permeable Cre recombinase protein such as that described by Jo et al., "Epigenetic regulation of gene structure and function with a cell-permeable Cre recombinase," Nature Biotechnology, 19: 929-933, 2001, and is included herein by reference in its entirety.

The transgenic animals of the present invention can also utilize a tetracycline system where the genes of interest (Igα and/or Igβ) are inserted into a plasmid or viral vector adjacent to a tetracycline-responsive promoter (TRE). In another plasmid, tetracycline-controlled transactivator (rtTA) is inserted next to a promoter that can direct expression to B cells or a constitutive promoter. As with the cre-lox system transgenic animals may be made by micro-injection of pronuclei or stem cell transformation. The resulting F1 animals are screened for the gene. Animals possessing the pro-rtTA sequence are bred to homozygocity and then mated with animals with an intact TRE-Igα-Igβ. The resulting F1 animals are then screened for individuals possessing both transgenes. Expression of the transgene is achieved by injecting tetracycline or a suitable derivative such as doxycyline. The dox will bind to the rtTA allowing binding to the TRE and promoting transcription of the Igα and/or Igβ genes. Use of the tetracycline inducible system is exemplified in D. Y. Ho et al., "Inducible gene expression from defective herpes simplex virus vectors using the tetracycline-responsive promoter system," Brain Res. Mol. Brain. Res. 41(1-2): 200-209, Sep. 5, 1996; Y. Yoshida et al., "VSV-G-pseudotyped retroviral packaging through adenovirus-mediated inducible gene expression," Biochem. Biophys. Res. Commun. 232(2): 379-382, Mar. 17, 1997; A. Hoffman et al., "Rapid retroviral delivery of tetracycline-inducible genes in a single autoregulatory cassette," PNAS, 93(11): 5185-5190, May, 28, 1996; and B. Massie et al., "Inducible overexpression of a toxic protein by an adenovirus vector with a tetracycline-regulatable expression cassette," J. Virol. 72(3): 2289-2296, March 1998, all of which are incorporated herein in their entireties by this reference.

Also provided by the present invention is a method of identifying a cell that produces a monoclonal antibody that recognizes a specific antigen comprising: a) immunizing a transgenic animal comprising B cells comprising a vector, wherein the vector comprises a nucleic acid encoding at least one surface-expressed antibody receptor selected from the group consisting of Igα and Igβ; b) isolating the B cells from the animal of step a); c) contacting the cells of step b) with the antigen, wherein the antigen binds to the monoclonal antibody to yield a detectable labeled cell; and d) isolating the detectably labeled cell, thus identifying a cell that produces a monoclonal antibody that recognizes a specific antigen.

The present invention also provides a hematopoietic stem cell comprising a vector, wherein the vector comprises a nucleic acid encoding at least one surface-expressed antibody receptor selected from the group consisting of Igα and Igβ.

The present invention is more particularly described in the following examples which are intended as illustrative only since numerous modifications and variations therein will be apparent to those skilled in the art.

EXAMPLES

This invention shows that the lack of antibody receptors Igα and/or Igβ, is the major limitation to surface presentation of antibody in hybridomas. The membrane form of antibody binds these two receptors through the membrane spanning domain that is on the C-terminus of the full-length heavy chain (mHC) as shown in FIG. 1. Most myelomas have lost the ability to produce Igα and/or Igβ, and the resulting hybridoma fusions no longer present surface mAb because they lack the Igαreceptor or the Igα and Igβ receptors (Kanavaros et al., 1995). Myelomas impart this lack of surface presentation of antibody to most hybridoma cell lines, even though many hybridomas are derived from early or mid-stage B-cells, which themselves present surface mAbs (Milcarek et al., 1996).

Figure 2B:
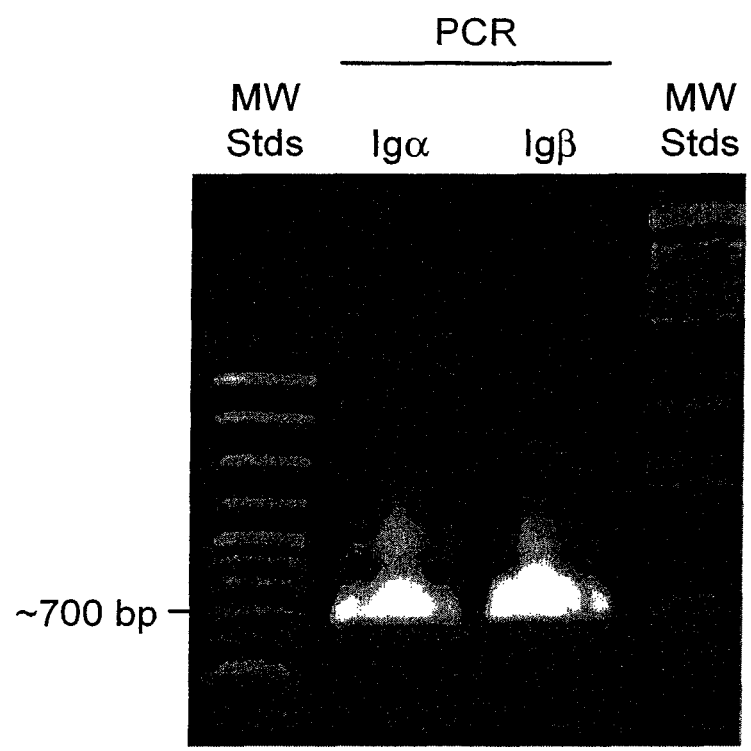
FIG. 2 shows the Primer oligonucleotides and PCR amplification of Igα and cDNAs. (A) The sequences of the sense (S) and antisense (A) primers used to amplify cDNAs encoding Igα and Igβ. These oligos add important restriction endonuclease cloning sites and 5 translation signals (GC-CACC) to the receptor sequences. (B) PCR amplification products of the expected sizes in base pairs (bp). Molecular weight standards flank the PCR products.

Engineering the constitutive expression of Igα and/or Igβ: The cDNAs encoding the two receptor sequences Igα and Igβ were PCR amplified from a mouse spleen cDNA library (Clontech). Restriction endonuclease cloning sites were added as part of the oligonucleotide primers used in the PCR amplification as shown in FIG. 2A and the appropriate-sized PCR products were obtained (FIG. 2B). The confirmed sequences of the PCR-amplified receptor for Igα and Igβ are shown in FIGS. 3 and 4, respectively. The PCR product containing Igα was digested with HindIII and EcoRI and cloned into the corresponding replacement region of the eukaryotic expression vector pcDNA3.1 (Neo) (Invitrogen, Inc.). The PCR product containing the Igβ sequence was digested with HindIII and XhoI and cloned into the corresponding replacement regions of the eukaryotic expression vector pcDNA3.1/Zeo (Invitrogen, Inc.). The structure of these two related pcDNA3.1 expression vectors are shown in FIGS. 5 and 6, respectively. The two vectors differ only in carrying resistance markers for Neomycin G418 and Zeocin, respectively. The resulting plasmids are termed p3.1NeoIgα and p3.1ZeoIgβ, respectively. Both pcDNA3.1 vectors express cloned sequences under the control of the strong constitutive CMV promoter and BGH terminator. Recombinant plasmid DNA was purified over an endotoxin free purification kit (Qiagen, Inc.) in preparation for transfection.

A well-characterized hybridoma cell line, HGS1 (fusion of Sp2/0 and a mouse B cell) was utilized (cloned line-12G7). This line makes monoclonal antibodies to E. coli glutathione synthetase (GS) as described previously. The antibody reacts well with both a synthetic peptide designed from the GS sequence or the full-length GS protein.

The myeloma cell line Sp2/0 fouls the standard fusion partner used for over a decade at University of Georgia's monoclonal facility in producing hybridomas. Sp2/0 and derived hybridomas are grown on RPMI medium (RPMI-1640, Sigma, Inc.) supplemented with 20% fetal Bovine serum (Atlanta Biologicals, Inc.) and grown at 37° C. with 5% $CO_2$.

Optimizing transfection and selection: A constitutive β-galactosidase (β-gal) reporter plasmid (pcDNA3.1/lacZ, Invitrogen) was utilized to optimize and quantify lipofection techniques on HGS 1 hybridoma and Sp2/0 myeloma cell lines. Transfection was performed by mixing 6-8 μl of LipofectAMINE reagent (Gibco BRL) with 1-2 μg of plasmid DNA for 5 hr at 37° C. in 1.0 ml of Opti-MEM I (GibcoBRL) reduced serum medium. Lipofection frequencies that occurred were relatively low, averaging approximately 30 transfectants per 500,000 cells, but were higher than previously reported for myeloma cells (Oi et al., 1983; Sun et al., 1991). The frequency of co-transfection of two DNAs was determined to average about 6-10 cells per 500,000. There was little difference between the frequency of transfecting or expressing linear or supercoiled plasmid DNA in several transfections, therefore, supercoiled DNA was used for subsequent experiments. Neomycin (Neo) (G418, Gibco BRL) and Zeocin (Invitrogen) kill curves were established on the same cells with 100% killing of control cells occurring over 7 days on 750 μg/ml G418 and 750 mg/ml Zeocin. After this initial period of selection the G418 concentration remains the same, but the Zeocin concentration is reduced to 450 μg/ml. Cells are grown under continuous selection.

Figure 7A:
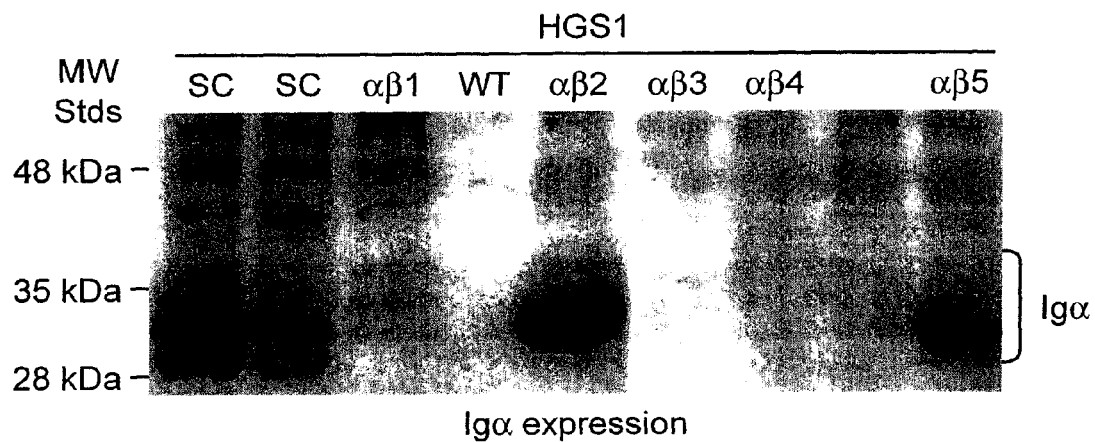
FIG. 7 shows the screening of transfected HGS cell lines for Igα and Igβ protein levels on western blots. Protein samples (25 μg of total cell protein in SDS sample buffer) were resolved on a 12% acrylamide gel, transferred to an Immobilon membrane (Millipore), reacted with rabbit polyclonal anti mouse Igα antibody (A) or Igβ antibody (B), then with donkey anti-rabbit horse antibody radish peroxdase conjugate, and developed following published protocols (Kandasamy et al., 1999). Positions of molecular weight standards (MW Stds) are shown on the left. The range of MWs of the various modified forms of Igα, are shown with a bracket. Other higher bands and bands in control WT lanes appear to be background. Extracts from cell lines are named as follows: SC, spleen cell extract; HGS1, parental hybridoma cell line producing antibodies to GS; and HGS1αβ1-5 and ECS1 αβ1-3 are the receptor gene transfected cell lines. References of these simplified designations to strain names in laboratory notebooks in the Meagher laboratory at UGA are as follows: HGS1αβ1, GS-TSC; HGS1αβ2, GS-TSC-1C; HGS1αβ3, GS-TE4; HGS1αβ4, GS-T5D-L; and HGS1αβ5, GS-TSC-3D. The Igα and Igβ specific rabbit polyclonal antibodies, anti-MB-1 and SF2B, respectively, were obtained from Dr. Linda Matsuuchi (University of British Columbia, Vancouver, Canada)(Condon et al., 2000). Antibodies were prepared against synthetic peptides to the cytoplasmic tail of Igα and the ecto-domain of Igβ.
Figure 7B:
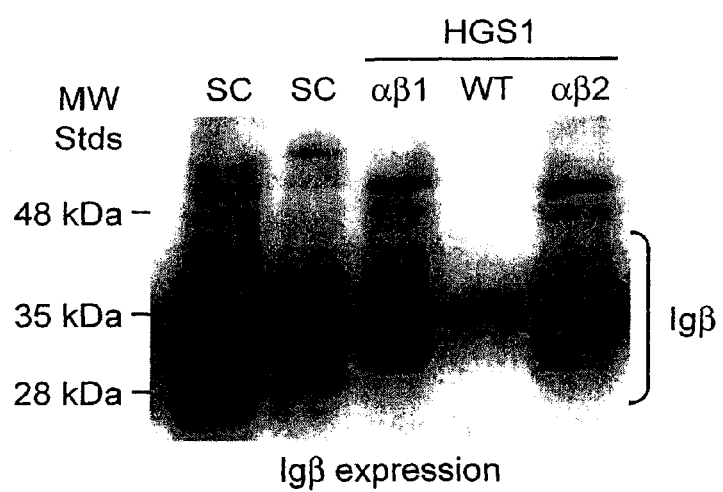

Transfection and expression of Ig receptor genes: Receptor protein levels were assayed on Western blots of crude extracts resolved by SDS-PAGE. Rabbit polyclonal antibodies to the two receptors were provided by Dr. Linda Matsuuchi (Univ. Vancouver). Strong receptor expression is seen in the 30-40 kDa range for the spleen cell control (SC) as shown in FIG. 7, while the higher molecular weight bands appear to be background. Using a double-drug selection for Neomycin and Zeocin isolated several independent and stably co-transfected cell lines (HGS1αβ1-HGS1αβ1) containing the two constructs p3.1NeoIgα and p3.1ZeoIgβ were isolated. Several of these cell lines were examined for Igα and Igβ expression on western blots. Two of five lines examined in one experiment, HGS1-Igαβ2 and HGS1-Igαβ5 (FIG. 7) produced measurable levels of Igα protein. This experiment also revealed that all cell lines examined produced significant amounts of Igβ with or without transfection with the pNeo3.1Igα and p3.1ZeoIgβ constructs. This background expression of Igβ was observed in myeloma line Sp2/0, the hybridoma line HGS 1 (derived from a fusion between Sp2/0 and a mouse B-cell), all lines derived from HGS1, and other hybridoma lines derived from Sp2/0.

Figure 8A:
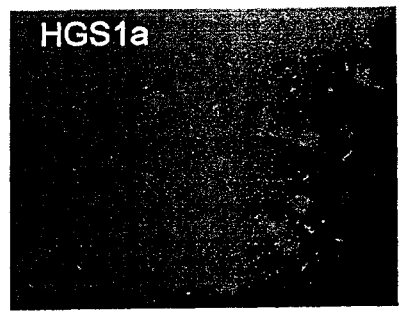
FIG. 8 shows microscopic examination of increased surface presentation of antibody on hybridoma cells expressing transgenic Ig receptors. All cells shown were treated with FITC labeled goat anti mouse antiserum. All plates were photographed using a 40× Zeiss lens and Hamamatsu digital camera (model C-4742-95) under the same illumination and exposure conditions. Cells treated with an unlabeled antibody have insignificant levels of auto-fluorescence. Cell lines shown are indicated with reference to names in lab notebooks. A & B. Non-transfected HGS1 control cells; D-H. pcDNA3.1-Igα and -Igβ transfected cells. C HGS1αβ6, SC-1C#2; D HGS1αβ7, SC-1CF 2; E. HGS1αβ8, SC-1C#3; F. HGS1 αβ9, SC-3DF3; G. HGS1αβ10, SC-3DF4: H. HGS1αβ11, SC—F1. (I) brightest cell enlarged from field of cells in FIG. 8A (HGS1a control hybridoma cells) and indicated by an arrow. (J) Brightest cell enlarged from field of cells in FIG. 8C(HGSαβ6 receptor transfected hybridoma cells) and indicated by an arrow.
Figure 8B:
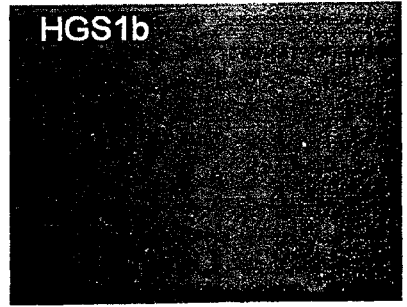
Figure 8C:
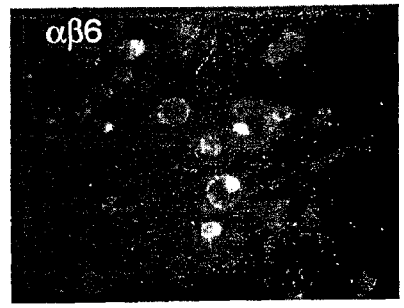
Figure 8D:
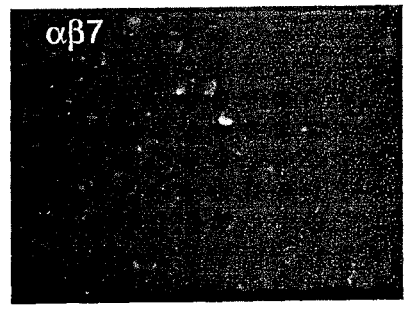
Figure 8E:
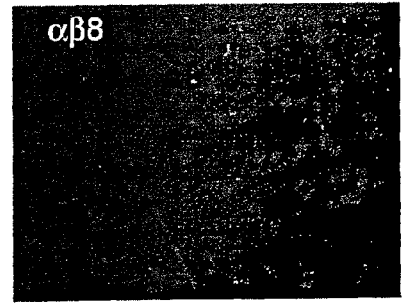
Figure 8F:
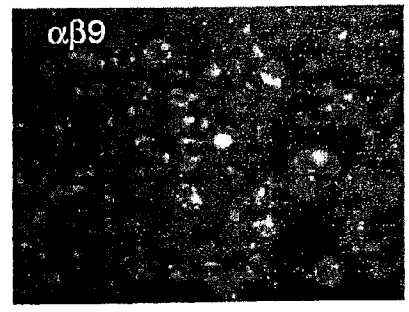
Figure 8G:
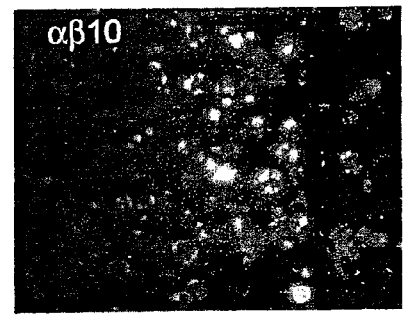
Figure 8H:
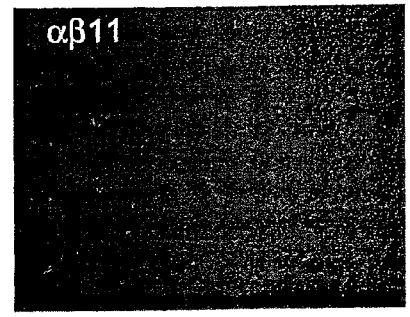
Figure 8I:
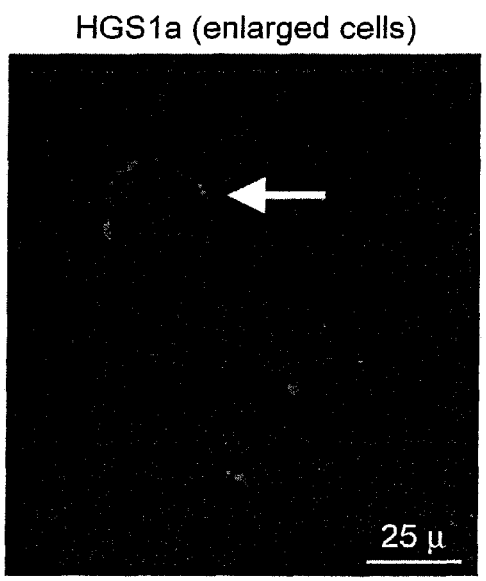
Figure 8J:
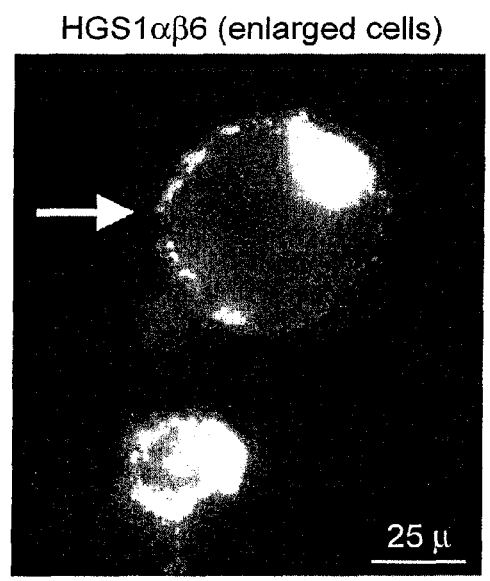

Increased surface presentation of antibody in transfected hybridoma lines: The lines expressing high levels of Igα from p3.1Neolga were examined for surface presentation of antibody in FIG. 8. FITC-labeled sheep polyclonal anti-mouse antibody (Sigma) was used to measure the base level of mouse antibody on the surface of control cells, HGS1α. A low frequency of control cells present antibody with the typical result from several experiments being shown in FIG. 8A-B. Remarkably, four of the six HGS1αβ cell lines transfected with both receptor plasmids (αβ6, αβ7, αβ9, αβ10) present large amounts of antibody on the surface of 100% of their cells as shown in FIGS. 8C, D, F, and G, respectively. A few cells in each field are out of focus, but a through focus examination of the field of cells reveals that 99% of the cells in each of the four populations present detectable levels of surface antibody. Clearly, examination of these cell populations reveals a significant increase in both the frequency of the cells that present antibody relative to the control cells and increases in the level of expression. Two of the G418 and Zeocin resistant transfected cell lines (αβ8, αβ11) showed no significant surface presentation of antibody (FIGS. 8E and 8H). Surprisingly, they presented less surface antibody, even than control HGS1 cells, with none of the 100-plus cells examined showing detectable surface expression.

Figure 9A:
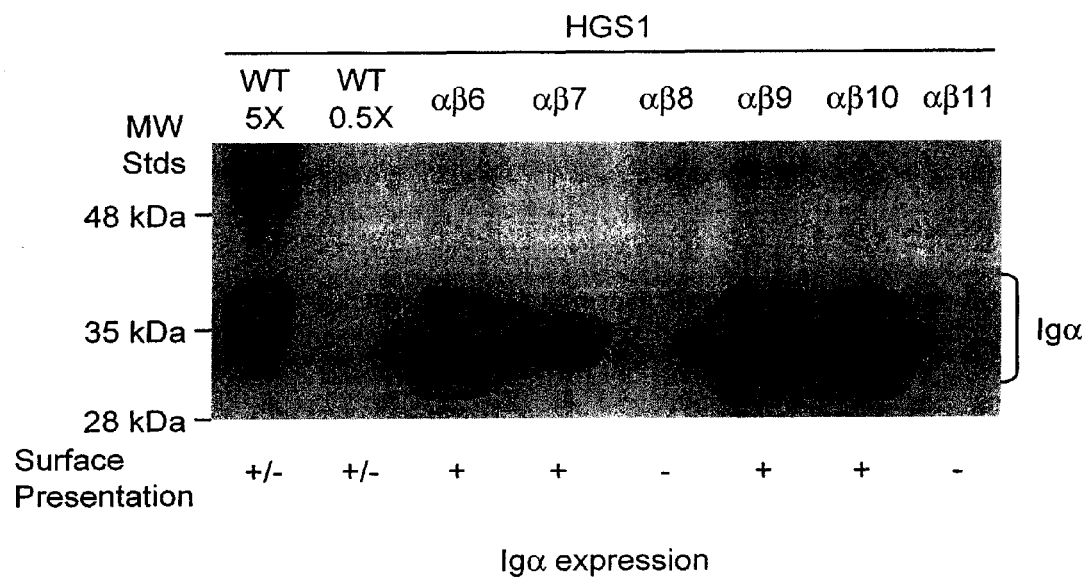
FIG. 9 shows Igα protein levels in aliquots of HGS 1 WT and HGS1αβ cells shown surface presenting antibody in FIG. 8. Protein samples were resolved by PAGE and Igα protein levels measured on Westerns using rabbit antibody to mouse Igα as in FIG. 7A. (A) Igα western (B) Coomassie stained gel of duplicate samples showing relative level of protein loading. Stained molecular weight standards (MW Stds) are shown on the left in kilo-Daltons (kDa). The range of MWs of the various modified forms of Igα are shown with a bracket. Extracts from cell lines discussed in Meagher laboratory notebooks are named as follows: WT, HGS 1 non transfected control; HGS1αβ6, SC-1C#2; HGS147, SC-1CF₂; HGS1 αβ9, SC-1C#3; HGS1αβ9, SC-3DF3; HGS1α310, SC-3DF4; and HGS1αβ11, SC—F1. Cell lines showing 100% surface presentation of antibody in FIG. 8 are designated plus +, those not presenting as minus, and HGS1 hybridoma WT controls with 1-5% presentation as +/−. Mobility range of Igα isofoinis are shown with a bracket.
Figure 9B:
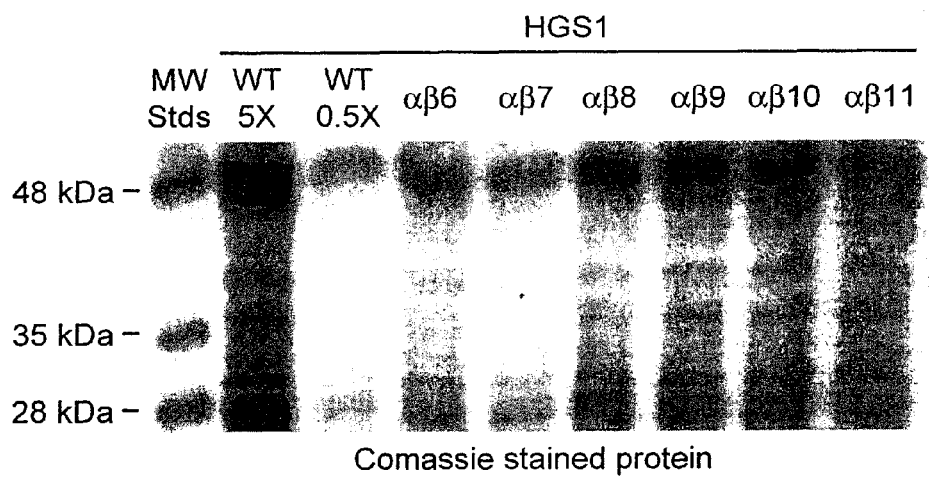
Figure 10:
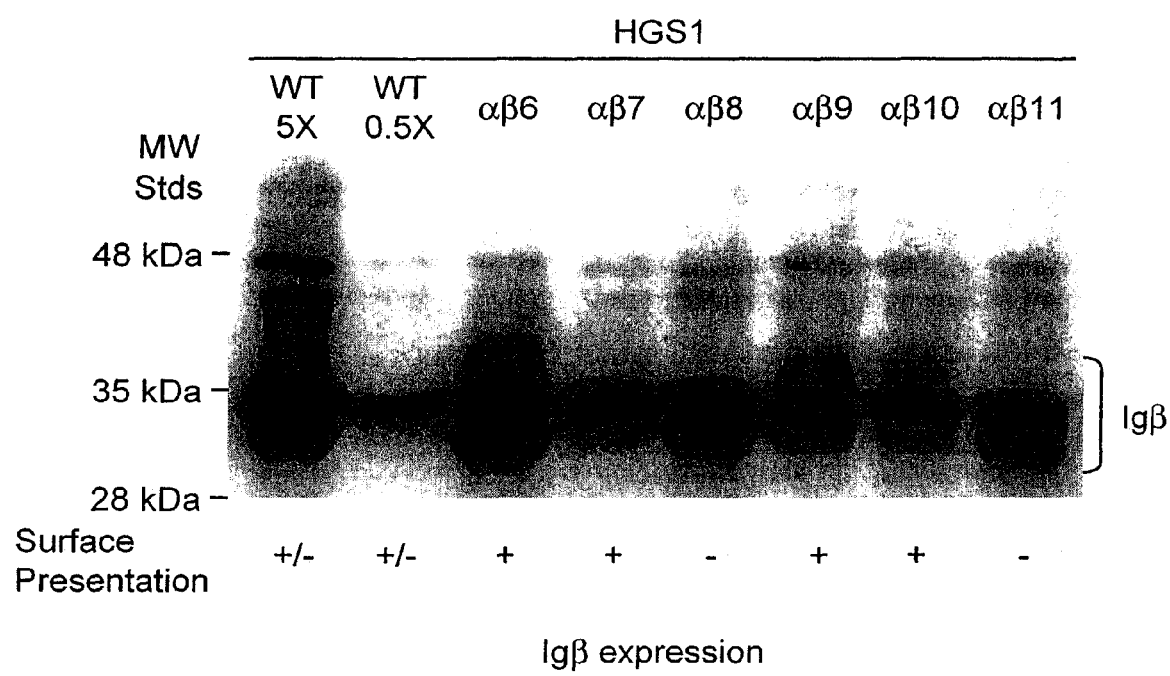
FIG. 10 shows a western blot examining, Igβ expression in aliquots of HGS1 and HGS1αβ cells shown in FIG. 8. Protein samples were resolved by PAGE and Igβ protein levels measured on Westerns using antibody to Igβ as in FIG. 7B. Protein samples are identical aliquots to those shown in FIGS. 10A and 10B. Mobility range of Igβ isoforms are shown with a bracket.

Examining Ig receptor expression in hybridoma cells presenting surface antibody: The same cell samples examined in FIG. 8 were aliquoted and frozen for subsequent examination of receptor protein levels. Initial results comparing Igα and Igβ receptor protein expression among the control HGS 1 and transfected HGS1αβ cell lines are shown in FIGS. 9 and 10, respectively. Four of the Ig receptor plasmid transfected HGS1αβ cell lines express much more Igα receptor compared to undetectable levels in control HGS1 cells. These cell lines expressing Igα are the same lines showing 100% surface presentation of antibody in FIG. 8 (C αβ36, D αβ7, F αβ9, G αβ10). The αβ7 line showed significantly less Igα protein expression than the three other lines showing strong surface expression. The αβ7 line showed surface expression of antibody in essentially all cells examined (FIG. 8D, αβ7), but at lower intensity than the other three surface expressing lines, showing a direct quantitative relationship between Igαlevels and surface presentation. Two HGS1αβ cell lines showed no Igα protein expression on the Western (48 and αβ11), and these two showed even less surface presentation than the controls. It seems possible that some form of co-suppression of Igα activity has occurred in these two negative lines. High levels of Igβ protein were detected all HGS1 derived cell lines examined and these levels did not correlate with surface presentation of antibody (FIG. 10). Thus, increased surface antibody presentation on the HGS1 lines correlates directly and even semi-quantitatively with Igα receptor protein expression.

Figure 11A:
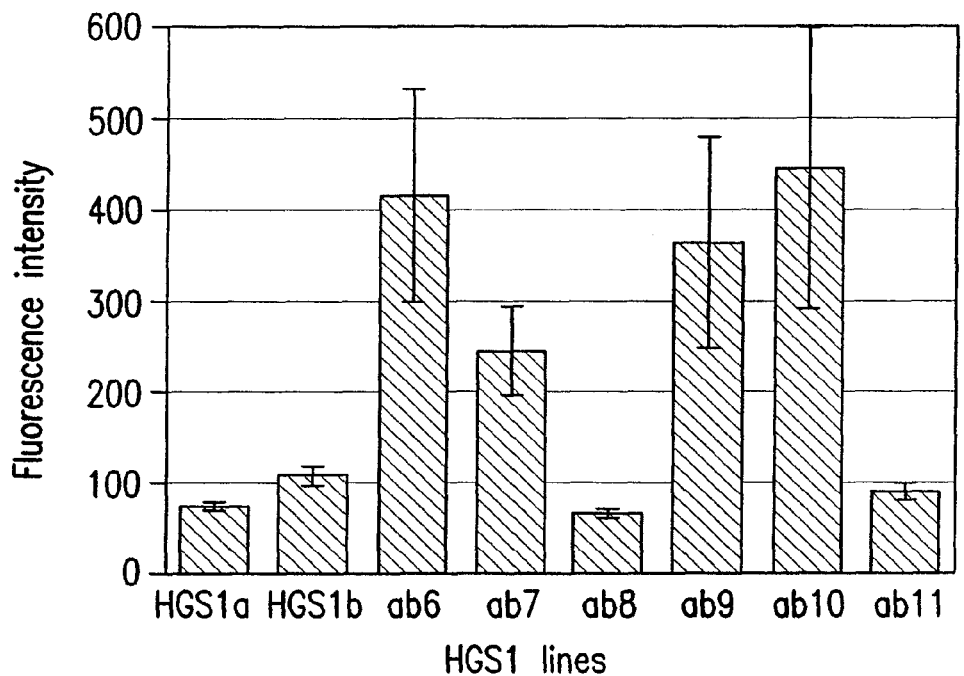
FIG. 11 shows quantification of surface presentation of antibody in Igαexpressing hybridomas. (A) The fluorescence intensity was compared among HGS 1 cells and transgenic cells expressing or not expressing detectable levels of Igα receptor. Mean fluorescence intensity (MFI) was measured for individual cells in a microscopic field from images like those taken in FIG. 8, using OpenLab software (Improvision, Inc., Boston, Mass.). Standard errors in MFI among individual cells in each population are indicated. MFI underestimates the actual intensity differences between control and transgenic cells, because 10% of the brightest cells exceed the dynamic range of the electronic camera and some cells are out of the focal plane, where MFI cannot be accurately measured n=50 cells for each of the eight cell populations examined. (B) The frequency of individual cells in each population with 3 times greater intensity than the mean for control HGS1 cells (89 MFI).
Figure 11B:
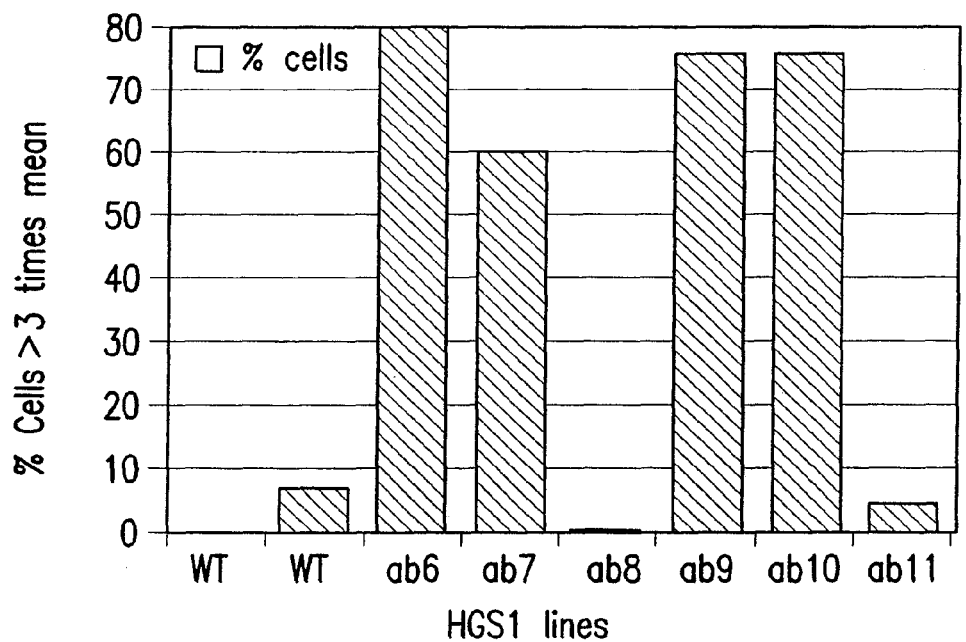

Quantification of the mean fluorescence intensity of 50 cells in each population reveals that the transgenic Igα expressing cells (αβ6, αβ7, αβ9 and αβ10) present about 5-times more antibody than control cells as shown in FIG. 11A. A high percentage (60 to 80%) of strong Igα expressing cells show a mean fluorescence intensity 3-times greater than the mean for non-Igα expressing cells (FIG. 11B). Only 0-6% of the control cells reach this level of intensity. The quantification of these data probably underestimated the actual increase in fluorescence of Igα expressing cells. These assays are limited by the dynamic range of our instrumentation for measuring the most fluorescent transgenic cells (i.e., many Igα cells are so bright they exceed the capacity of our instrumentation) and inability to assay all cells in a single focal plane. In addition, we see a low level of autofluorescence in labeled cells and weak background fluorescence in cells treated with an FITC labeled control antibody. This background may account for some of the fluorescence seen control cells (FIGS. 8A & B).

Additional experiments showed that Ig receptor overexpression and increased surface presentation of antibody did not prevent normal antibody secretion from hybridoma cells. Initial assays on cell supernatants from the eight lines examined in FIGS. 8-11 showed that each cell line still secreted significant level of mAbGS1 monoclonal antibody.

Figure 12A:
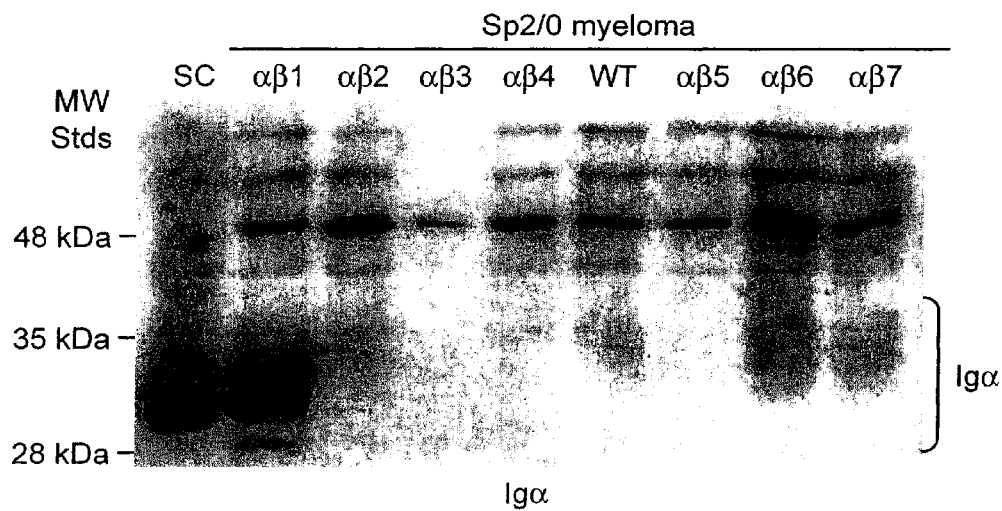
FIG. 12 shows western blot examining Igα and Igβ protein levels in transfected myeloma cell lines. Immunodetection of (A) Igα and (B) Igβ performed as described in FIG. 7. Cell lines examined are as follows: SC, spleen cells; Sp2/0 myeloma wild-type (WT) or Sp2/0 derived lines transfected with genes encoding Igα and Igβ (αβ1, M-T4; αβ2, M-T4D; αβ3, M-T6; αβ4, M-T4-3A; αβ5, M-T3SC; αβ6, M-T1 SC; and αβ7, M-T4D-6). Moblility ranges of Igα, and Igβ are shown with brackets. Higher molecular weight bands are due to background activity in antibody.
Figure 12B:
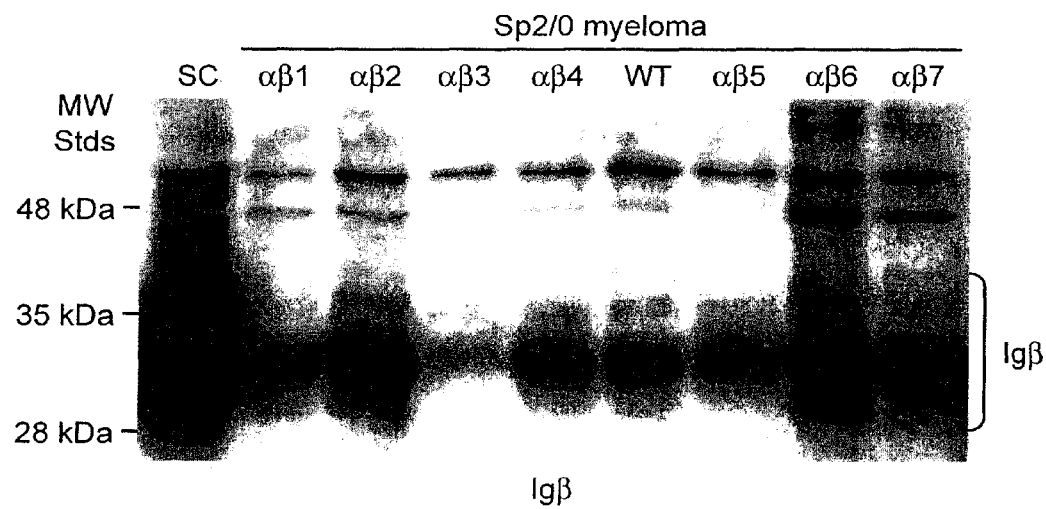

Myelomas The same genetic alteration utilized above on hybridoma cells is performed on a standard myeloma fusion partner Sp2/0. Sp2/0 is a myeloma cell line obtained from mice, *Mus musculus* (BALB/c). Sp2/0 is one of the founding myeloma cell lines used to make hybridoma fusions (Fraser and Venter, 1980; Greene et al., 1980; Hurwitz et al., 1980). First, Sp2/0 cells were co-transfected with the p3.1NeoIgα and p3.1ZeoIgβ constructs and selected for G418 and Zeocin resistance, to produce new cell lines Sp2αβ1, Sp2αβ2, etc. These Sp2αβ lines were characterized for Igα and Igβ receptor expression on western blots as shown in FIG. 12. Lines Sp2αβ1 and Sp2αβ2, show strong Igα expression, and demonstrate that there is no post-transcriptional barrier to increasing receptor expression in myeloma cells. It appears that Igβ is already expressed at measurable levels in the control Sp2/0 control cells. These myeloma cell lines are ready to be fused with B cells in order to make hybridomas. Myeloma cells can be fused to a B cell or other antibody producing cell by methods standard in the art.

Figure 13A:
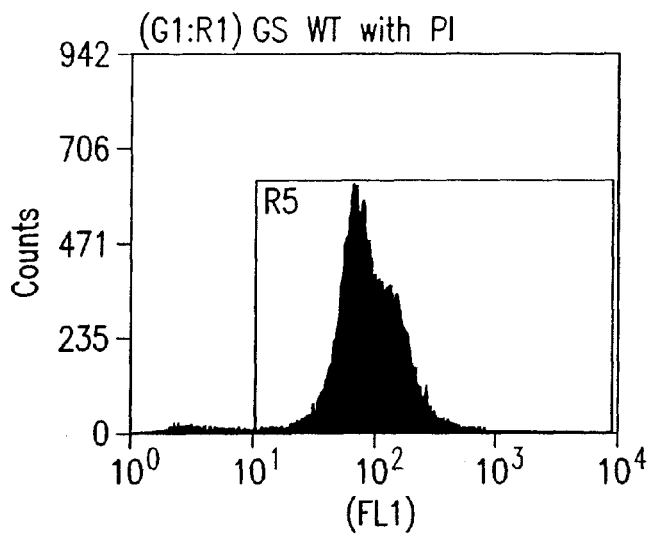
FIG. 13 shows fluorescent activated cell sorting (FACS) demonstrating that Igα expression increases antibody surface presentation eight fold. HGS 1 and HGS1αβ10 cells were prepared as shown in FIG. 8 and labeled with FITC labeled goat anti-mouse antibody. 200 μl samples of the following cells were counted (Counts) by FACS using $A_{520}$ emission (FL1). The full scale on the bottom axis represents 4-logs of fluorescence intensity. A. HGS1 WT control cells. B. HGS1αβ10 cells. C. Mixture of HGS1 and HGS1αβ10 cells.
Figure 13B:
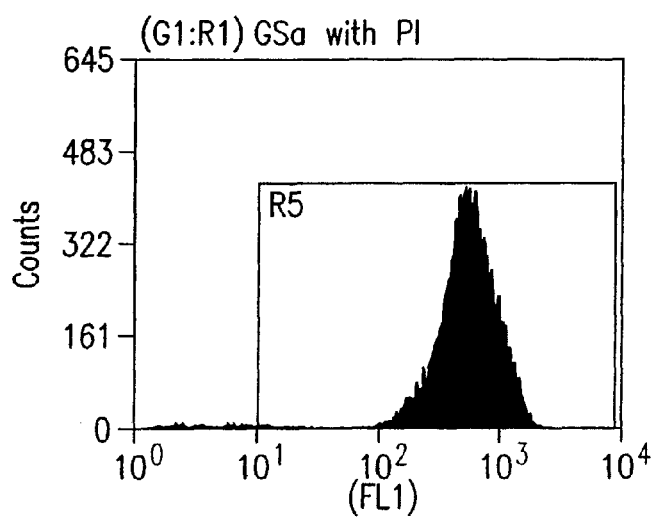
Figure 13C:
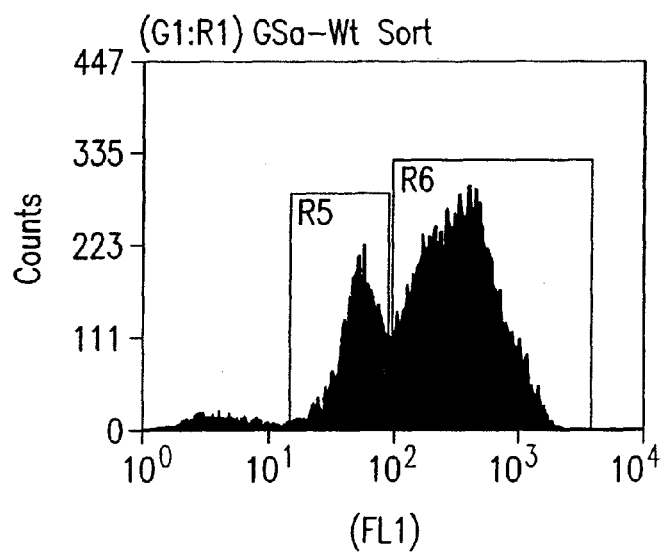

Fluorescent activated cell sorting further quantifies the increase in surface antibody presentation is linked to Igα expression: Total antibody on the surface of HGS1 cells and HGS1αβ10 cells was FITC labeled and the cells were sorted based on FITC fluorescence as shown in FIG. 13. Comparison of panels A and B reveals that the mean fluorescence of the HGSIIgαβ10 cells is about 10-times greater than the fluorescence of HGS1 control cells (i.e., FL1 level of HGS1αβ cells in B is shifted about one log to the right of control HGS1 cells in A). Panel C examines the sorting of a mixture of these cells and shows a similar result. This difference in the mean level of fluorescence serves as an independent quantification of the effect of Igα expression to FIG. 11. Increasing Igα expression results in an increase in surface presentation of mouse antibody in hybridoma cells. In sorting of normal hybridoma cell populations prepared freshly from splenic B-cells there would be none of the background fluorescence due to GS antibody presentation (right hand shoulder on the peak in A), because most cells would be making antibodies to antigens other than GS. In conclusion, this clear increase in fluorescence due to Igα expression demonstrates that DISH can be used in the direct selection of hybridomas.

Throughout this application, various publications are referenced. The disclosures of these publications in their entireties are hereby incorporated by reference into this application in order to more fully describe the state of the art to which this invention pertains.

REFERENCES

Antczak, D. F. (1982). Monoclonal antibodies: technology and potential use. J. Am Vet Med Assoc 181, 1005-10.

Blattner, F. R., Plunkett, G., 3rd, Bloch, C. A., Perna, N. T., Burland, V., Riley, M., Collado-Vides, J., Glasner, J. D., Rode, C. K., Mayhew, G. F., Gregor, J., Davis, N. W., Kirkpatrick, H. A., Goeden, M. A., Rose, D. J., Mau, B., and Shao, Y. (1997). The complete genome sequence of *Escherichia coli* K-12 [comment] [see comments]. Science 277, 1453-74.

Condon, C., Hourihane, S. L., Dang-Lawson, M., Escribano, J., and Matsuuchi, L. (2000). Aberrant trafficking of the B cell receptor Ig-alpha beta subunit in a B lymphoma cell line. J Immunol 165, 1427-37.

Coursen, J. D., Bennett, W. P., Gollahon, L., Shay, J. W., and Harris, C. C. (1997). Genomic instability and telomerase activity in human bronchial epithelial cells during immortalization by human papillomavirus-16 E6 and E7 genes. Exp Cell Res 235, 245-53.

Dickson, M. A., Hahn, W. C., Ino, Y., Ronfard, V., Wu, J. Y., Weinberg, R. A., Louis, D. N., Li, F. P., and Rheinwald, J. G. (2000). Human keratinocytes that express hTERT and also bypass a p16(INK4a)-enforced mechanism that limits life span become immortal yet retain normal growth and differentiation characteristics. Mol Cell Biol 20, 1436-47.

Dunham, I., Shimizu, N., Roe, B. A., Chissoe, S., Hunt, A. R., Collins, J. E., Bruskiewich, R., Beare, D. M., Clamp, M., Smink, L. J., Ainscough, R., Almeida, J. P., Babbage, A., Bagguley, C., Bailey, J., Barlow, K., Bates, K. N., Beasley, O., Bird, C. P., Blakey, S., Bridgeman, A. M., Buck, D., Burgess, J., Burrill, W. D., O'Brien, K. P., and et al. (1999). The DNA sequence of human chromosome 22 [see comments] [published erratum appears in Nature 2000 Apr. 20; 404(6780):904]. Nature 402, 489-95.

Edwards-Gilbert, G., and Milcarek, C. (1995). The binding of a subunit of the general polyadenylation factor cleavage polyadenylation specificity factor (CPSF) to polyadenylation sites changes during B cell development. Nucleic Acids Symposium Series 33, 229-233

Edwalds-Gilbert, G., and Milcarek, C. (1995). Regulation of poly(A) site use during mouse B-cell development involves a change in the binding of a general polyadenylation factor in a B-cell stage-specific manner. Molecular and Cellular Biology 15, 6420-6429.

Edwalds-Gilbert, G., Veraldi, K., and Milcarek, C. (1997). Alternative poly(A) site selection in complex transcription units: means to an end? Nucleic Acids Res 25, 2547-2561.

Flaspohler, J. A., Boczkowski, D., Hall, B. L., and Milcarek, C. (1995). The 3'-untranslated region of membrane exon 2 from the gamma 2a immunoglobulin gene contributes to efficient transcription termination. Journal of Biological Chemistry 270, 11903-11.

Flaspohler, J. A., and Milcarek., C. (1990). Myelomas and lymphomas expressing the IgG2a H chain gene have similar transcription termination regions. Journal of Immunology 144, 2802-2810.

Fraser, C. M., and Venter, J. C. (1980). Monoclonal antibodies to beta-adrenergic receptors: use in purification and molecular characterization of beta receptors. Proc Natl Acad Sci USA 77, 7034-8.

Galibert, F., Alexandraki, D., Baur, A., Boles, E., Chalwatzis, N., Chuat, J. C., Coster, F., Cziepluch, C., De Haan, M., Domdey, H., Durand, P., Entian, K. D., Gatius, M., Goffeau, A., Grivell, L. A., Hennemann, A., Herbert, C. J., Heumann, K., Hilger, F., Holleuberg, C. P., Huang, M. E., Jacq, CJauniaux, J. C., Katsoulou, C., Karpfinger-Hartl, L., and et al. (1996). Complete nucleotide sequence of *Saccharomyces cerevisiae* chromosome X. Embo J 15, 2031-49.

Galli, G., Guise, J. W., McDevitt, M. A., Tucker, P. W., and Nevins, J. R. (1987). Relative position and strengths of poly(A) sites as well as transcription termination are critical to membrane vs secreted mu-chain expression during B-cell development. Genes & Dev 1, 471-481.

Genovese, C., Harrold, S., and Milcarek, C. (1991). Differential mRNA stabilities affect mRNA levels in mutant mouse myeloma cells. Somat Cell Mol Genet. 17, 69-81.

Genovese, C., and Milcarek, C. (1990). Increased half-life of mu immunoglobulin mRNA during mouse B cell development increases its abundancy. Mol Immunol 27, 733-43.

Glennie, M. J., and Johnson, P. W. (2000). Clinical trials of antibody therapy. Immunol Today 21, 403-10.

Greenberg, R. A., O'Hagan, R. C., Deng, H., Xiao, Q., Hann, S. R., Adams, R. R., Lichtsteiner, S., Chin, L., Morin, G. B., and DePinho, R. A. (1999). Telomerase reverse transcriptase gene is a direct target of c-Myc but is not functionally equivalent in cellular transformation. Oncogene 18, 1219-26.

Greene, G. L., Nolan, C., Engler, J. P., and Jensen, E. V. (1980). Monoclonal antibodies to human estrogen receptor. Proc Natl Acad Sci USA 77, 5115-9.

Guise, J., Lim, P., Yuan, D., and Tucker, P. (1988). Alternative expression of secreted and membrane forms of immunoglobulin μ-chain is regulated by transcriptional termination in stable plasmacytoma transfectants. Journal of Immunology 140, 3988-3994.

Hall, B. L., and Milcarek, C. (1989). Sequence and polyadenylation site determination of murine inimmunoglobulin gamma 2a membrane 3' untranslated region. Mol Immunol 26, 819-826.

Hashimoto, S., Chiorazzi, N., and Gregersen, P. K. (1995). Alternative splicing of CD79a (Ig-alpha/inb-1) and CD79b (Ig-beta/B29) RNA transcripts in human B cells. Mol Immunol 32, 651-9.

Hattori, M., Fujiyama, A., Taylor, T. D., Watanabe, H., Yada, T., Park, H. S., Toyoda, A., Ishii, K., Totoki, Y., Choi, D. K., Soeda, E., Ohki, M., Takagi, T., Sakaki, Y., Taudien, S., Blechschmidt, K., Polley, A., Menzel, U., Delabar, J., Kumpf, K., Lehmann, R., Patterson, D., Reichwald, K., Rump, A., Schillhabel, M., and Schudy, A. (2000). The DNA sequence of human chromosome 21. The chromosome 21 mapping and sequencing consortium [see comments]. Nature 405, 311-9.

Hombach, J., Lottspeich, F., and Reth, M. (1990a). Identification of the genes encoding the IgM-alpha and Ig-beta components of the IgM antigen receptor complex by amino-terminal sequencing. Eur J Immunol 20, 2795-9.

Hombach, J., Tsubata, T., Leclercq, L., Stappert, H., and Reth, M. (1990b). Molecular components of the B-cell antigen receptor complex of the IgM class. Nature 343, 760-2.

Hurwitz, J. L., Coleclough, C., and Cebra, J. J. (1980). CH gene rearrangements in IgM-bearing B cells and in the nounal splenic DNA component of hybridomas making different isotypes of antibody. Cell 22, 349-59.

Janeway, C. A., and Travers, P. (1994). Immunobiology. The immune system in health and disease (New York: Garland Publishing, Inc).

Kanavaros, P., Gaulard, P., Charlotte, F., Martin, N., Ducos; C., Lebezu, M., and Mason, D. Y. (1995). Discordant expression of immunoglobulin and its associated molecule mb-1/CD79a is frequently found in mediastinal large B cell lymphomas. Am J Pathol 146, 735-41.

Kandasamy, M. K., McKinney, E., and Meagher, R. B. (1999). The late pollen specific actins in angiosperms. Plant J 18, 681-691.

Kelly, D. E., and Perry, R. P. (1986). Transcriptional and post-transcriptional control of Ig mRNA production during B lymphocyte development. Nucleic Acids Research 14, 5431-5441.

Kim, H. S., Shin, J. Y., Yun, J. Y., Ahn, D. K., and Le, J. Y. (2001). Immortalization of human embryonic fibroblasts by overexpression of c-myc and simian virus 40 large T antigen. Exp Mol Med 33, 293-8.

Kiyono, T., Foster, S. A., Koop, J. I., McDougall, J. K., Galloway, D. A., and Klingelhutz, A. J. (1998). Both Rb/p161NK4a inactivation and telomerase activity are required to immortalize human epithelial cells. Nature 396, 84-8.

Kohler, G., and Milstein, C. (1975). Continuous cultures of fused cells secreting antibody of predefined specificity. Nature 256, 495.

Kobrin, B. J., Milcarek, C., and Morrison, S. L. (1986). Sequences near the 3' secretion-specific polyadenylation site influence levels of secretion-specific and membrane-specific IgG2b in RNA in myeloma cells. Molecular and Cellular Biology 6, 1687-1697.

Konstantinos, N. S., and al., e. (1999). Use of monoclonal antibodies for the diagnosis and treatment of bladder cancer. Hybridoma 18, 219-224.

Lassman, C. R., and Milcarek, C. (1992). Regulated expression of the mouse γ2b Ig H chain gene is influenced by polyA site order and strength. J Immunol 148, 2578-2585.

Lassman, C. R., Matis, S., Hall, B. L., Toppmeyer, D. L., and Milcarek, C. (1992). Plasma cell-regulated polyadenylation at the Ig gamma 2b secretion-specific poly(A) site. J Immunol 148, 1251-60.

Lebman, D. A., Park, M. J., Fatica, R., and Zhang, Z. (1992). Regulation of usage of membrane and secreted 3' termini of alpha mRNA differs from mu mRNA. Journal of Immunology 148, 3282-3289.

Li, Y., Kandasamy, M. K., and Meagher, R. B. (2001). Rapid isolation of monoclonal antibodies: monitoring enzymes in the phytochelatin synthesis pathway. Plant Physiol in press.

Lockhart, D. J., and Winzeler, E. A. (2000). Genomics, gene expression and DNA arrays. Nature 405, 827-36.

MacBeath, G., and Schreiber, S. L. (2000). Printing, proteins as microarrays for high-throughput function determination [see comments]. Science 289, 1760-3

Matis, S. A., Martincic, K., and Milcarek, C. (1996). B-lineage regulated polyadenylation occurs on weak poly(A) sites regardless of sequence composition at the cleavage and downstream regions. Nucleic Acids Res 24, 4684-92.

McClelland, M., and Wilson, R. K. (1998). Comparison of sample sequences of the *Salmonella typhi* genome to the sequence of the complete *Escherichia coli* K-12 genome. Infect Immun 66, 4305-12.

Meilhoc, E., Wittrup, K. D., and Bailey, J. E. (1989). Application of flow cytometric measurement of surface IgG in kinetic analysis of monoclonal antibody synthesis and secretion by murine hybridoma cells. J Immunol Methods 121, 167-74.

Milcarek, C., and Hall, B. (1985). Cell-specific expression of secreted versus membrane forms of immunoglobulin gamma 2b mRNA involves selective use of alternate polyadenylation sites. Mol Cell Biol 5, 2514-2520.

Milcarek, C., Hartman, M., and Croll, S. (1996). Changes in abundance of IgG 2a mRNA in the nucleus and cytoplasm of a murine B-lymphoma before and after fusion to a myeloma cell. Mol Immunol 33, 691-701.

Milcarek, C., Suda-Hartman, M., and Croll, S. C. (1996). Changes in abundance of IgG 2a mRNA in the nucleus and cytoplasm of a murine B-lymphoma before and after fusion to a myeloma cell. Mol Immunol 33, 691-701.

Miller, R. A., Maloney, D. G., Warnke, R., and Levy, R. (1982). Treatment of B-cell lymphoma with monoclonal anti-idiotype antibody. N Engl J Med 306, 517-22.

Milstein, C. (2000). With the benefit of hindsight. Immunol Today 21, 359-64.

Morio, T., Urushihara, H., Saito, T., Ugawa, Y., Mizuno, H., Yoshida, M., Yoshino, R., Mitra, B. N., Pi, M., Sato, T., Takemoto, K., Yasukawa, H., Williams, J., Maeda, M., Takeuchi, I., Ochiai, H., and Tanaka, Y. (1998). The Dictyostelium developmental cDNA project: generation and analysis of expressed sequence tags from the first-finger stage of development. DNA Res 5, 335-40.

Mullner, S., Neumann, T., and Lottspeich, F. (1998). Proteomics—a new way for drug target discovery. Arzneimittelforschung 48, 93-5.

O'Reilly, L. A., Cullen, L., Moriishi, K., O'Connor, L., Huang, D. C., and Strasser, A. (1998). Rapid hybridoma screening method for the identification of monoclonal antibodies to low-abundance cytoplasmic proteins. Biotechniques 25, 824-30.

Oi, V. T., Morrison, S. L., Herzenberg, L. A., and Berg, P. (1983). Immunoglobulin gene expression in transfoinied lymphoid cells. Proc Natl Acad Sci USA 80, 825-9.

Opitz, O. G., Suliman, Y., Hahn, W. C., Harada, H., Blum, H. E., and Rustgi, A. K. (2001). Cyclin D1 overexpression and p53 inactivation immortalize primary oral keratinocytes by a telomerase-independent mechanism. J Clin Invest 108, 725-32.

Pandey, A., and Mann, M. (2000). Proteomics to study genes and genomes. Nature 405, 837-46.

Pandey, A., Podtelejnikov, A. V., Blagoev, B., Bustelo, X. R., Mann, M., and Lodish, H. F. (2000). Analysis of receptor signaling pathways by mass spectrometry: identification of vav-2 as a substrate of the epideinial and platelet-derived growth factor receptors. Proc Natl Acad Sci USA 97, 179-84.

Parks, D. R., Bryan, V. M., 01, V. T., and Herzenberg, L. A. (1979). Antigen-specific identification and cloning of hybridomas with a fluorescence-activated cell sorter. Proc Natl Acad Sci USA 76, 1962-6.

Persidis, A. (1998). Proteomics. Nat. Biotechnol 16, 393-4.

Price, C. P., and Newman, D. J. (1997). Principles and practice of Immunoassay,

Richards, J. D., Gold, M. R., Hourihane, S. L., DeFranco, A. L., and Matsuuchi, L. (1996). Reconstitution of B cell antigen receptor-induced signaling events in a nonlymphoid cell line by expressing the Syk protein-tyrosine kinase. J Biol Chem 271, 6458-66.

Russo, I., Silver, A. R., Cuthbert, A. P., Griffin, D. K., Trott, D. A., and Newbold, R. F. (1998). A telomere-independent senescence mechanism is the sole barrier to Syrian hamster cell immortalization. Oncogene 17, 3417-26.

Sakaguchi, N., Kashiwamura, S., Kimoto, M., Thalmann, P., and Melchers, F. (1988). B lymphocyte lineage-restricted expression of mb-1, a gene with CD3-like structural properties. Embo J 7, 3457-64.

Sato, S., Nakamura, Y., Kaneko, T., Katoh, T., Asamizu, E., Kotani, H., and Tabata, S. (2000). Structural analysis of Arabidopsis thaliana chromosome 5. X. Sequence features of the regions of 3,076,755 bp covered by sixty P1 and TAC clones. DNA Res 7, 31-63.

Signals. (2000). Companies load up on magic bullets, Signals Magazine October, 1-9 (http://www.recap.com/signalsma).

Sun, L. K., Liou, R. S., Sun, N. C., Gossett, L. A., Sun, C., Davis, F. M., MacGlashan, D. W., Jr., and Chang, T. W. (1991). Transfectomas expressing both secreted and membrane-bound forms of chimeric IgE with anti-viral specificity. J Immunol 146, 199-205.

Yuan, D., and Tucker, P. W. (1984). Transcriptional regulation of the mu-delta heavy chain locus in normal murine B-lymphocytes. J Exp Medicine 160, 564-572.

What is claimed is:

1. A non-human transgenic animal comprising B cells comprising a transgene, wherein the transgene comprises a nucleic acid encoding Igα and Igβ surface-expressed antibody receptor, wherein the nucleic acid is introduced into the germline of the transgenic animal and is incorporated into the animal's genome, and wherein the transgene is expressed in one or more of immature B cells, mature naïve B cells, mature activated B cells, memory B cells, B lineage lymphocytes and plasma cells, wherein expression of the transgene results in an increase in the level of surface-expressed antibody on the surface of one or more immature B cells, mature naïve B cells, mature activated B cells, memory B cells, B lineage lymphocytes and plasma cells relative to non-transgenic cells.

2. The non-human transgenic animal of claim 1, wherein the Igα and/or Igβ surface-expressed antibody receptor is mutated.

3. The non-human transgenic animal of claim 1, wherein at least one surface-expressed antibody receptor is chimeric wherein the chimeric receptor comprises one receptor domain that is derived from a different species of animal that is different than the remaining domains.

4. The non-human transgenic animal of claim 2, wherein the mutated Igα receptor comprises one or more mutations selected from the group consisting of: Y176F, Y182F, Y193F, and Y204F.

5. The non-human transgenic animal of claim 2, wherein the mutated Igβ receptor comprises one or more mutations selected from the group consisting of: Y190F and Y206F.

6. A method of generating the non-human transgenic animal of claim 1 comprising:
   a) injecting a one or more transgenes comprising one or more nucleic acids encoding Igα and Igβ functionally linked to an expression sequence into an embryo;
   b) allowing the embryo to develop into an animal; and
   c) crossing the non-human transgenic animal of step (b) with a second animal to produce a third animal.

7. The method of claim 6, wherein the animal is a mouse.

8. The method of claim 6, wherein the animal is a rabbit.

9. The method of claim 6, wherein the animal is a rat.

10. The method of claim 6, wherein the animal is a guinea pig.

11. The method of claim 6, wherein the expression of the transgene is inducible.

12. The transgenic animal of claim 1, wherein the expression of the transgene is controlled by the cre-lox expression system.

13. The transgenic animal of claim 1, wherein the expression of the transgene is controlled by an inducible tetracycline promoter system.

14. The non-human transgenic animal produced by the method of claim 6.

15. A B cell obtained from the non-human transgenic animal of claim claim 1.

16. The non-human transgenic animal of claim 3, wherein one receptor domain of the chimeric surface-expressed antibody receptor is selected from the group consisting of the human extracellular domain, the human transmembrane domain, and the human intracellular domain.

* * * * *

UNITED STATES PATENT AND TRADEMARK OFFICE
CERTIFICATE OF CORRECTION

PATENT NO. : 8,912,385 B2  
APPLICATION NO. : 12/620209  
DATED : December 16, 2014  
INVENTOR(S) : Richard B. Meagher It is certified that error appears in the above-identified patent and that said Letters Patent is hereby corrected as shown below:

In the Specification,

Column 1, line 1, an "ACKNOWLEDGMENTS" section should be inserted above the "FIELD OF THE INVENTION" section that reads as follows:

--This invention was made with government support under the National Institutes of Health (Grant GM36397) and the Department of Energy (Grant DE-FG07-96ER20257). The U.S. Government has certain rights in this invention.--

Signed and Sealed this  
Seventh Day of July, 2015

Michelle K. Lee  
*Director of the United States Patent and Trademark Office*

SEQUENCE LISTING

```
<160> NUMBER OF SEQ ID NOS: 8

<210> SEQ ID NO 1
<211> LENGTH: 681
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 1
aagcttgcca ccatgccagg gggtctagaa gccctcagag ccctgcctct cctcctcttc      60
ttgtcatacg cctgtttggg tcccggatgc caggccctgc gggtagaagg gggtccacca     120
tccctgacgg tgaacttggg cgaggaggcc cgcctcacct gtgaaaacaa tggcaggaac     180
cctaatatca catggtggtt cagccttcag tctaacatca catggccccc agtgccactg     240
ggtcctggcc agggtaccac aggccagctg ttcttccccg aagtaaacaa gaaccacagg     300
ggcttgtact ggtgccaagt gatagaaaac aacatattaa aacgctcctg tggtacttac     360
ctccgcgtgc gcaatccagt ccctaggccc ttcctggaca tggggaagg taccaagaac     420 cgcatcatca cagcagaagg gatcatcttg ctgttgtgtg cagtggtgcc agggacgctg     480
ctgctattca ggaaacggtg gcaaaatgag aagtttgggg tggacatgcc agatgactat     540
gaagatgaaa atctctatga gggcctgaac cttgatgact gttctatgta tgaggacatc     600 tccagggac tccagggcac ctaccaggat gtgggcaacc tccacattgg agatgcccag     660
ctggaaaagc catgagaatt c                                              681

<210> SEQ ID NO 2
<211> LENGTH: 705
<212> TYPE: DNA
<213> ORGANISM: Artificial Sequence
<220> FEATURE:
```

<223> OTHER INFORMATION: Description of Artificial Sequence:/Note = synthetic construct

<400> SEQUENCE: 2

```
aagcttgcca ccatggccac actggtgctg tcttccatgc cctgccactg gctgttgttc      60
ctgctgctgc tcttctcagg tgagccggta ccagcaatga caagcagtga cctgccactg     120
aatttccaag gaagcccttg ttcccagatc tggcagcacc cgaggtttgc agccaaaaag     180
cggagctcca tggtgaagtt tcactgctac acaaaccact caggtgcact gacctggttc     240
cgaaagcgag ggagccagca gccccaggaa ctggtctcag aagagggacg cattgtgcag     300
acccagaatg ctctgtctca cccctcact atccaaaaca tccagtacga ggataatggt      360
atctacttct gcaagcagaa atgtgacagc gccaaccata atgtcaccga cagctgtggc     420
acggaacttc tagtcttagg attcagcacg ttggaccaac tgaagcggcg gaacacactg     480
aaagatggca ttatcttgat ccagaccctc ctcatcatcc tcttcatcat tgtgcccatc     540
ttcctgctac ttgacaagga tgacggcaag gctgggatcg aggaagatca cacctatgag     600
ggcttgaaca ttgaccagac agccacctat gaagacatag tgactcttcg gacaggggag     660
gtaaagtggt cggtaggaga gcatccaggc caggaatgac tcgag                      705
```

<210> SEQ ID NO 3
<211> LENGTH: 220
<212> TYPE: PRT
<213> ORGANISM: Artificial Sequence
<220> FEATURE:
<223> OTHER INFORMATION: Description of Artificial Sequence:/Note = synthetic construct

<400> SEQUENCE: 3

Met Pro Gly Gly Leu Glu Ala Leu Arg Ala Leu Pro Leu Leu Leu Phe
1               5                   10                  15

Leu Ser Tyr Ala Cys Leu Gly Pro Gly Cys Gln Ala Leu Arg Val Glu
            20                  25                  30

Gly Gly Pro Pro Ser Leu Thr Val Asn Leu Gly Glu Glu Ala Arg Leu
        35                  40                  45

Thr Cys Glu Asn Asn Gly Arg Asn Pro Asn Ile Thr Trp Trp Phe Ser
    50                  55                  60

Leu Gln Ser Asn Ile Thr Trp Pro Pro Val Pro Leu Gly Pro Gly Gln
65                  70                  75                  80

Gly Thr Thr Gly Gln Leu Phe Phe Pro Glu Val Asn Lys Asn His Arg
                85                  90                  95

Gly Leu Tyr Trp Cys Gln Val Ile Glu Asn Asn Ile Leu Lys Arg Ser
            100                 105                 110

Cys Gly Thr Tyr Leu Arg Val Arg Asn Pro Val Pro Arg Pro Phe Leu
        115                 120                 125

Asp Met Gly Glu Gly Thr Lys Asn Arg Ile Ile Thr Ala Glu Gly Ile
    130                 135                 140

Ile Leu Leu Phe Cys Ala Val Val Pro Gly Thr Leu Leu Leu Phe Arg
145                 150                 155                 160

Lys Arg Trp Gln Asn Glu Lys Phe Gly Val Asp Met Pro Asp Asp Tyr
                165                 170                 175

Glu Asp Glu Asn Leu Tyr Glu Gly Leu Asn Leu Asp Asp Cys Ser Met
            180                 185                 190

Tyr Glu Asp Ile Ser Arg Gly Leu Gln Gly Thr Tyr Gln Asp Val Gly
        195                 200                 205

Asn Leu His Ile Gly Asp Ala Gln Leu Glu Lys Pro
    210                 215                 220

<210> SEQ ID NO 4
<211> LENGTH: 228
<212> TYPE: PRT
<213> ORGANISM: Artificial Sequence
<220> FEATURE:
<223> OTHER INFORMATION: Description of Artificial Sequence:/Note = synthetic construct

<400> SEQUENCE: 4

Met Ala Thr Leu Val Leu Ser Ser Met Pro Cys His Trp Leu Leu Phe
 1               5                  10                  15

Leu Leu Leu Leu Phe Ser Gly Glu Pro Val Pro Ala Met Thr Ser Ser
            20                  25                  30

Asp Leu Pro Leu Asn Phe Gln Gly Ser Pro Cys Ser Gln Ile Trp Gln
        35                  40                  45

His Pro Arg Phe Ala Ala Lys Lys Arg Ser Ser Met Val Lys Phe His
    50                  55                  60

Cys Tyr Thr Asn His Ser Gly Ala Leu Thr Trp Phe Arg Lys Arg Gly
65                  70                  75                  80

Ser Gln Gln Pro Gln Glu Leu Val Ser Glu Gly Arg Ile Val Gln
                85                  90                  95

Thr Gln Asn Gly Ser Val Tyr Thr Leu Thr Ile Gln Asn Ile Gln Tyr
            100                 105                 110

Glu Asp Asn Gly Ile Tyr Phe Cys Lys Gln Lys Cys Asp Ser Ala Asn
        115                 120                 125

His Asn Val Thr Asp Ser Cys Gly Thr Glu Leu Leu Val Leu Gly Phe
    130                 135                 140

Ser Thr Leu Asp Gln Leu Lys Arg Arg Asn Thr Leu Lys Asp Gly Ile
145                 150                 155                 160

Ile Leu Ile Gln Thr Leu Leu Ile Ile Leu Phe Ile Ile Val Pro Ile
                165                 170                 175

Phe Leu Leu Leu Asp Lys Asp Asp Gly Lys Ala Gly Met Glu Glu Asp
            180                 185                 190

His Thr Tyr Glu Gly Leu Asn Ile Asp Gln Thr Ala Thr Tyr Glu Asp
        195                 200                 205

Ile Val Thr Leu Arg Thr Gly Glu Val Lys Trp Ser Val Gly Glu His
    210                 215                 220

Pro Gly Gln Glu
225

<210> SEQ ID NO 5
<211> LENGTH: 49
<212> TYPE: DNA
<213> ORGANISM: Artificial Sequence
<220> FEATURE:
<223> OTHER INFORMATION: Description of Artificial Sequence:/note = synthetic construct

<400> SEQUENCE: 5
tagtgaacta gtaagcttgc caccatgcca gggggtctag aagccctca                49

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence:/note =

```
        synthetic construct

<400> SEQUENCE: 6
gtctagatcg atgaattctc atggcttttc agctgggca tc                    42

<210> SEQ ID NO 7
<211> LENGTH: 48
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 7
tagtgaacta gtaagcttgc caccatggcc acactggtgc tgtcttcc             48

<210> SEQ ID NO 8
<211> LENGTH: 48
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 8
gtctagatcg atctcgagtc attcctggcc tggatgctct cctaccga             48
```